US012628827B2

(12) United States Patent
Dhage et al.

(10) Patent No.: US 12,628,827 B2
(45) Date of Patent: May 19, 2026

(54) ISOXAZOLINE COMPOUNDS AND THEIR USE AS PEST CONTROL AGENTS

(71) Applicant: PI INDUSTRIES LIMITED, Udaipur-Rajasthan (IN)

(72) Inventors: Yogesh Daulat Dhage, Ahmednagar (IN); Jagadish Pabba, Udaipur (IN); Sachin Ashok Badgujar, Jalgaon (IN); Jella Rama Raju, Andhra (IN); Rohit Saxena, Uttar (IN); Hardik Y Purohit, Vadodara (IN); Ravikumar Suryanarayana Saragur, Bengaluru (IN); Alexander G.M. Klausener, Pulheim (DE)

(73) Assignee: PI INDUSTRIES LIMITED, Udaipur-Rajasthan (IN)

( * ) Notice: Subject to any disclaimer, the term of this patent is extended or adjusted under 35 U.S.C. 154(b) by 455 days.

(21) Appl. No.: 18/266,077

(22) PCT Filed: Dec. 10, 2021

(86) PCT No.: PCT/IB2021/061541

§ 371 (c)(1),
(2) Date: Jun. 8, 2023

(87) PCT Pub. No.: WO2022/123502

PCT Pub. Date: Jun. 16, 2022

(65) Prior Publication Data

US 2024/0057604 A1 Feb. 22, 2024

(30) Foreign Application Priority Data

Dec. 11, 2020 (IN) ............................ 202011053960

(51) Int. Cl.

| | |
|---|---|
| ***A01N 43/80*** | (2006.01) |
| ***A01P 7/04*** | (2006.01) |
| ***C07D 413/12*** | (2006.01) |

(52) U.S. Cl.

CPC ................ *A01N 43/80* (2013.01); *A01P 7/04* (2021.08); *C07D 413/12* (2013.01)

(58) Field of Classification Search

CPC .......... A01N 43/80; A01P 7/04; C07D 413/12

USPC .......................................................... 514/378

See application file for complete search history.

(56) References Cited

FOREIGN PATENT DOCUMENTS

EP 1731512 A1 12/2006

OTHER PUBLICATIONS

PCT—ISR (PCT/IB2021/061541)—Mar. 14, 2022 (3 pgs).
PCT—WR OPN (PCT/IB2021/061541)—Mar. 14, 2022 (5 pgs).

*Primary Examiner* — Kahsay Habte

(74) *Attorney, Agent, or Firm* — Lippes Mathias LLP

(57) ABSTRACT

The present invention discloses an isoxazoline compounds of formula (I),

Formula (I)

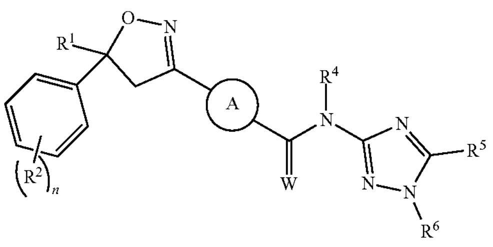

wherein, $R^1$, $R^2$, $R^4$, $R^5$, $R^6$, A, W and n are as defined in the detailed description. The present invention further discloses methods for preparation of compounds of formula (I) and use of the compounds of formula (I) as a pest control agent.

17 Claims, No Drawings

ISOXAZOLINE COMPOUNDS AND THEIR USE AS PEST CONTROL AGENTS

This application is a National Stage Entry of International Application No. PCT/IB2021/061541, filed Dec. 10, 2021, which claims priority to Indian Application No. 202011053960, filed Dec. 11, 2020, the contents of which are incorporated by reference herein.

FIELD OF THE INVENTION

The present invention relates to compounds of formula (I). More particularly, the present invention relates to isoxazoline compounds of formula (I) and a process for the preparation thereof. The present invention further relates to the use of isoxazoline compounds of formula (I) as pest control agents.

BACKGROUND OF THE INVENTION

Invertebrate pests, in particular arthropods and nematodes, destroy growing and harvested crops causing severe economic loss to the food supply. Further, insects attack on wooden dwelling and commercial structures, thereby causing large economic losses to property. Therefore, there is an ongoing need for new agents for combating invertebrate pests such as insects, arachnids and nematodes. The currently available modern insecticides and acaricides have to satisfy many requirements, for example regarding the level of activity, long lasting efficacy, broadness of insecticidal spectrum and other beneficial effects, and the possible use thereof. Efforts have been made during the past decades to develop selective insecticides that are acting specifically on biochemical modes of action being present only in insects or mites, but additionally showing properties that differ from known insecticides in an advantageous way.

Isoxazoline compounds with pesticidal activity are known and described, for example, in WO2005085216 WO2007026965, WO2008154528 and WO2016102482. These documents disclose an isoxazoline substituted phenyl or heterocyclic amides.

Further, by applying such pesticides in a conventional way over several years, many pests develop a resistance against that pesticide and are no longer sufficiently controlled, and this difficult situation has been even increasing during recent years. Furthermore, some of those existing pesticides are highly toxic, or remain for a long time in the environment due to their residual properties, which may become a growing problem due to the disruption of ecosystems.

Therefore, there is a continuous need for new compounds which are more effective in combating invertebrate pests, are less toxic, and are environmentally safer and/or have different modes of action.

WO2005085216 discloses the following compound:

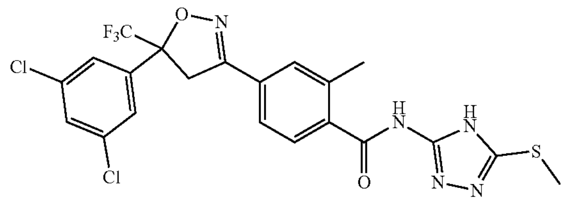 [SMILES: CSc1nnc(NC(=O)c2ccc(C3=NOC(c4cc(Cl)cc(Cl)c4)(C(F)(F)F)C3)cc2C)[nH]1]

However, this patent application does not disclose any compounds which have a di-substituted triazole amide moiety, i.e. carrying a substitution on at least one of the nitrogen and carbon atoms of the triazole ring. In the present invention it was surprisingly found that 1,2,4-triazol-3-amines having substitutions on a nitrogen and a carbon atom of the triazole moiety showed significant improvement concerning the biological activity against harmful pests.

In view of the above mentioned facts, the present invention envisages such compounds that satisfy or overcome drawbacks associated with the prior art. It has now surprisingly been found that certain novel pesticidally active isoxazoline compounds that are carrying a di-substituted triazole amide moiety being subject of this invention, have favorable properties as pesticides, as desired.

SUMMARY OF THE INVENTION

Accordingly, the present invention provides an isoxazoline compound of formula (I) or agriculturally acceptable salts, isomers/structural isomers, stereo-isomers, diastereomers, enantiomers, tautomers, metal complexes, polymorphs, or N-oxides thereof.

Formula (I)

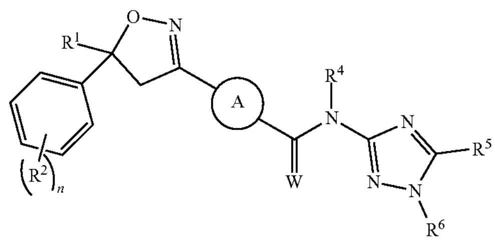

wherein, $R^1$, $R^2$, $R^4$, $R^5$, $R^6$, A, W and n are as defined in the detailed description.

In one embodiment, the present invention provides a process for preparing the compound of formula (I) or agriculturally acceptable salts thereof.

In another embodiment, the present invention provides a composition for controlling or preventing invertebrate pests comprising a biologically effective amount of the compound of formula (I), agriculturally acceptable salts, isomers/structural isomers, stereo-isomers, diastereomers, enantiomers, tautomers, metal complexes, polymorphs, or N-oxides thereof and at least one additional component selected from the group consisting of surfactants and auxiliaries.

In yet another embodiment, the composition further comprises at least one additional biologically active and compatible compound selected from fungicides, insecticides, nematicides, acaricides, biopesticides, herbicides, plant growth regulators, antibiotics, fertilizers or nutrients.

In still another embodiment, the present invention provides the use of the compound of formula (I), agriculturally acceptable salts, isomers/structural isomers, stereo-isomers, diastereomers, enantiomers, tautomers, metal complexes, polymorphs, or N-oxides, composition or combination thereof, for combating invertebrate pests in agricultural crops and/or horticultural crops or parasites on animals.

In yet still another embodiment, the present invention provides a method of combating invertebrate pests comprising contacting the invertebrate pests, their habitat, breeding ground, food supply, plant, seed, cuttings, soil, area, material or environment in which the invertebrate pests are growing or may grow, or the materials, plants, seeds, soils, surfaces or spaces to be protected from pest attack or infestation with a biologically effective amount of the compound of formula (I) or agriculturally acceptable salts, isomers/structural isomers, stereo-isomers, diastereomers, enantiomers, tautomers, metal complexes, polymorphs, or N-oxides thereof composition or combination thereof.

DETAILED DESCRIPTION OF THE INVENTION

Definitions

The definitions provided herein for the terminologies used in the present disclosure are for illustrative purpose only and in no manner limit the scope of the present invention disclosed in the present disclosure.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Further, unless expressly stated to the contrary, "or" refers to an inclusive "or" and not to an exclusive "or". For example, a condition A "or" B is satisfied by any one of the following: A is true (or present) and B is false (or not present), A is false (or not present) and B is true (or present), and both A and B are true (or present).

Also, the indefinite articles "a" and "an" preceding an element or component of the present invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" refers to a living organism of the Phylum Nematoda. The term "helminths" includes roundworms, heartworms, phytophagous nematodes (Nematoda), flukes (Tematoda), acanthocephala and tapeworms (Cestoda).

The term "agronomic" refers to the production of field crops such as for food, feed and fiber and includes the growth of corn, soybeans and other legumes, rice, cereals (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruits (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from an invertebrate parasitic pest by administering a parasiticidally effective (i.e. biologically effective) amount of a compound of the present invention, typically in the form of a composition formulated for veterinary use, to the animal to be protected. As referred to in the present disclosure and claims, the terms "parasiticidal" and "parasiticidally" refer to observable effects on an invertebrate parasite pest to provide protection of an animal from the pest. Parasiticidal effects typically relate to diminishing the occurrence or activity of the target invertebrate parasitic pest. Such effects on the pest include death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

The compounds of the present disclosure may be present either in pure form or as mixtures of different possible isomeric forms such as stereoisomers or constitutional isomers. The various stereoisomers include enantiomers, diastereomers, chiral isomers, atropisomers, conformers, rotamers, tautomers, optical isomers, polymorphs, and geometric isomers. Any desired mixtures of these isomers fall within the scope of the claims of the present disclosure. One skilled in the art will appreciate that one stereoisomer may be more active and/or may exhibit beneficial effects when enriched relative to the other isomer(s) or when separated from the other isomer(s). Additionally, the person skilled in the art knows processes or methods or technology to separate, enrich, and/or to selectively prepare said isomers.

The meaning of various terms used in the description shall now be illustrated.

The term "enantiomerically enriched" refers to a chiral substance whose enantiomeric ratio is greater than 50:50 but less than 100:0.

The term "aliphatic compound/s" or "aliphatic group/s" used herein is an organic compound/s whose carbon atoms are linked in straight chains, branched chains, or non-aromatic rings.

The term "alkyl", used either alone or in compound words such as "alkylthio" or "haloalkyl" or —N(alkyl) or alkylcarbonylalkyl or alkylsulphonylamino includes straight-chain or branched $C_1$ to $C_{15}$ alkyl, more preferably $C_1$ to $C_{10}$ alkyl, most preferably $C_1$ to $C_6$ alkyl. Representative examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, carbonyl, carbonyloxy and the like, are at the end.

The term "cyanoalkyl" or "cyano-$C_1$-$C_8$-alkyl" as used herein refers to straight-chain or branched alkyl groups having 1 to 8 ("$C_1$-$C_8$-cyanoalkyl") or 1 to 6 ("$C_1$-$C_6$-cyanoalkyl") carbon atoms (as mentioned above) preferably 1-4 carbon atoms, where 1 or 2 hydrogen, preferably 1 of the hydrogen atoms in these groups are replaced by a cyano (CN) group. Non limiting examples are cyanomethyl, 1-cyanoethyl, 2-cyanoethyl, 1-cyanopropyl, 2-cyanopropyl, 3-cyanopropyl, 1-cyanobutyl, 2-cyanobutyl, 3-cyanobutyl, 4-cyanobutyl and the like.

The term "alkenyl", used either alone or in compound words includes straight-chain or branched $C_2$ to $C_{15}$ alkenes, more preferably $C_2$ to $C_{10}$ alkenes, most preferably $C_2$ to $C_6$ alkenes. Representative examples of alkenes include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl and the different isomers. "Alkenyl" also includes polyenes such as 1,2-propadienyl and 2,4-hexadienyl. This definition also applies to alkenyl as a part of a composite substituent, for example haloalkenyl and the like, unless defined specifically elsewhere.

The term "alkynyl", used either alone or in compound words includes straight-chain or branched $C_2$ to $C_{15}$ alkynes, more preferably $C_2$ to $C_{10}$ alkynes, most preferably $C_2$ to $C_6$ alkynes. Non-limiting examples of alkynes include ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, and 1-ethyl-1-methyl-2-propynyl and the different isomers. This definition also applies to alkynyl as a part of a composite substituent, for example haloalkynyl etc., unless specifically defined elsewhere. The term "alkynyl" can also include moieties comprised of multiple triple bonds such as 2,5-hexadiynyl.

The term "cycloalkyl" means alkyl closed to form a ring. Non-limiting examples include but are not limited to cyclopropyl, cyclobutyl, cyclopentyl and cyclohexyl. This definition also applies to cycloalkyl as a part of a composite substituent, for example cycloalkylalkyl etc., unless specifically defined elsewhere.

The term "cyanocycloalkyl" as used herein refers to alkyl closed to form a ring groups having 3 to 8 ("$C_3$-$C_8$-cyanoalkyl") carbon atoms (as mentioned above), where 1 or 2, preferably 1, of the hydrogen atoms in these groups are replaced by a cyano (CN) group. Non limiting examples are 1-cyanocyclopropyl, 2-cyanocyclopropyl, 1-cyanocyclobutyl, 2-cyanocyclobutyl, 3-cyanocyclobutyl, 1-cyanocyclopentyl, 2-cyanocyclopentyl, 3-cyclopentyl, 4-cyclopentyl, 1-cyanohexyl, 2-cyanohexyl, 3-cyanocyclohexyl, 4-cyanocyclohexyl and the like.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Non-limiting examples of "haloalkyl" include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1,1-dichloro-2,2,2-trifluoroethyl, and 1,1,1-trifluoroprop-2-yl. This definition also applies to haloalkyl as a part of a composite substituent, for example haloalkylaminoalkyl etc., unless specifically defined elsewhere.

The terms "haloalkenyl", "haloalkynyl" are defined analogously except that, instead of alkyl groups, alkenyl and alkynyl groups are present as a part of the substituent.

The term "hydroxy" means —OH, Amino means —NRR, wherein R can be H or any possible substituent such as alkyl. Carbonyl means —C(O)—, carbonyloxy means —OC(O)—, sulfinyl means SO, sulfonyl means $S(O)_2$.

The term "alkoxy" used either alone or in compound words included $C_1$ to $C_{15}$ alkoxy, more preferably $C_1$ to $C_{10}$ alkoxy, most preferably $C_1$ to $C_6$ alkoxy. Examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy and the different isomers. This definition also applies to alkoxy as a part of a composite substituent, for example haloalkoxy, alkynylalkoxy, etc., unless specifically defined elsewhere.

The term "alkoxycarbonyl" is an alkoxy group bonded to a skeleton via a carbonyl group (—CO—). This definition also applies to alkoxycarbonyl as a part of a composite substituent, for example cycloalkylalkoxycarbonyl and the like, unless specifically defined elsewhere.

The term "carbocycle" includes "aromatic carbocyclic ring system" and "nonaromatic carbocylic ring system" or polycyclic or bicyclic (spiro, fused, bridged, nonfused) ring compounds in which ring may be aromatic or non-aromatic (where aromatic indicates that the Huckel rule is satisfied and non-aromatic indicates that the Huckel rule is not statisfied).

The term "hetero" in connection with rings refers to a ring in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs.

The term "aromatic" indicates that the Huckel rule is satisfied and the term "non-aromatic" indicates that the Huckel rule is not satisfied.

The term "heterocycle" or "heterocyclic" or "heterocyclic ring system" includes "aromatic heterocycle" or "heteroaryl bicyclic ring system" and "nonaromatic heterocycle ring system" or polycyclic or bicyclic (spiro, fused, bridged, non-fused) ring compounds in which ring may be aromatic or non-aromatic, wherein the heterocycle ring contains at least one heteroatom selected from N, O, $S(O)_{0-2}$, and or C ring member of the heterocycle may be replaced by C(═O), C(═S), C(═CR*R*) and C═NR*, * indicates integers.

The term "non-aromatic heterocycle" or "non-aromatic heterocyclic" means three- to fifteen-membered, preferably three- to twelve-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxetanyl, oxiranyl, aziridinyl, thietanyl, tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, 1,2,4-oxadiazolidinyl, 1,2,4-thiadiazolidinyl, 1,2,4-triazolidin-1-yl, 1,2,4-triazolidin-3-yl, 1,2,3-triazolidinyl, 1,3,4-oxadiazolidinyl, 1,3,4-thiadiazolidinyl, 1,3,4-triazolidinyl, dihydrofuryl, dihydrothienyl, pyrrolinyl, isoxazolinyl, isothiazolinyl, dihydropyrazolyl, dihydrooxazolyl, dihydrothiazolyl, piperidinyl, pyrazynyl, morpholinyl, thiomorphlinyl, 1,3-dioxan-5-yl, tetrahydropyranyl, tetrahydrothienyl, hexahydropyridazinyl, hexahydropyrimidinyl, piperazinyl and cycloserines. This definition also applies to heterocyclyl as a part of a composite substituent, for example heterocyclylalkyl etc., unless specifically defined elsewhere.

The term "heteroaryl" or "aromatic heterocyclic" means 5 or 6-membered, fully unsaturated monocyclic ring system containing one to four heteroatoms from the group of oxygen, nitrogen and sulphur; if the ring contains more than one oxygen atom, they are not directly adjacent; 5-membered heteroaryl containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) furyl, thienyl, pyrrolyl, pyrazolyl, oxazolyl, thiazolyl, isoxazolyl, isothiazolyl, imidazolyl, 1,2,4-oxadiazolyl, 1,2,4-thiadiazolyl, 1,2,3-triazolyl, 1,2,4-triazolyl, 1,3,4-oxadiazolyl, 1,3,4-thiadiazolyl, 1,3,4-triazolyl, tetrazolyl; nitrogen-bonded 5-membered heteroaryl containing one to four nitrogen atoms, or benzofused nitrogen-bonded 5-membered heteroaryl containing one to three nitrogen atoms: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example (but not limited to) 1-pyrrolyl, 1-pyrazolyl, 1,2,4-triazol-1-yl, 1-imidazolyl, 1,2,3-triazol-1-yl and 1,3,4-triazol-1-yl.

6-membered heteroaryl which contains one to four nitrogen atoms: 6-membered heteroaryl groups which, in addition to carbon atoms, may contain, respectively, one to three and one to four nitrogen atoms as ring members, for example (but not limited thereto) pyridinyl, pyridazinyl, pyrimidinyl, pyrazinyl; benzofused 5-membered heteroaryl containing one to three nitrogen atoms or one nitrogen atom and one oxygen or sulphur atom: for example (but not limited to) indolyl, benzimidazolyl, indazolyl, benzofuranyl, benzothiophenyl, benzothiazolyl, benzoxazolyl, benzofused 6-membered heteroaryl which contains one to three nitrogen atoms: for example (but not limited to) quinolinyl, isoquinolinyl, quinoxalinyl, phthalazinyl, quinazolinyl and cinnolinyl. This definition also applies to heteroaryl as a part of a composite substituent, for example heteroarylalkyl etc., unless specifically defined elsewhere.

The term "Trialkylsilyl" includes three branched and/or straight-chain alkyl radicals attached to and linked through a silicon atom such as trimethylsilyl, triethylsilyl and t-butyl-dimethylsilyl. "Halotrialkylsilyl" denotes at least one of the three alkyl radicals is partially or fully substituted with halogen atoms which may be the same or different. The term "alkoxytrialkylsilyl" denotes at least one of the three alkyl radicals is substituted with one or more alkoxy radicals which may be the same or different. The term "trialkylsilyloxy" denotes a trialkylsilyl moiety attached through oxygen.

The term "amide" means A-R'C═ONR"—B, wherein R' and R" indicates substituents and A and B indicate any group.

The term "thioamide" means A-R'C═SNR"—B, wherein R' and R" indicates substituents and A and B indicate any group.

The total number of carbon atoms in a substituent group is indicated by the "$C_i$-$C_j$" prefix where i and j are numbers from 1 to 12. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of formula (I) is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript m in $(R)_m$ indicates an integer ranging from for example 0 to 4 then the number of substituents may be selected from the integers between 0 and 4 inclusive.

When a group contains a substituent which can be hydrogen, then, when this substituent is taken as hydrogen, it is recognized that said group is being un-substituted.

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skilled in the art to practice the embodiments herein. Accordingly, the examples should not be construed as limiting the scope of the embodiments herein.

The description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned in the description and the description/claims though might form a critical part of the present invention, any deviation from such numerical values shall still fall within the scope of the present invention if that deviation follows the same scientific principle as that of the present invention disclosed in the present invention. The inventive compound of the present invention may, if appropriate, be present as mixtures of different possible isomeric forms, especially of stereoisomers, for example E and Z, threo and erythro, and also optical isomers, but if appropriate also of tautomers. Both the E and the Z isomers, and also the threo and erythro isomers, and the optical isomers, any desired mixtures of these isomers and the possible tautomeric forms are disclosed and claimed.

The term "pest" for the purpose of the present disclosure includes but is not limited to nematodes, mites, ticks, insects and rodents. Also pest is an animal detrimental to humans or human concerns including crops, livestock, and forestry.

The term "plant" is understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights.

For the purpose of the present disclosure the term "plant" includes a living organism of the kind exemplified by trees, shrubs, herbs, grasses, ferns, and mosses, typically growing in a site, absorbing water and required substances through its roots, and synthesizing nutrients in its leaves by photosynthesis.

Examples of "plant" for the purpose of the present invention include but are not limited to agricultural crops such as wheat, rye, barley, triticale, oats or rice; beet, e.g. sugar beet or fodder beet; fruits and fruit trees, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit and citrus trees, such as oranges, lemons, grapefruits or mandarins; any horticultural plants, vegetables, such as spinach, lettuce, asparagus, cabbages, carrots, onions, tomatoes, potatoes, cucurbits or paprika; lauraceous plants, such as avocados, cinnamon or camphor; cucurbitaceae; oleaginous plants; energy and raw material plants, such as cereals, corn, soybean, other leguminous plants, rape, sugar cane or oil palm; tobacco; nuts; coffee; tea; cacao; bananas; peppers; vines (table grapes and grape juice grape vines); hop; turf; sweet leaf (also called *Stevia*); natural rubber plants or ornamental and forestry plants, such as flowers, shrubs, broad-leaved trees or evergreens, e.g. conifers; and on the plant propagation material, such as seeds, and the crop material of these plants.

Preferably, the plant for the purpose of the present invention includes but is not limited to cereals, corn, rice, soybean and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and vegetables, ornamentals, any floricultural plants and other plants for use of human and animals.

The term "plant parts" is understood to mean all parts and organs of plants above and below the ground. For the purpose of the present disclosure the term plant parts includes but is not limited to cuttings, leaves, twigs, tubers, flowers, seeds, branches, roots including taproots, lateral roots, root hairs, root apex, root cap, rhizomes, slips, shoots, fruits, fruit bodies, bark, stem, buds, auxillary buds, meristems, nodes and internodes.

The term "locus thereof" includes soil, surroundings of plant or plant parts and equipment or tools used before, during or after sowing/planting a plant or a plant part.

Application of the compounds of the present disclosure or the compound of the present disclosure in a composition optionally comprising other compatible compounds to a plant or a plant material or locus thereof include application by a technique known to a person skilled in the art which includes but is not limited to spraying, coating, dipping, fumigating, impregnating, injecting and dusting.

The term "applied" means adhered to a plant or plant part either physically or chemically including impregnation.

In one embodiment, the present invention provides a compound of formula (I),

Formula (I)

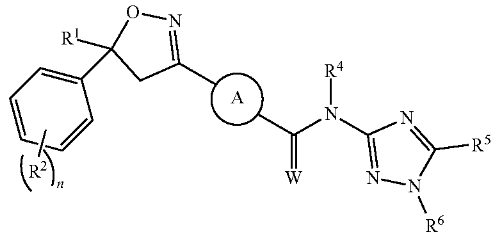

wherein, $R^1$ is selected from the group consisting of $C_1$-$C_6$-alkyl, $C_1$-$C_6$-haloalkyl, $C_3$-$C_6$-cycloalkyl and $C_3$-$C_6$-halocycloalkyl;

$R^2$ is selected from the group consisting of hydrogen, halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl and $C_3$-$C_8$-cycloalkyl;

ring A is selected from the group consisting of $C_6$-$C_{10}$ aryl and $C_5$-$C_{10}$-heterocyclyl group, which may optionally be substituted with one or more groups of $R^3$;

$R^3$ is selected from the group consisting of hydrogen, halogen, cyano, nitro, $C_1$-$C_4$-alkyl, $C_2$-$C_4$-alkenyl, $C_2$-$C_6$-alkynyl, $C_1$-$C_4$-haloalkyl, $C_2$-$C_4$-haloalkenyl, $C_2$-$C_6$-haloalkynyl, $C_3$-$C_4$-cycloalkyl, $C_3$-$C_8$-heterocyclyl, —$OC_3$-$C_4$-heterocyclyl, SCN, $SF_5$, NR'R", OR', $S(O)_m$R', and CR'═NR"; or two $R^3$ together with the atom to which they are attached or together with the further atoms selected from the group consisting of C, N, O, S and optionally including 1 to 3 ring members selected from the group consisting of C(═O), C(═S), $S(O)_m$ and $Si(R')_2$ may form a five to six membered ring, which for its part may be substituted by one or more groups selected from the group consisting of X, CN, R', OR', SR', $N(R')_2$, $Si(R')_3$, COOR', and $CON(R')_2$;

W represents O or S;

$R^4$ is selected from the group consisting of hydrogen, $C_1$-$C_8$-alkyl, cyano-$C_1$-$C_8$-alkyl $C_2$-$C_8$-alkenyl, $C_2$-$C_8$-alkynyl, $C_1$-$C_8$-haloalkyl, $C_2$-$C_8$-haloalkenyl, $C_3$-$C_8$-cycloalkyl, $C_3$-$C_8$-cycloalkyl-$C_1$-$C_8$-alkyl, $OR^{4a}$, —$C_1$-$C_6$-alkyl-$OR^{4a}$, —OC(═O)—R", —$C_1$-$C_6$-alkyl-C(═O)$C_3$-$C_6$-cycloalkyl, —$C_1$-$C_6$-alkyl-OC(═O)—R", —$C_1$-$C_6$-alkyl-N(R')C(═O)OR', —C(═O)—R" and $Si(R')_3$;

$R^{4a}$ is selected from the group consisting of hydrogen, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_3$-$C_8$-cycloalkyl, $C_3$-$C_8$-cycloalkyl-$C_1$-$C_8$-alkyl, —$C_1$-$C_6$-alkyl-$OR^{4b}$, $C_1$-$C_6$-alkyl-C(═O)$C_3$-$C_6$-cycloalkyl, —$C_1$-$C_6$-alkyl-OC(═O)—R", —$C_1$-$C_6$-alkyl-N(R')C(═O)OR', —C(═O)—R" and $Si(R')_3$;

$R^{4b}$ is selected from the group consisting of hydrogen, $C_1$-$C_8$-alkyl, $C_3$-$C_8$-cycloalkyl, $C_3$-$C_8$-cycloalkyl-$C_1$-$C_8$-alkyl, and C(═O)—R";

$R^5$ is selected from the group consisting of halogen, cyano, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, cyano-$C_1$-$C_8$-alkyl, $OR^{4a}$, $C_1$-$C_6$-alkyl-$OR^{4a}$, $C_3$-$C_8$-cycloalkyl, $C_3$-$C_8$-cycloalkyl-$C_1$-$C_8$-alkyl, $C_3$-$C_8$-halocycloalkyl, cyano-$C_3$-$C_8$-cycloalkyl, $Si(R')_3$, C(═O)—R", $S(O)_m$R', $C_1$-$C_6$-alkyl-$S(O)_m$R" and phenyl;

$R^6$ is selected from the group consisting of $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, $OR^{4a}$, $C_1$-$C_6$-alkyl-$OR^{4a}$, $C_3$-$C_8$-cycloalkyl, $C_3$-$C_8$-cycloalkyl-$C_1$-$C_8$-alkyl, $Si(R')_3$, C(═O)—R", $S(O)_m$R', and phenyl;

each group of $R^2$, $R^3$, $R^4$, $R^5$ and $R^6$ may optionally be substituted by one or more groups selected from the group consisting of halogen, CN, R", OR", SR", NR'R", $Si(R')_3$, C(═O)OR', and C(═O)NR'R";

R' is selected from the group consisting of hydrogen, $C_1$-$C_6$-alkyl, $C_2$-$C_6$-alkenyl or $C_3$-$C_8$-cycloalkyl; wherein alkyl, alkenyl and cycloalkyl groups may optionally be substituted by one or more halogen or cyano;

R" is selected from the group consisting of hydrogen, $C_1$-$C_6$-alkyl, $C_2$-$C_6$-alkenyl, $C_1$-$C_6$-haloalkyl, $C_3$-$C_8$-cycloalkyl, $N(R')_2$, OR', C(═O)R', C(═O)OR', phenyl and $C_3$-$C_6$-heterocyclyl; each group of R" may optionally be substituted by one or more groups selected from the group consisting of halogen, R', CN, OR', SR', $N(R')_2$, $Si(R')_3$, C(═O)OR' and $C(═O)N(R')_2$;

n represents integers of 0-4; and m represents integers of 0-2;

or salts, stereoisomers, metal complexes, polymorphs, or N-oxides thereof.

In one embodiment of the present invention, a compound of formula (I) is provided wherein, ring A is phenyl.

In one embodiment, the present invention provides a compound of formula (Ia) or salts thereof, Formula (Ia)

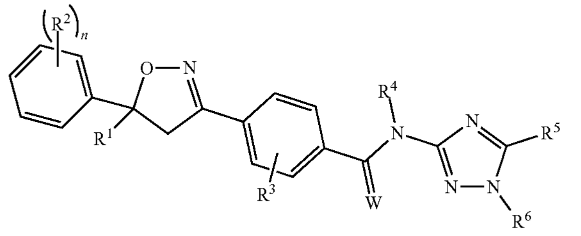

wherein, $R^1$ is selected from the group consisting of $C_1$-$C_6$-alkyl, $C_1$-$C_6$-haloalkyl, $C_3$-$C_6$-cycloalkyl and $C_3$-$C_6$-halocycloalkyl;

wherein $R^2$ is selected from the group consisting of hydrogen, halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl and $C_3$-$C_8$-cycloalkyl;

$R^3$ is selected from the group consisting of hydrogen, halogen, cyano, nitro, $C_1$-$C_4$-alkyl, $C_2$-$C_4$-alkenyl, $C_2$-$C_6$-alkynyl, $C_1$-$C_4$-haloalkyl, $C_2$-$C_4$-haloalkenyl, $C_2$-$C_6$-haloalkynyl, $C_3$-$C_4$-cycloalkyl, $C_3$-$C_8$-heterocyclyl, —$OC_3$-$C_4$-heterocyclyl, SCN, $SF_5$, NR'R", OR', $S(O)_m$R', and CR'═NR"; or two $R^3$ together with the atom to which they are attached or together with the further atoms selected from the group consisting of C, N, O, S and optionally including 1 to 3 ring members selected from the group consisting of C(═O), C(═S), $S(O)_m$ and $Si(R')_2$ may form a five to six membered ring, which for its part may be substituted by one or more groups selected from the group consisting of X, CN, R', OR', SR', $N(R')_2$, $Si(R')_3$, COOR', and $CON(R')_2$;

W represents O or S;

$R^4$ is selected from the group consisting of hydrogen, $C_1$-$C_8$-alkyl, cyano-$C_1$-$C_8$-alkyl $C_2$-$C_8$-alkenyl, $C_2$-$C_8$-alkynyl, $C_1$-$C_8$-haloalkyl, $C_2$-$C_8$-haloalkenyl, $C_3$-$C_8$-cycloalkyl, $C_3$-$C_8$-cycloalkyl-$C_1$-$C_8$-alkyl, $OR^{4a}$, —$C_1$-$C_6$-alkyl-$OR^{4a}$, —OC(═O)—R", —$C_1$-$C_6$-alkyl-C(═O)$C_3$-$C_6$-cycloalkyl, —$C_1$-$C_6$-alkyl-OC(═O)—R", —$C_1$-$C_6$-alkyl-N(R')C(═O)OR', —C(═O)—R" and $Si(R')_3$;

$R^{4a}$ is selected from the group consisting of hydrogen, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_3$-$C_8$-cycloalkyl, $C_3$-$C_8$-cycloalkyl-$C_1$-$C_8$-alkyl, —$C_1$-$C_6$-alkyl-$OR^{4b}$, $C_1$-$C_6$-alkyl-C(═O)$C_3$-$C_6$-cycloalkyl, —$C_1$-$C_6$-alkyl-OC(═O)—R", —$C_1$-$C_6$-alkyl-N(R')C(═O)OR', —C(═O)—R" and $Si(R')_3$;

$R^{4b}$ is selected from the group consisting of hydrogen, $C_1$-$C_8$-alkyl, $C_3$-$C_8$-cycloalkyl, $C_3$-$C_8$-cycloalkyl-$C_1$-$C_8$-alkyl, and C(═O)—R";

$R^5$ is selected from the group consisting of halogen, cyano, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, cyano-$C_1$-$C_8$-alkyl, $OR^{4a}$, $C_1$-$C_6$-alkyl-$OR^{4a}$, $C_3$-$C_8$-cycloalkyl, $C_3$-$C_8$-cycloalkyl-$C_1$-$C_8$-alkyl, $C_3$-$C_8$-halocycloalkyl, cyano-$C_3$-$C_8$-cycloalkyl, $Si(R')_3$, C(═O)—R", $S(O)_mR'$, $C_1$-$C_6$-alkyl-$S(O)_mR"$ and phenyl;

$R^6$ is selected from the group consisting of $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, $OR^{4a}$, $C_1$-$C_6$-alkyl-$OR^{4a}$, $C_3$-$C_8$-cycloalkyl, $C_3$-$C_8$-cycloalkyl-$C_1$-$C_8$-alkyl, $Si(R')_3$, C(═O)—R", $S(O)_mR'$, and phenyl;

each group of $R^2$, $R^3$, $R^4$, $R^5$ and $R^6$ may optionally be substituted by one or more groups selected from the group consisting of halogen, CN, R", OR", SR", NR'R", $Si(R')_3$, C(═O)OR', and C(═O)NR'R";

R' is selected from the group consisting of hydrogen, $C_1$-$C_6$-alkyl, $C_2$-$C_6$-alkenyl or $C_3$-$C_8$-cycloalkyl; wherein alkyl, alkenyl and cycloalkyl groups may optionally be substituted by one or more halogen or cyano;

R" is selected from the group consisting of hydrogen, $C_1$-$C_6$-alkyl, $C_2$-$C_6$-alkenyl, $C_1$-$C_6$-haloalkyl, $C_3$-$C_8$-cycloalkyl, $N(R')_2$, OR', C(═O)R', C(═O)OR', phenyl and $C_3$-$C_6$-heterocyclyl; each group of R" may optionally be substituted by one or more groups selected from the group consisting of halogen, R', CN, OR', SR', $N(R')_2$, $Si(R')_3$, C(═O)OR' and C(═O)$N(R')_2$;

n represents integers of 0-4; and m represents integers of 0-2;

and salts, stereo-isomers, metal complexes, polymorphs, or N-oxides thereof.

In one embodiment, the present invention provides a compound of formula (Ia) or salts thereof, wherein, the substituent $R^1$ is $C_1$-$C_4$-haloalkyl; $R^2$ is hydrogen or halogen; and the substituents $R^3$, $R^4$, $R^5$, $R^6$, W and n are as defined above.

In a preferred embodiment, the present invention provides a compound of formula (Ia-1) or salts thereof, Formula (Ia-1)

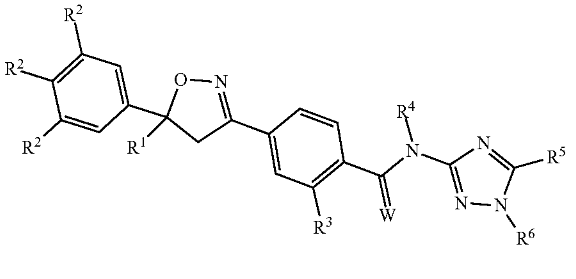

wherein, $R^1$ is $C_1$-$C_4$-haloalkyl;

$R^2$ is independently selected from hydrogen or halogen;

W is O;

$R^3$ is selected from the group consisting of hydrogen, halogen, cyano, $C_1$-$C_4$-alkyl, $C_3$-$C_4$-cycloalkyl;

$R^4$, $R^5$, $R^6$, are as defined above.

In one preferred embodiment $R^4$ is selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_3$-$C_6$-cycloalkyl, $C_3$-$C_6$-cycloalkyl-$C_1$-$C_6$-alkyl.

In one preferred embodiment $R^5$ is selected from the group consisting of halogen, cyano, $C_1$-$C_6$-alkyl, $C_2$-$C_1$-$C_6$-haloalkyl, cyano-$C_1$-$C_6$-alkyl, $OR^{4a}$, $C_1$-$C_6$-alkyl-$OR^{4a}$, $C_3$-$C_6$-cycloalkyl, $C_3$-$C_6$-cycloalkyl-$C_1$-$C_6$-alkyl, $C_3$-$C_6$-halocycloalkyl, cyano-$C_3$-$C_6$-cycloalkyl, C(═O)—R" and $C_1$-$C_6$-alkyl-$S(O)_mR"$.

In one preferred embodiment $R^6$ is selected from the group consisting of $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, $C_1$-$C_6$-alkyl-$OR^{4a}$, $C_3$-$C_8$-cycloalkyl and $C_3$-$C_8$-cycloalkyl-$C_1$-$C_8$-alkyl.

In a more preferred embodiment $R^5$ is $C_1$-$C_4$-alkyl, $C_1$-$C_4$-haloalkyl or $C_1$-$C_4$-alkyl-$C_1$-$C_4$-alkoxy; more preferably methyl ethyl, isopropyl, $CH_2F$, $CHF_2$, $CF_2CH_3$ or $CF_3$.

In a more preferred embodiment $R^6$ is $C_1$-$C_4$-alkyl, more preferably methyl, ethyl, isopropyl, $CH_2CHF_2$ or $CH_2CF_3$.

In one embodiment $C_6$-$C_{10}$ aryl is phenyl or napthalenyl, preferably phenyl.

In one preferred embodiment $R^1$ is $CF_3$.

In one preferred embodiment $R^3$ is hydrogen or methyl. More preferably methyl.

In one embodiment the preferred compounds of the general formula (I) are selected from: 4-(5-(3,5-dichloro-4-fluorophenyl)-5-(trifluoromethyl)-4,5-dihydroisoxazol-3-yl)-2-methyl-N-(1-methyl-5-(trifluoromethyl)-1H-1,2,4-triazol-3-yl)benzamide; 4-(5-(3,5-dichlorophenyl)-5-(trifluoromethyl)-4,5-dihydroisoxazol-3-yl)-2-methyl-N-(1-methyl-5-(trifluoromethyl)-1H-1,2,4-triazol-3-yl) benzamide; 4-(5-(3,5-dichloro-4-fluorophenyl)-5-(trifluoromethyl)-4,5-dihydroisoxazol-3-yl)-N-(5-ethyl-1-methyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-ethyl-1-methyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(5-ethyl-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-ethyl-1-methyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(1,5-diethyl-1H-1,2,4-triazol-3-yl)-N-ethyl-2-methylbenzamide; 4-(5-(3,5-dichlorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl) benzamide; 4-(5-(3,5-dichloro-4-fluorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)-N-(2,2,2-trifluoroethyl)benzamide; 4-(5-(3,5-dichloro-4-fluorophenyl)-5-(trifluoromethyl)-4,5-dihydroisoxazol-3-yl)-2-methyl-N-(1-methyl-5-(methylthio)-1H-1,2,4-triazol-3-yl)benzamide; 4-(5-(3,5-dichloro-4-fluorophenyl)-5-(trifluoromethyl)-4,5-dihydroisoxazol-3-yl)-N,2-dimethyl-N-(1-methyl-5-(methylthio)-1H-1,2,4-triazol-3-yl) benzamide; 4-(5-(3,5-dichloro-4-fluorophenyl)-5-(trifluoromethyl)-4,5-dihydroisoxazol-3-yl)-N-(1,5-dimethyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(1,5-dimethyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(1,5-dimethyl-1H-1,2,4-triazol-3-yl)-2-methylbenzamide; 4-(5-(3,5-dichlorophenyl)-5-(trifluoromethyl)-4,5-dihydroisoxazol-3-yl)-N-(1,5-dimethyl-1H-1,2,4-triazol-3-yl)-N,2-dimethylbenzamide; 4-(5-(3,5-dichloro-4-fluorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)benzamide; 4-(5-(3,5-dichloro-4- fluorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)-N-(2,2,2-trifluoroethyl)benzamide; N-(1-allyl-5-methyl-1H-1,2,4-triazol-3-yl)-4-(5-(3,5-dichloro-4-fluorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-2-methyl-N-(5-methyl-1-(prop-2-yn-1-yl)-1H-1,2,4-triazol-3-yl)benzamide; 4-(5-(3,5-dichloro-4-fluorophenyl)-5-(trifluoromethyl)-4,5-dihydroisoxazol-3-yl)-2-methyl-N-(1-(2,2,2-trifluoroethyl)-5-(trifluoromethyl)-1H-1,2,4-triazol-3-yl)benzamide; 4-(5-(3,5-dichloro-4-fluorophenyl)-5-(trifluoromethyl)-4,5-dihydroisoxazol-3-yl)-N-(1-ethyl-5-methyl-1H-1,2,4-triazol-3-yl)-2-methylbenzamide; N-(cyclopropylmethyl)-N-(1-(cyclopropylmethyl)-5-methyl-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichlorophenyl)-5-(trifluoromethyl)-4,5-dihydroisoxazol-3-yl)-N-ethyl-N-(1-ethyl-5-methyl-1H-1,2,4-triazol-3-yl)-2-methylbenzamide; N-allyl-N-(1-allyl-5-methyl-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichlorophenyl)-5-(trifluoromethyl)-4,5-dihydroisoxazol-3-yl)-2-methyl-N-(1-methyl-3-(trifluoromethyl)-1H-1,2,4-triazol-5-yl) benzamide; 4-(5-(3,5-dichloro-4-fluorophenyl)-5-(trifluoromethyl)-4,5-dihydroisoxazol-3-yl)-N-(5-isopropyl-1-methyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-isopropyl-1-methyl-1H-1,2,4-triazol-3-yl)-N,2-dimethylbenzamide; 4-(5-(3,5-dichloro-4-fluorophenyl)-5-(trifluoromethyl)-4,5-dihydroisoxazol-3-yl)-N-(1-ethyl-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-ethyl-5-methyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methyl-N-(2,2,2-trifluoroethyl)benzamide; N-(1-allyl-5-(trifluoromethyl)-1H-1,2,4-triazol-3-yl)-4-(5-(3,5-dichloro-4-fluorophenyl)-5-(trifluoromethyl)-4,5-dihydroisoxazol-3-yl)-2-methylbenzamide; N-(1-allyl-5-(trifluoromethyl)-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-N-(1-(2,2-difluoroethyl)-5-(trifluoromethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(2,2-difluoroethyl)-N-(1-(2,2-difluoroethyl)-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-(2,2-difluoroethyl)-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1,5-diethyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N,2-dimethyl-N-(1-methyl-5-(trifluoromethyl)-1H-1,2,4-triazol-3-yl) benzamide; N-(1-(cyanomethyl)-5-(trifluoromethyl)-1H-1,2,4-triazol-3-yl)-4-(5-(3,5-dichloro-4-fluorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-2-methyl-N-(1-methyl-5-phenyl-1H-1,2,4-triazol-3-yl)benzamide; 4-(5-(3,5-dichloro-4-fluorophenyl)-5-(trifluoromethyl)-4,5-dihydroisoxazol-3-yl)-N,2-dimethyl-N-(1-methyl-5-phenyl-1H-1,2,4-triazol-3-yl)benzamide; 4-(5-(3,5-dichloro-4-fluorophenyl)-5-(trifluoromethyl)-4,5-dihydroisoxazol-3-yl)-N-ethyl-N-(1-ethyl-5-(trifluoromethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-2-methyl-N-(1-(prop-2-yn-1-yl)-5-(trifluoromethyl)-1H-1,2,4-triazol-3-yl)benzamide; 4-(5-(3,5-dichloro-4-fluorophenyl)-5-(trifluoromethyl)-4,5-dihydroisoxazol-3-yl)-N-(5-(1,1-difluoroethyl)-1-methyl-1H-1,2,4-triazol-3-yl)-N,2-dimethylbenzamide; 4-(5-(3,5-dichloro-4-fluorophenyl)-5-(trifluoromethyl)-4,5-dihydroisoxazol-3-yl)-N-(5-(1,1-difluoroethyl)-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-methyl-1H-1,2,4-triazol-3-yl)-N,2-dimethylbenzamide; N-(1-(cyanomethyl)-5-(trifluoromethyl)-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichlorophenyl)-5-(trifluoromethyl)-4,5-dihydroisoxazol-3-yl)-2-methyl-N-(1-(2,2,2-trifluoroethyl)-5-(trifluoromethyl)-1H-1,2,4-triazol-3-yl)benzamide; 4-(5-(3,5-dichlorophenyl)-5-(trifluoromethyl)-4,5-dihydroisoxazol-3-yl)-N-(1-(2-methoxyethyl)-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-ethyl-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-(2,2,2-trifluoroethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-(1,1-difluoroethyl)-1-(2,2-difluoroethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-(2,2-difluoroethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-(1,1-difluoroethyl)-1-(2,2,2-trifluoroethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(2,2-difluoroethyl)-N-(5-(1,1-difluoroethyl)-1-(2,2-difluoroethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-(prop-2-yn-1-yl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-ethyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(1,5-diethyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(1,5-diethyl-1H-1,2,4-triazol-3-yl)-N-ethyl-2-methylbenzamide; N-(1-(cyclopropylmethyl)-5-(trifluoromethyl)-1H-1,2,4-triazol-3-yl)-4-(5-(3,5-dichloro-4-fluorophenyl)-5-

(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-2-methyl-N-(1-(2,2,3,3,3-pentafluoropropyl)-5-(trifluoromethyl)-1H-1,2,4-triazol-3-yl)benzamide; 4-(5-(3,5-dichlorophenyl)-5-(trifluoromethyl)-4,5-dihydroisoxazol-3-yl)-N-(5-(fluoromethyl)-1-methyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-(1,1-difluoroethyl)-1-(prop-2-yn-1-yl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isopropyl-1-methyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-(1,1-difluoroethyl)-1-ethyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isopropyl-1-methyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(1-(2,2-difluoroethyl)-5-isopropyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-(fluoromethyl)-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isobutyl-1-methyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-isopropyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isobutyl-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methyl-N-(2,2,2-trifluoroethyl)benzamide; 4-(5-(3,5-dichlorophenyl)-5-(trifluoromethyl)-4,5-dihydroisoxazol-3-yl)-2-methyl-N-(1-methyl-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-N-(1-ethyl-5-isopropyl-1H-1,2,4-triazol-3-yl)-2-methylbenzamide; 4-(5-(3,5-dichlorophenyl)-5-(trifluoromethyl)-4,5-dihydroisoxazol-3-yl)-2-methyl-N-(1-(2,2,2-trifluoroethyl)-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-N,2-dimethyl-N-(1-methyl-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-2-methyl-N-(2,2,2-trifluoroethyl)-N-(1-(2,2,2-trifluoroethyl)-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-2-methyl-N-(1-methyl-5-(2,2,2-trifluoroethyl)-1H-1,2,4-triazol-3-yl)benzamide; 4-(5-(3,5-dichlorophenyl)-5-(trifluoromethyl)-4,5-dihydroisoxazol-3-yl)-N-(1-(2,2-difluoroethyl)-5-(3,3,3-trifluoropropyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-ethyl-5-(3,3,3-trifluoropropyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-(3,3,3-trifluoropropyl)-1H-1,2,4-triazol-3-yl)-2-methylbenzamide; 4-(5-(3,5-dichlorophenyl)-5-(trifluoromethyl)-4,5-dihydroisoxazol-3-yl)-2-methyl-N-(1-(prop-2-yn-1-yl)-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-2-methyl-N-(prop-2-yn-1-yl)-N-(1-(prop-2-yn-1-yl)-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-N-(5-isopropyl-1-(prop-2-yn-1-yl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isopropyl-1-(prop-2-yn-1-yl)-1H-1,2,4-triazol-3-yl)-2-methyl-N-(prop-2-yn-1-yl)benzamide; N-(1-allyl-5-(3,3,3-trifluoropropyl)-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichlorophenyl)-5-(trifluoromethyl)-4,5-dihydroisoxazol-3-yl)-N-(5-(methoxymethyl)-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(methoxymethyl)-1-methyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(5-(methoxymethyl)-1-(2,2,2-trifluoroethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-ethyl-5-(methoxymethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(methoxymethyl)-1-(2,2,2-trifluoroethyl)-1H-1,2,4-triazol-3-yl)-2-methyl-N-(2,2,2-trifluoroethyl)benzamide; 4-(5-(3,5-dichlorophenyl)-5-(trifluoromethyl)-4,5-dihydroisoxazol-3-yl)-N-ethyl-N-(1-ethyl-5-(methoxymethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-(2,2-difluoroethyl)-5-(methoxymethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(methoxymethyl)-1-(prop-2-yn-1-yl)-1H-1,2,4-triazol-3-yl)-2-methylbenzamide; 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-(methoxymethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(methoxymethyl)-1-(prop-2-yn-1-yl)-1H-1,2,4-triazol-3-yl)-2-methyl-N-(prop-2-yn-1-yl)benzamide; N-(1-allyl-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide; N-(1-(cyanomethyl)-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide; N-(cyanomethyl)-N-(1-(cyanomethyl)-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide; N-allyl-N-(1-allyl-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-2-methyl-N-(1-(2,2,2-trifluoroethyl)-5-(3,3,3-trifluoropropyl)-1H-1,2,4-triazol-3-yl)benzamide; 4-(5-(3,5-dichloro-4-fluorophenyl)-5-(trifluoromethyl)-4,5-dihydroisoxazol-3-yl)-2-methyl-N-(1-methyl-5-(3,3,3-trifluoropropyl)-1H-1,2,4-triazol-3-yl)benzamide; 4-(5-(3,5-dichloro-4-fluorophenyl)-5-(trifluoromethyl)-4,5-dihydroisoxazol-3-yl)-N,2-dimethyl-N-(1-methyl-5-(3,3,3-trifluoropropyl)-1H-1,2,4-triazol-3-yl)benzamide; 4-(5-(3,5- dichloro-4-fluorophenyl)-5-(trifluoromethyl)-4,5-dihydroisoxazol-3-yl)-2-methyl-N-(2,2,2-trifluoroethyl)-N-(1-(2,2,2-trifluoroethyl)-5-(3,3,3-trifluoropropyl)-1H-1,2,4-triazol-3-yl)benzamide; N-(1-(cyanomethyl)-5-(3,3,3-trifluoropropyl)-1H-1,2,4-triazol-3-yl)-4-(5-(3,5-dichlorophenyl)-5-(trifluoromethyl)-4,5-dihydroisoxazol-3-yl)-2-methylbenzamide; N-(cyanomethyl)-N-(1-(cyanomethyl)-5-(3,3,3-trifluoropropyl)-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-N-(1-(2,2-difluoroethyl)-5-(3,3,3-trifluoropropyl)-1H-1,2,4-triazol-3-yl)-2-methylbenzamide and 4-(5-(3,5-dichloro-4-fluorophenyl)-5-(trifluoromethyl)-4,5-dihydroisoxazol-3-yl)-2-methyl-N-(prop-2-yn-1-yl)-N-(1-(prop-2-yn-1-yl)-5-(3,3,3-trifluoropropyl)-1H-1,2,4-triazol-3-yl)benzamide;

The compounds of the present invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomers) or when separated from the other stereoisomer(s). Additionally, the skilled artisan knows how to separate, enrich, and/or to selectively prepare said stereoisomers. The compounds of the present invention may be present as a mixture of stereoisomers, individual stereoisomers or as an optically active form.

An anion part of the salt in case the compound of formula (I) is a cationic or capable of forming a cation can be inorganic or organic. Alternatively, a cation part of the salt in case the compound of formula (I) is an anionic or capable of forming anion can be inorganic or organic. Examples of inorganic anion part of the salt include but are not limited to chloride, bromide, iodide, fluoride, sulfate, phosphate, nitrate, nitrite, hydrogen carbonates and hydrogen sulfate. Examples of organic anion part of the salt include but are not limited to formate, alkanoates, carbonates, acetates, trifluoroacetate, trichloroacetate, propionate, glycolate, thiocyanate, lactate, succinate, malate, citrates, benzoates, cinnamates, oxalates, alkylsulphates, alkylsulphonates, arylsulphonates aryldisulphonates, alkylphosphonates, arylphosphonates, aryldiphosphonates, p-toluenesulphonate, and salicylate. Examples of inorganic cation part of the salt include but are not limited to alkali and alkaline earth metals. Examples of organic cation part of the salt include but are not limited to pyridine, methyl amine, imidazole, benzimidazole, hitidine, phosphazene, tetramethyl ammonium, tetrabutylammonium, choline and trimethylamine.

Metal ions in metal complexes of the compound of formula (I) are especially ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period and the first to eighth transition groups. Here, the metals can be present in the various valencies that they can assume.

In one embodiment, the present invention provides a compound of formula (I), agriculturally acceptable salts, metal complexes, constitutional isomers, stereo-isomers, diastereoisomers, enantiomers, chiral isomers, atropisomers, conformers, rotamers, tautomers, optical isomers, polymorphs, geometric isomers, or N-oxides thereof and its compositions with the excipient, inert carrier or any other essential ingredient such as surfactants, additives, solid diluents and liquid diluents. Salts of the compounds of the formula (I) are preferably veterinary and/or agriculturally acceptable salts, preferably agriculturally acceptable salts. They can be formed in a customary manner, e.g. by reacting the compound with an acid of the anion in question if the compound of formula (I) has a basic functionality.

The term "N-oxide" includes any compound of formula (I) which has at least one tertiary nitrogen atom that is oxidized to an N-oxide moiety.

The compounds of formula (I), including all stereoisomers, N-oxides, and salts thereof, typically exist in more than one form, and formula (I) thus includes all crystalline and non-crystalline forms of the compounds that formula (I) represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by formula (I) can exhibit beneficial effects (e.g., suitability for preparation of useful formulations, improved biological performance) relative to another polymorph or a mixture of polymorphs of the same compound represented by formula (I). Preparation and isolation of a particular polymorph of a compound represented by formula (I) can be achieved by methods known to those skilled in the art including, for example, crystallization using selected solvents and temperatures.

In one embodiment, the present invention provides a process for preparing the compound of formula (I) or agriculturally acceptable salts, Formula (I)

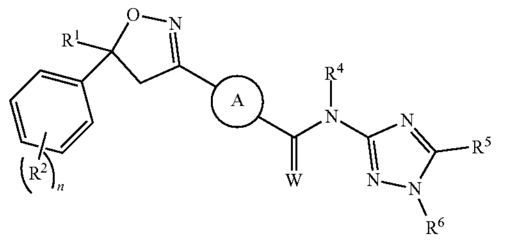

The compounds of the present invention as defined by formula (I) and/or in table (I) may be prepared, in known manner, in a variety of ways as described in the following schemes. Compounds of the present invention can be made as shown in the following schemes, in which, unless otherwise stated, the definition of each R group substitution is as defined above for a compound of formula (I).

General Synthetic Schemes

Scheme 1

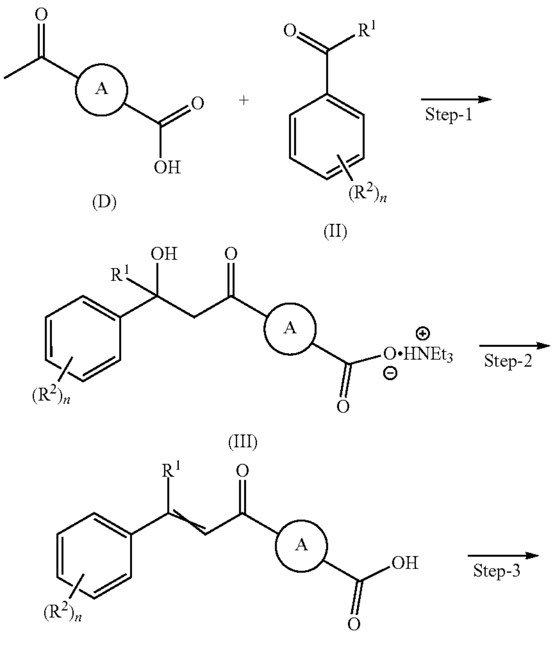

(D) (II) (III) (IV)

-continued

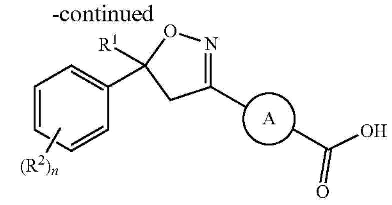

(V)

Compounds of formula (V) can be prepared starting from compounds of formula (D) and (II) according to similar methods described in WO2009001942 and as shown in Scheme 1.

Compounds of formula (III) can be prepared by reacting compounds of formula (I) with ketones of formula (II) in the presence of a base such as triethyl amine and a solvent such as toluene.

In addition, compounds of formula (IV) can be prepared from compounds of formula (III) by dehydration in the presence of acetic anhydride or another appropriate carboxylic acid anhydride and 4-dimethylaminopyridine or another appropriate base.

Compounds of formula (V) can be accessed from compounds of formula (IV) by treatment with hydroxyl amine (for instanced utilized as a 50% aqueous solution) and a phase transfer catalyst such as tetrabutylammonium bromide in a suitable biphasic solvent system such as toluene and water.

Scheme-2

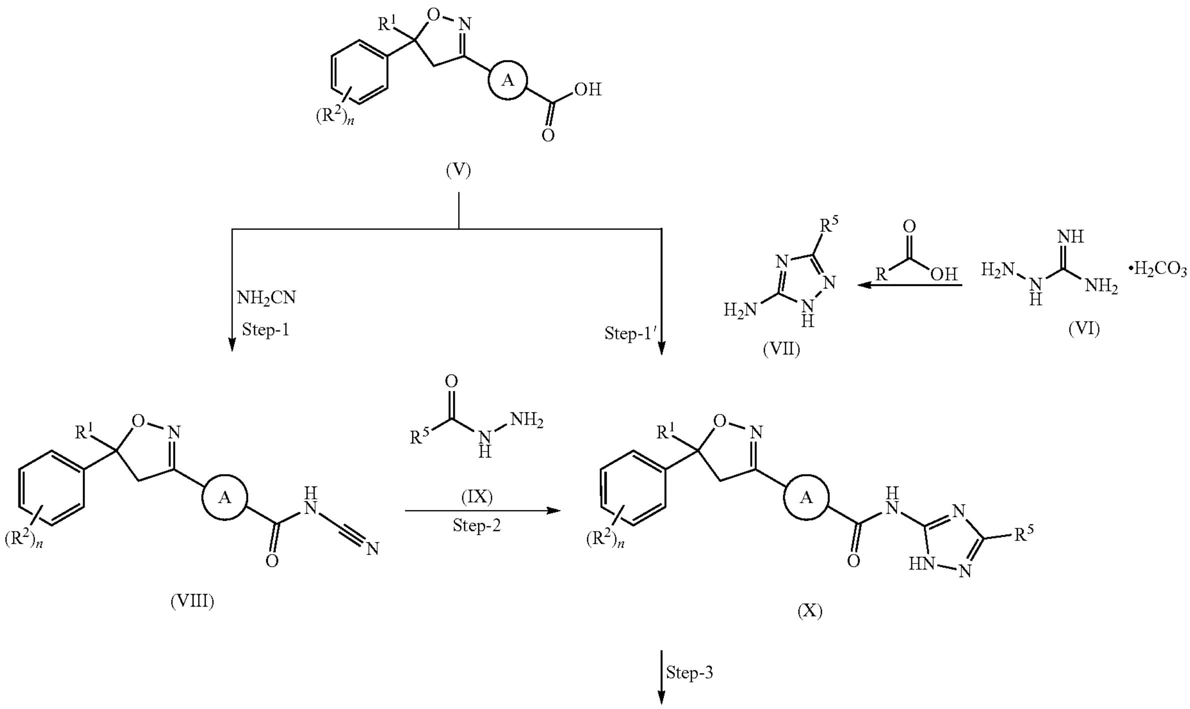

(V) (VI) (VII) (VIII) (IX) (X)

-continued

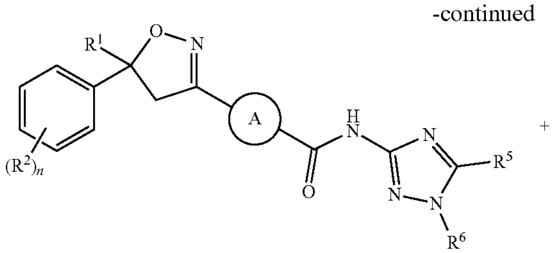

(I)

+

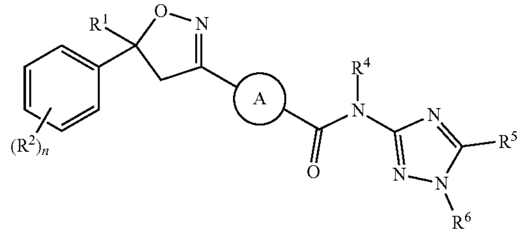

(I)

Compounds of formula (I) can be prepared via different routes from intermediates of formula (X), starting from compounds of formula (V) according to the method shown in Scheme 2.

Compounds of type (VIII) can be prepared according to identical methods described for example in WO2008154528 and WO2018184019, by reacting compounds of type (V) with cyanamide in an organic solvent and in the presence of an amide coupling reagent such as 1-[bis(dimethylamino)methylene]-1H-1,2,3-triazolo[4,5-b]pyridinium 3-oxide hexafluorophosphate (HATU), 3-[bis(dimethylamino)methyliumyl]-3H-benzotriazol-1-oxide hexafluorophosphate (HBTU), N,N'-dicyclohexylcarbodiimide (DCC), 1-ethyl-3-(3-dimethylamino-propyl)carbodiimide hydrochloride (EDC) or bis(2-oxo-3-oxazolidinyl)phosphonic chloride (BOP-Cl), and optionally in the presence of a nucleophilic catalyst such as hydroxybenzotriazole (HOBT), in the presence of a base such as N,N-diisopropylethylamine (DIPEA).

Compounds of type (X) may be accessed as described for example in *Russian Chemical Bulletin, International Edition*, Vol. 64, No. 5, 2015, 1089-1092, by reacting compounds of type (VIII) with monoacetyl hydrazine in the presence of a metal catalyst such as acetylacetone nickel in an anhydrous solvent such as dioxane, under reflux condition.

Alternatively, compounds of type (X) can be accessed by methods as described in (WO2005085216), directly by reacting compounds of type (V) with compounds of type (VII).

Compounds of the type (VII) can be prepared from aminoguanidine hydrogencarbonate (VI) and corresponding carboxylic acids as described for example in *European Journal of Medicinal Chemistry,* 156, 2018, 774-789, in the presence of an amide coupling reagent such as 1-[bis(dimethylamino)methylene]-1H-1,2,3-triazolo[4,5-b]pyridinium 3-oxide hexafluorophosphate (HATU), 3-[bis(dimethylamino)methyliumyl]-3H-benzotriazol-1-oxide hexafluorophosphate (HBTU), N,N'-dicyclohexylcarbodiimide (DCC), 1-ethyl-3-(3-dimethylamino-propyl)carbodiimide hydrochloride (EDC) or bis(2-oxo-3-oxazolidinyl)phosphonic chloride (BOP-Cl) and optionally in the presence of a nucleophilic catalyst such as hydroxybenzotriazole (HOBT), in the presence of a base such as N,N-diisopropylethylamine (DIPEA).

Compounds of formula (XI) and (XII) can be synthesized by alkylating triazole amine derivative of type (X) with alkylating agents such as alkyl halides, methyl bromide, ethyl bromide, propyl bromide, methyl iodide, ethyl iodide, and propyl iodide; dialkyl sulfates such as dimethyl sulfate, diethyl sulfate, and di-n-propyl sulfate; and sulfonic acid esters such as methyl p-toluenesulfonate, ethyl p-toluenesulfonate, n-propyl p-toluenesulfonate, methyl methanesulfonate, ethyl methanesulfonate, and propyl methanesulfonate, alkyl triflates, or dialkyl carbonates in the presence of a suitable base.

Scheme-3

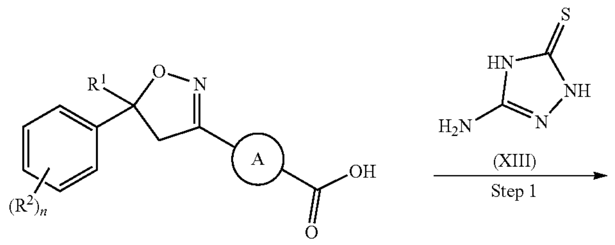

(V)

-continued

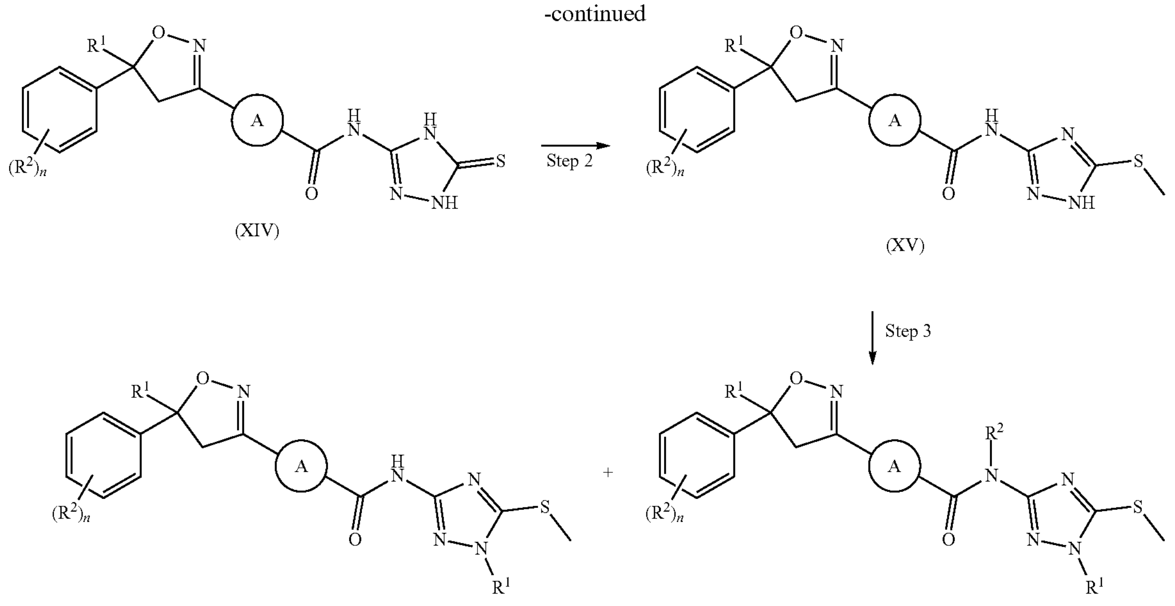

(XIV) (XV) (I) (I)

Compounds of formula (I) can be derived from appropriate acid derivatives (V) and amines of type (XIII) followed by S-alkylation of the amide intermediate (XIV), and further alkylation as shown in Scheme 3.

In one embodiment, amide intermediates (XIV) can be accessed by acylation of the appropriate amines (XIII) with compounds (V) in the presence of amide coupling reagents such as 1-[bis(dimethylamino)methylene]-1H-1,2,3-triazolo [4,5-b]pyridinium 3-oxide hexafluorophosphate (HATU), 3-[bis(dimethylamino)methyliumyl]-3H-benzotriazol-1-oxide hexafluorophosphate (HBTU), N,N'-dicyclohexylcarbodiimide (DCC), 1-ethyl-3-(3-dimethylamino-propyl)carbodiimide hydrochloride (EDC) or bis(2-oxo-3-oxazolidinyl) phosphonic chloride (BOP-Cl) and optionally in the presence of a nucleophilic catalyst such as hydroxybenzotriazole (HOBT), in the presence of a base such as N,N-diisopropylethylamine (DIPEA).

In another embodiment, compounds of formula (XV) can be synthesized by S-alkylation of compounds of type (XIV) using alkylating agents such as alkyl halides, alkyl triflates, dimethyl sulphate or dimethyl carbonate in the presence of a suitable base such as sodium hydroxide. Subsequent N-alkylation of (XV) can be achieved by the use of an alkylating agent such as idomethane in the presence of a suitable base such as sodium hydride, giving compounds of formula (XVI), potentially as a mixtures with the regioisomer (XVII) as a side-product.

Depending on the nature of the substituents, the compounds of formula (I) and intermidiates thereof may be present either in pure form or as mixtures of different possible isomeric forms such as stereoisomers or constitutional isomers. The various stereoisomers include enantiomers, diastereomers, chiral isomers, atropisomers, conformers, rotamers, tautomers, optical isomers, polymorphs, and geometric isomers.

Depending on the nature of the substituents, the compounds of formula (I) and intermidiates thereof as mentioned in the general schemes can also exist in one or more geometric isomer forms depending on the relative position (syn/anti or cis/trans) of the substituents. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

In another embodiment, the present invention provides a process for the preparation of compounds of formula (I) or of salts thereof.

In another embodiment, the present invention provides a method for preparing compounds of formula (I), comprising the steps of:

a) reacting a compound of formula (V) with a compound of formula (VII) in the presence of suitable reagents and solvents to obtain a compound of formula (X) according to the reaction scheme as depicted below:

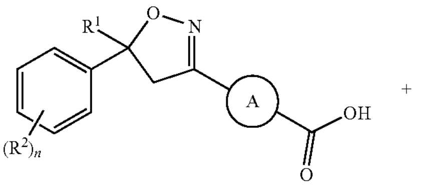

(V)

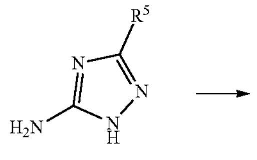

(VII)

-continued

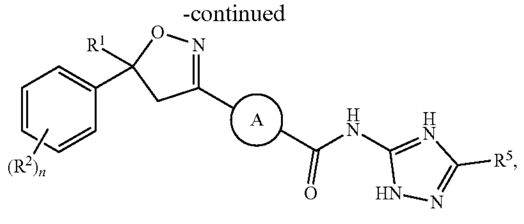

(X)

wherein, $R^1$, $R^2$, $R^5$, A and n are as defined in the detailed description;

b) optionally, a compound of formula (X) can be obtained by converting a compound of formula (V) to a compound of formula (VIII) and further converting it to a compound of formula (X) in the presence of suitable reagents and solvents, according to the reaction scheme as depicted below:

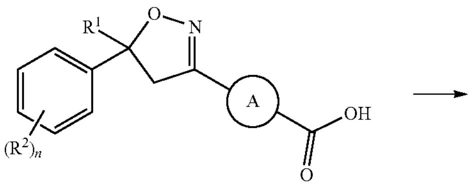

(V)

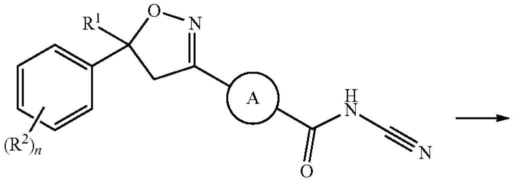

(VIII)

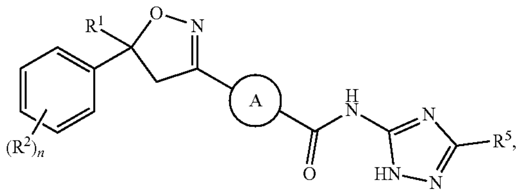

(X)

wherein, $R^1$, $R^2$, $R^5$, A and n are as defined in the detailed description;

c) further, a compound of formula (I) can be obtained by converting a compound of formula (X) to a compound of formula (I) in the presence of suitable reagents and solvents according to the reaction scheme as depicted below:

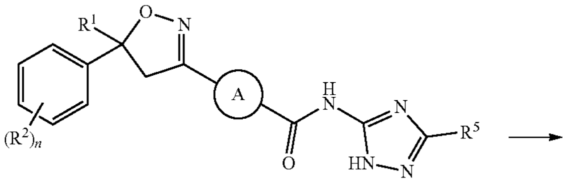

(X)

-continued

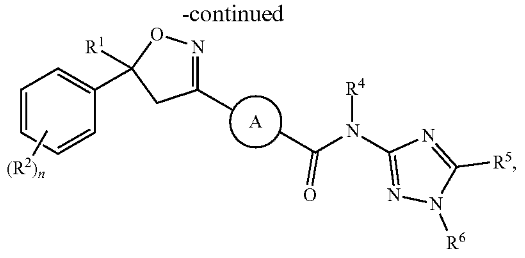

(I)

wherein, $R^1$, $R^2$, $R^4$, $R^5$, $R^6$, A and n are as defined in the detailed description.

The compounds of formula (I) including their stereoisomers, salts, and N-oxides, and their precursors in the synthesis process, can be prepared by the methods described above. If individual compounds can not be prepared via the above-described routes, they can be prepared by derivatization of other compounds of formula (I) or the respective precursors, or by customary modifications of the described synthetic routes. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the described synthetic routes.

The reaction mixtures are worked up in a customary manner, e.g. by mixing with water, separating the phases and, if appropriate, chromatographic purification of the crude products. Some of the intermediates and end products are obtained in the form of colourless or slightly coloured viscous oils which are purified or freed from volatile components under reduced pressure and at moderately elevated temperature. If the intermediates and end products are obtained as solids, purification can also be carried out by recrystallization or digestion.

If individual compounds (I) cannot be obtained by the routes described above, they can be prepared by derivatization of other compounds of formula (I). However, if the respective synthesis yields mixtures of isomers, a separation is generally not necessarily required since in some cases the individual isomers can be interconverted during work-up for use or during application (e.g. under the action of light, radical generating reagents, acids or bases). Such conversions may also take place after use, e.g. in the treatment of plants in the treated plant, or in the harmful fungus to be controlled.

In one embodiment, the present invention provides a composition for controlling or preventing invertebrate pests. The composition comprises a biologically effective amount of the compound of formula (I) agriculturally acceptable salts, isomers/structural isomers, stereo-isomers, diastereomers, enantiomers, tautomers, metal complexes, polymorphs, or N-oxides thereof and at least one additional component selected from the group consisting of surfactants and auxiliaries.

In yet another embodiment, the composition additionally comprises at least one additional biologically active and compatible compound selected from fungicides, insecticides, nematicides, acaricides, biopesticides, herbicides, plant growth regulators, antibiotics, fertilizers or nutrients.

In yet another embodiment, the present invention provides a compound of formula (I) or its N-oxides and salts into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, "Formulation Technology", Wiley VCH, Weinheim, 2001; or Knowles, "New Developments in Crop Protection Product Formulation", Agrow Reports DS243, T and F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers or binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; dimethyl sulfoxide; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers and Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugarbased surfactants are sorbitans, ethoxylated sorbitans, sucrose and glucose esters or alkylpolyglucosides. Examples of polymeric surfactants are homeor copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetaines and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, "Adjuvants and Additives", Agrow Reports DS256, TandF Informa UK, 2006, chapter 5.

Suitable thickeners are polysaccharides (e.g. xanthan gum, carboxymethylcellulose), anorganic clays (organically modified or unmodified), polycarboxylates, and silicates. Suitable bactericides are bronopol and isothiazolinone derivatives such as alkylisothiazolinones and benzisothiazolinones. Suitable anti-freezing agents are ethylene glycol, propylene glycol, urea and glycerin. Suitable anti-foaming agents are silicones, long chain alcohols, and salts of fatty acids. Suitable colorants (e.g. in red, blue, or green) are pigments of low water solubility and watersoluble dyes. Examples are inorganic colorants (e.g. iron oxide, titan oxide, iron hexacyanoferrate) and organic colorants (e.g. alizarin-, azoand phthalocyanine colorants). Suitable tackifiers or binders are polyvinylpyrrolidone, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound (I) or an N-oxide or salt thereof and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)

5-25 wt % of a compound (I) or an N-oxide or salt thereof and 1-10 wt % dispersant (e. g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of a compound I or an N-oxide or salt thereof and 5-10 wt % emulsifiers (e.g. calcium dodecylbenzenesulfonate and castor oil ethoxylate) are dissolved in up to 100 wt % water insoluble organic solvent (e.g. aromatic hydrocarbon). Dilution with water gives an emulsion.

iv) Emulsions (EW, EO, ES)

5-40 wt % of a compound (I) or an N-oxide or salt thereof and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound (I) or an N-oxide or salt thereof are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound (I) or an N-oxide or salt thereof are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound (I) or an N-oxide or salt thereof are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound (I) or an N-oxide or salt thereof are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance, ix) Microemulsion (ME)

5-20 wt % of a compound (I) or an N-oxide or salt thereof are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

x) Microcapsules (CS)

An oil phase comprising 5-50 wt % of a compound I or an N-oxide or salt thereof, 0-40 wt % water insoluble organic solvent (e.g. aromatic hydrocarbon), 2-15 wt % acrylic monomers (e.g. methylmethacrylate, methacrylic acid and a dior triacrylate) are dispersed into an aqueous solution of a protective colloid (e.g. polyvinyl alcohol). Radical polymerization initiated by a radical initiator results in the formation of poly(methyl acrylate) microcapsules. Alternatively, an oil phase comprising 5-50 wt % of a compound (I) according to the present invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition, xi) Dustable Powders (DP, DS)

1-10 wt % of a compound I or an N-oxide or salt thereof are ground finely and mixed intimately with up to 100 wt % solid carrier, e.g. finely divided kaolin.

xii) Granules (GR, FG)

0.5-30 wt % of a compound I or an N-oxide or salt thereof is ground finely and associated with up to 100 wt % solid carrier (e.g. silicate). Granulation is achieved by extrusion, spray-drying or the fluidized bed.

xiii) Ultra-Low Volume Liquids (UL)

1-50 wt % of a compound I or an N-oxide or salt thereof are dissolved in up to 100 wt % organic solvent, e.g. aromatic hydrocarbon.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

In one another embodiment, the present invention provides an agrochemical composition comprising compounds of formula (I), which contains this active substance between 0.01 and 95% by weight, preferably between 0.1 and 90%, and more preferably between 1 and 70%, in particular between 10 and 60 by weight. The respective active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purpose of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying compounds of formula (I) and compositions thereof, respectively, on to plant propagation material, especially seeds, include dressing, coating, pelleting, dusting, soaking and in-furrow application methods of the propagation material. Preferably, the compound of formula (I) or the compositions thereof, respectively, are applied on to the plant propagation material by in such a way, that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.02 to 0.9 kg per ha, in particular from 0.05 to 0.75 kg per ha.

In treatment of plant propagation materials such as seeds, e. g. by dusting, coating or drenching seed, amounts of active substance of 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetteners, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the present invention in a weight ratio of 1:100 to 100:1, preferably 1:10 to 10:1.

The user can apply the composition according to the present invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the present invention is thus obtained. Usually, 20 to 6000 liters, preferably 35 to 1000 litres, more preferably 50 to 500 liters, of the ready-to-use spray liquor are applied per hectare of the agricultural useful area.

According to one embodiment, individual components of the composition according to the present invention such as parts of a kit or parts of a binary or ternary mixture may be mixed by the user himself in a spray tank and further auxiliaries may be added, if appropriate.

The compounds and compositions of the present invention are thus agronomically useful for protecting field crops from phytophagous invertebrate pests, and also nonagronomically useful for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits.

The compounds of the present invention are characterized by favorable metabolic and/or soil residual patterns and exhibit activity controlling a spectrum of agronomic and non-agronomic invertebrate pests. The compounds of the present invention are preventively and/or curatively valuable active ingredients in the field of pest control, even at low rates of application, which can be used against insecticide resistant pests such as insects and mites, and are well tolerated by warm-blooded species, fish and plants.

In the context of the present invention "invertebrate pest control" means inhibition of invertebrate pest development (including mortality) that causes significant reduction in feeding or other injury or damage caused by the pest; related expressions are defined analogously. As referred to in the present invention, the term "invertebrate pest" includes arthropods, gastropods and nematodes of economic importance as pests. The term "arthropod" includes insects, mites, spiders, scorpions, centipedes, millipedes, pill bugs and symphylans.

The term "gastropod" includes snails, slugs and other stylommatophora. The term "nematode" includes all of the helminths, such as: roundworms, heartworms, and phytophagous nematodes (Nematoda), flukes (Trematoda), acanthocephala, and tapeworms (Cestoda). Those skilled in the art will recognize that not all compounds are equally effective against all pests.

The compounds of the present invention display activity against economically important agronomic, forest, greenhouse, nursery, ornamentals, turfgrass, food and fiber, public and animal health, domestic and commercial structure, household, and stored product pests. These include larvae of the order Lepidoptera, such as armyworms, cutworms, loopers, and heliothines in the family Noctuidae (e.g., fall armyworm (*Spodoptera frugiperda* J. E. Smith), beet armyworm (*Spodoptera exigua* Hubner), black cutworm (*Agrotis ipsilon* Hufnagel), cabbage looper (*Trichoplusia ni* Hubner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hubner), navel orangeworm (*Amyelois transitella* Walker), corn root webworm (*Crambus caliginosellus* Clemens), sod webworm (*Herpetogramma licarsisalis* Walker)); leafrohers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blattella asahinai* Mizukubo), German cockroach (*Blattella gemnanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition it includes: adults and larvae of the order Dermaptera including earwigs from the family Forficulidae (e.g., European earwig (*Forficula auricularia* Linnaeus), black earwig (*Chelisoches mono* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whitefiies from the family Aleyrodidae, aphids from the family Aphididae, *Phylloxera* from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chiysomya* spp., *Phonnia* spp.), and other muscoid fly pests, horse flies (e.g., *Tabanus* spp.), botflies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion *thrips* (*Thrips tabaci* Lindeman) and other foliar feeding *thrips*; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* FBrster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus* capitis De Geer), body louse (*Pediculus humanus humanus* Linnaeus), chicken body louse (*Menacanthus stramineus* Nitszch), dog biting louse (*Trichodectes* cams De Geer), fluff louse (*Goniocotes gallinae* De Geer), sheep body louse (*Bovicola ovis* Schrank), short-nosed cattle louse (*Haematopinus eurystemus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (Ctenocephatides *canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch and Mulaik) and the black widow spider (*Latrodectus mactans* Fabricius), and centipedes in the order Scutigeromorpha such as the house centipede (*Scutigera coleoptrata* Linnaeus). Activity also includes members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala* peifoliata in horses, *Fasciola hepatica* Linnaeus in ruminants, etc.).

The compounds of the present invention show particularly high activity against pests of the order of Lepidoptera (e.g., *Alabama argillacea* Hubner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoveipa armigera* Hubner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis and Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hubner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tula absoluta* Meyrick (tomato leafminer)).

Compounds of the present invention also have commercially significant activity on members from the order Homoptera including: *Acyrthisiplionpisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii*, Boyer de Fonscolombe (black citrus aphid), and *Toxoptera citiicida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows and Perring (silverleaf whitefly), *Dialeurodes citri* Ashmead (citrus whitefly) and *Trialeurodes vaporariorum* Westwood (greenhouse whitefly); *Empoasca fabae* Harris, (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stal (rice leafhopper), *Nilaparvata lugens* Stal (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAfee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); Pseudococcus spp. (other mealybug complex); *Cacopsylla pyricola* Foerster (pear *psylla*), *Trioza diospyri* Ashmead (persimmon *psylla*).

These compounds also have activity on members from the order Hemiptera including: *Acrostemum hilare* Say (green stink bug), *Amrasca biguttulla biguttulla* (cotton jassid) *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-S chaffer (cotton stainer), *Euchistus servus* Say (brown stink bug), *Euchistus variolrius* Palisot deBeauvois (one-spotted stink bug), *Graptósthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* DaEas (large milkweed bug), *Pseudatomoscelis seriatus* Reuter (cotton fleahopper).

Other insects which are controlled by compounds of formula (I) of the present invention include: Thysanoptera (e.g., *Frankliniella occidentalis* Pergande (western flower thrip), *Scirthothrips citri* Moulton (citrus thrip), *Sericothrips variabilis* Beach (soybean thrip), *Scirtothrips dorsalis* (chilli *thrips* or yellow tea *thrips*) and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Particularly, the compounds of formula (I), their N-oxides, their isomers, their polymorphs and their salts are especially suitable for efficiently combating the following pests: Insects from the order of the lepidopterans (Lepidoptera), for example *Agrotis ipsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Chilo infuscatellus, Choristoneura fumiferana, Choristoneura occidentalis, Cirphis unipuncta, Cydia pomonella, Dendrolimus pini, Diaphania nitidalis, Diatraea grandiosella, Earias insulana, Earias vittella, Elasmopalpus lignosellus, Eupoecilia ambiguella, Evetria bouliana, Feltia subterranea, Galleria mellonella, Grapholita funebrana, Grapholita molesta, Helicoverpa armigera, Helicoverpa virescens, Helicoverpa zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Leucinodes orbonalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scirpophaga incertulas, Scrobipalpula absoluta, Sitotroga cerealella, Sparganothis pilleriana, Spodoptera frugiperda, Spodoptera littoralis, Spodoptera litura, Spodoptera exigua, Thaumatopoea pityocampa, Tortrix viridana, Trichoplusia ni* and *Zeiraphera canadensis*; and Beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica undecimpunctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria*; flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus,*

*Tabanus atratus, Tabanus lineola*, and *Tabanus similis, Tipula oleracea*, and *Tipula paludosa*; termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis*, and *Coptotermes formosanus*; cockroaches (*Blattaria* Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*; ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus*, and *Linepithema humile*; crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera*, and *Locustana pardalina; Araneida*, e.g. *Latrodectus mactans*, and *Loxosceles reclusa*; fleas (*Siphonaptera*), e.g. *Ctenocephalides felis, Ctenocephalides canis, Xenopsylla cheopis, Pulex irritans, Tunga penetrans*, and *Nosopsyllus fasciatus*, silverfish, firebrat (Thysanura), e.g. *Lepisma saccharina* and *Thermobia domestica*, centipedes (Chilopoda), e.g. *Scutigera oleoptrata*, millipedes (Diplopoda), e.g. *Narceus* spp., Earwigs (Dermaptera), e.g. *Forficula auricularia*, lice (Phthiraptera), e.g. *Pediculus humanus capitis, Pediculus humanus* corporis, *Pthirus pubis, Haematopinus eurysternus, Haematopinus suis, Linognathus vituli, Bovicola bovis, Menopon allinae, Menacanthus stramineus* and *Solenopotes capillatus*. Collembola (springtails), e.g. *Onychiurus* ssp.

The compounds of formula (I) of the present invention are also suitable for controlling Nematodes: plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of formula (I) and their salts are also useful for controlling arachnids (*Arachnoidea*), such as acarians (*Acarina*), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei*, and Eriophyidae spp. such as *Aculus schlechtendali, Phyllocoptrata oleivora* and *Eriophyes sheldoni*; Tarsonemidae spp. such as *Phytonemus pallidus* and *Polyphagotarsonemus latus*; Tenuipalpidae spp. such as *Brevipalpus phoenicis*; Tetranychidae spp. such as *Tetranychus cinnabarinus, Tetranychus kanzawai, Tetranychus pacificus, Tetranychus telarius* and *Tetranychus urticae, Panonychus ulmi, Panonychus citri*, and *Oligonychus pratensis*.

In one embodiment of the present invention, the present invention provides the compound of formula (I) which is useful for controlling insects selected form sucking or piercing insects such as insects from the genera Thysanoptera, Diptera and Hemiptera, in particular the following species:

Thysanoptera: *Frankliniella fusca, Frankliniella occidentalis, Frankliniella tritici, Scirtothrips citri, Scirtothrips dorsalis, Thrips oryzae, Thrips palmi* and *Thrips tabaci*, Diptera: *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza fiorum, Oscinella frit, Pegomya hysocyami, Phorbia antiqua, Phorbia brassicae, Phorbia coarctata, Phlebotomus argentipes, Psorophora columbiae,*

*Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola*, and *Tabanus similis, Tipula oleracea*, and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mail, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand*, and *Viteus vitifolii.*

In one embodiment, the present invention compound of formula (I) is useful for controlling for controlling insects/mites of the orders *Acarina*, Coleoptera, Diptera, Hymenoptera, Isoptera, Lepidoptera, Hemiptera, Orthoptera, and Thysanoptera.

In one preferred embodiment, the present invention compound of formula (I) is useful for controlling *Helicoveipa armigera, Plutella xylostella, Spodoptera frugiperdd, Spodoptera litura, Frankliniella occidentalis, Scirtothrips dorsalis, Trichoplusia ni* Hubner, *Empoasca fabae, Aphis gossypii, Myzus persicae, Amrasca biguttulla biguttulla, Nilaparvata lugens, Bemisia tabaci* and *Tetranychus urticae.*

In one embodiment, the present invention provides a composition comprising a biologically effective amount of the compound of formula (I) and at least one additional biological active compatible compound selected from fungicides, insecticides, nematicides, acaricides, biopesticides, herbicides, plant growth regulators, antibiotics, fertilizers and nutrients. The compounds used in the composition and in combination with the compound of formula (I) are also termed as active compatible compounds.

The known and reported fungicides, insecticides, nematicides, acaricides, biopesticides, herbicides, plant growth regulators, antibiotics and nutrients can be combined with at least one compound of the formula (I) of the present disclosure. For example, fungicides, insecticides, nematicides, acaricides, biopesticides, herbicides, plant growth regulators, antibiotics, fertilizers and nutrients disclosed and reported in WO2016156129 and/or WO2017153200 can be combined with at least one compound of formula (I) of the present disclosure.

The fungicides, insecticides, nematicides, acaricides, biopesticides, herbicides, plant growth regulators, antibiotics, fertilizers and nutrients reported in WO2016156129 and or WO2017153200 are incorporated herein by way of reference as non-limiting examples to be combined with at least one compound of the formula (I) of the present disclosure.

Particularly, the compounds of the present invention can be mixed with at least one additional biological active compatible compound (mixing partner) which includes but is not limited to insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility.

Examples of such biologically active compounds or agents/mixing partners with which compound of formula (I) of the present invention can be combined/formulated are disclosed in the WO2019072906A1 (page 27 to 37).

In one embodiment, the biological agents for mixing with compounds of the present invention include *Bacillus thuringiensis, Bacillus thuringiensis* delta endotoxin as well as naturally occurring and genetically modified viral insecticides including members of the family Baculoviridae as well as entomophagous fungi.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of the invention can also provide a broader spectrum of plant protection and be advantageous for resistance management.

In one embodiment of the present invention, the biologically effective amount of the compound of formula (I) in the compositions ranges from 0.1% to 99% by weight with respect to the total weight of the composition, preferably from 5% to 50% by weight with respect to the total weight of the composition.

The present invention furthermore provides a method of combating invertebrate pests, said method comprising contacting the invertebrate pests, their habitat, breeding ground, food supply, plant, seed, soil, area, material or environment in which the invertebrate pests are growing or may grow, or the materials, plants, seeds, soils, surfaces or spaces to be protected from pest attack or infestation with a biologically effective amount of the compound of formula (I) or agriculturally acceptable salts, isomers/structural isomers, stereo-isomers, diastereomers, enantiomers, tautomers, metal complexes, polymorphs, or N-oxides thereof composition or combination thereof.

Invertebrate pests are controlled and protection of agronomic, horticultural and specialty crops, animal and human health is achieved by applying one or more of the compounds of the present invention, in an effective amount, to the environment of the pests including the agronomic and/or nonagronomic locus of infestation, to the area to be protected, or directly on the pests to be controlled. Thus, the present invention further comprises a method for the control of foliar- and soil-inhabiting invertebrates and protection of agronomic and/or nonagronomic crops, comprising contacting the invertebrates or their environment with a biologically effective amount of one or more of the compounds of the present invention, or with a composition comprising at least one such compound or a composition comprising at least one such compound and an effective amount of at least one additional biologically active compound or agent. A preferred method of contact is by spraying. Alternatively, a granular composition comprising a compound of the present invention can be applied to the plant foliage or the soil. Compounds of the present invention are effective in delivery through plant uptake by contacting the plant with a composition comprising a compound of the present invention applied as a soil drench of a liquid formulation, a granular formulation to the soil, a nursery box treatment or a dip of transplants. Other methods of contact include application of a compound or a composition of the present invention by direct and residual sprays, aerial sprays, seed coats, microencapsulations, systemic uptake, baits, eartags, boluses, foggers, fumigants, aerosols, dusts and many others.

The compounds of the present invention can be incorporated into baits that are consumed by the invertebrates or within devices such as traps and the like. Granules or baits comprising between 0.01-5% active ingredient, 0.05-10% moisture retaining agent(s) and 40-99% vegetable flour are effective in controlling soil insects at very low application rates, particularly at doses of active ingredient that are lethal by ingestion rather than by direct contact. The compounds of the present invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader, stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The animal pest, i.e. the arthropods, gastropods, and nematodes, the plant, soil or water in which the plant is growing can be contacted with compounds of formula (I), their N-oxides and salts or composition(s) containing them by any application method known in the art. As used herein, "contacting" includes both direct contact (applying the compounds/compositions directly on the animal pest or plant typically to the foliage, stem or roots of the plant) and indirect contact (applying the compounds/compositions to the locus of the animal pest or plant).

The compounds of the present invention or the pesticidal compositions comprising them may be used to protect growing plants and crops from attack or infestation by animal pests, especially insects, acaridae or arachnids by contacting the plant/crop with a pesticidally effective amount of at least one compound of the present invention. The term "crop" refers both to growing and harvested crops.

The compounds of the invention are also suitable for use in combating or controlling animal pests. Therefore, the invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the invention.

In one embodiment, the present invention provides a method for protecting crops from attack or infestation by invertebrate pests, which comprises contacting the crop with a biologically effective amount of the compound or the composition of the present invention, isomer, polymorph, N-oxide or salt thereof.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

In one embodiment, the present invention provides a method for the protection of seeds from soil insects and of the seedlings roots and shoots from soil and foliar insects comprising contacting the seeds before sowing and/or after pre-germination with the compound or the composition of the present invention, N-oxide or salt thereof.

Furthermore, the present invention provides a method for treating or protecting animals against infestation or infection by parasites which comprises orally, topically or parenterally administering or applying to the animals a biologically effective amount of compound or composition of the present invention, isomer, polymorph, N-oxide or veterinary acceptable salt thereof.

For use in treating crop plants, the rate of application (applying effective dosages) of the compound of the present invention may be in the range of 1 gai to 5000 gai per hectare in agricultural or horticultural crops, preferably from 25 g to 600 g per hectare, more preferably from 50 g to 500 g per hectare.

The compounds and the compositions of the present invention are particularly useful in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

Particularly, the compound or the composition of the present invention are useful in protecting agricultural crops such as cereals, corn, rice, soybean and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and other vegetables, and ornamentals.

The compounds of the present invention are effective through both contact (via soil, glass, wall, bed net, carpet, plant parts or animal parts), and ingestion (bait or plant part).

The compounds of the present invention may also be applied against non-crop invertebrate pests, such as ants, termites, wasps, flies, mosquitos, crickets, or cockroaches. For use against said non-crop pests, compounds of the present invention are preferably used in a bait composition.

As used herein, the term "non-crop insect pest" refers to pests, which are particularly relevant for non-crop targets, such as ants, termites, wasps, flies, ticks, mosquitos, crickets or cockroaches.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish or blood meal, insect parts, egg yolk), from fats and oils of animal and/or plant origin, or mono-, oligo or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used. For use in spray compositions, the content of active ingredient is from 0.001 to 80 weights %, preferably from 0.01 to 50 weight % and most preferably from 0.01 to 15 weight %.

The compounds of the present invention and their respective compositions can also be used in mosquito and fumigating coils, smoke cartridges, vaporizer plates or long-term vaporizers and also in moth papers, moth pads or other heat-independent vaporizer systems.

The methods to control infectious diseases transmitted by insects (e.g. malaria, dengue and yellow fever, lymphatic filariasis, and leishmaniasis) with compounds of formula (I) and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of the present invention and their compositions can be used for protecting wooden materials such as trees, board fences, sleepers, etc. and buildings such as houses, outhouses, factories, but also construction materials, furniture, leathers, fibers, vinyl articles, electrie wires and cables etc. from ants and/or termites, and for controlling ants and termites from doing harm to crops or human being (e.g. when the pests invade into houses and public facilities). The compounds of the present invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc.

In case of application against ants doing harm to crops or human beings, a compound of the present invention is applied to the crops or the surrounding soil, or is directly applied to the nest of ants or the like.

Seed Treatment

The present invention further provides a seed comprising the compounds of the present invention, particularly in an amount ranging from about 0.0001% to about 1% by weight of the seed before treatment.

The compounds of the present invention are also suitable for the treatment of seeds in order to protect the seed from insect pest, in particular from soil-living insect and mite pests and the resulting plant's roots and shoots against soil pests and foliar insects.

The compounds of the present invention are particularly useful for the protection of the seed from soil pests and the resulting plant's roots (white grub, termites, wireworms) and shoots against soil pests and foliar insects. The protection of the resulting plant's roots and shoots is preferred. More preferred is the protection of resulting plant's shoots from piercing and sucking insects, wherein the protection from aphids, jassids, thrips and white flies is most preferred.

The present invention therefore comprises a method for the protection of seeds from insects, in particular from soil insects and of the seedling roots and shoots from insects, in particular from soil and foliar insects, said method comprising contacting the seeds before sowing and/or after pregermination with a compound of the present invention thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound. The seeds can be coated with seed coating compositions containing the compounds of the present invention. For example, seed coating compositions reported in EP3165092, EP3158864, WO2016198644, WO2016039623, WO2015192923, CA2940002, US2006150489, US2004237395, WO2011028115, EP2229808, WO2007067042, EP1795071, EP1273219, WO200178507, EP1247436, NL1012918 and CA2083415.

The term "coated with and/or containing" generally signifies that the active ingredient is for the most part on the surface of the propagation product at the time of application, although a greater or lesser part of the ingredient may penetrate into the propagation product, depending on the method of application. When the propagation product is (re)planted, it may absorb the active ingredient along with moisture.

Suitable seed is seeds of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the compounds of the present invention may be used for treating seeds from plants, which tolerate the action of herbicides or fungicides or insecticides owing to breeding, including genetic engineering methods.

For example, the compounds of the present invention can be employed in treatment of seeds from plants, which are resistant to herbicides from the group consisting of the sulfonylureas, imidazolinones, glufosinate-ammonium or glyphosate-isopropylammonium and analogous active substances (see for example, EP242236, EP242246) (WO92/00377) (EP257993, U.S. Pat. No. 5,013,659) or in transgenic crop plants, for example cotton, with the capability of producing *Bacillus thuringiensis* toxins (Bt toxins) which make the plants resistant to certain pests (EP142924, EP193259).

Furthermore, the compound of the present invention can be used for the treatment of seeds from plants, which have modified characteristics in comparison with existing plants, which can be generated for example by traditional breeding methods and/or the generation of mutants, or by recombinant procedures). For example, a number of cases have been described of recombinant modifications of crop plants for the purpose of modifying the starch synthesized in the plants (e.g. WO92/11376, WO92/14827, WO91/19806) or of transgenic crop plants having a modified fatty acid composition (WO91/13972).

The seed treatment application of the compound of the present invention is carried out by spraying or by dusting the seeds before sowing of the plants and before emergence of the plants.

Compositions which are especially useful for seed treatment are e.g.:

A. Soluble concentrates (SL, LS)
B. Emulsions (EW, EO, ES)
C. Suspensions (SC, OD, FS)
D. Water-dispersible granules and water-soluble granules (WG, SG)
E. Water-dispersible powders and water-soluble powders (WP, SP, WS)
F. Gel-Formulations (GF)
G. Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a one embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially FS formulations of compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed treatment formulations may additionally comprise binders and optionally colorants.

Binders can be added to improve the adhesion of the active materials on the seeds after treatment. Suitable binders are homo and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo and copolymers, polyethyleneamines, polyethyleneamides and polyethylenepyrimidines, polysaccharides like celluloses, tylose and starch, polyolefin homo and copolymers like olefin/maleic anhydride copolymers, polyurethanes, polyesters, polystyrene homo and copolymers.

Optionally, also colorants can be included in the formulation. Suitable colorants or dyes for seed treatment formulations are Rhodamin B, C.I. Pigment Red 1 12, C.I. Solvent Red 1, pigment blue 15:4, pigment blue 15:3, pigment blue 15:2, pigment blue 15:1, pigment blue 80, pigment yellow 1, pigment yellow 13, pigment red 1 12, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

In the treatment of seed, the application rates of the compounds of the present invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed. The present invention therefore also provides to seeds comprising a compound of formula (I), or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed.

Animal Health

The present invention also provides an agricultural and/or veterinary composition comprising at least of one compound of formula (I).

In one embodiment, the present invention provides use of the compound of formula (I), agriculturally acceptable salts, isomers/structural isomers, stereo-isomers, diastereomers, enantiomers, tautomers, metal complexes, polymorphs, or N-oxides, composition or combination thereof, for combating invertebrate pests in agricultural crops and/or horticultural crops or parasites on animals.

The compounds of formula (I), their N-oxides and/or veterinarily acceptable salts thereof are in particular also suitable for being used for combating parasites in and on animals.

The present invention also provides a compositions containing a parasiticidally effective amount of at least one compound of formula (I), N-oxide or veterinarily acceptable salt thereof and an acceptable carrier, for combating parasites in and on animals.

The present invention also provides a method for treating, controlling, preventing and protecting animals against infestation and infection by parasites, which comprises orally, topically, or parenteral administering or applying to the animals a parasiticidally effective amount of a compound of the present invention or a composition comprising it.

The present invention also provides a process for the preparation of a composition for treating, controlling, preventing or protecting animals against infestation or infection by parasites which comprises a parasiticidally effective amount of a compound of the present invention or a composition comprising it.

Activity of compounds against agricultural pests does not suggest their suitability for control of endo and ectoparasites in and on animals which requires, for example, low, nonemetic dosages in the case of oral application, metabolic compatibility with the animal, low toxicity, and a safe handling. Surprisingly it has now been found that compounds of the present invention are suitable for combating endo and ectoparasites in and on animals.

Compounds of the present invention and compositions comprising them are preferably used for controlling and preventing infestations and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as freshand salt-water fish such as trout, carp and eels.

Compounds of the present invention and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention and compositions comprising them are suitable for systemic and/or non-systemic control of ecto and/or endoparasites. They can be active against all or some stages of development.

The compounds of the present invention are especially useful for combating ectoparasites.

The compounds of the present invention are especially useful for combating parasites of the following orders and species, respectively: fleas (*Siphonaptera*), e.g. *Ctenocephalides felis, Ctenocephalides cams, Xenopsylla cheopis, Pulex irritans, Tunga penetrans*, and *Nosopsyllus fasciatus*, cockroaches (*Blattaria* Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pi pi ens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus,*

*Tabanus atratus, Tabanus lineola*, and *Tabanus similis*, lice (Phthiraptera), e.g. *Pediculus humanus* capitis, *Pediculus humanus* corporis, *Pthirus pubis, Haematopinus eurysternus, Haematopinus suis, Linognathus vituli, Bovicola bovis, Menopon gallinae, Menacanthus stramineus* and *Solenopotes capillatus*. ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, Actinedida (Prostigmata) und Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.

Roundworms Nematoda:

Wipeworms and Trichinosis (Trichosyringida), e.g. Trichinellidae (*Trichinella* spp.), (Trichuridae,) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*, Camallanida, e.g. *Dracunculus medinensis* (guinea worm) Spirurida, e.g. *Thelazia* spp. *Wuchereria* spp., *Brugia* spp., *Onchocerca* spp., *Dirofilari* spp. a, *Dipetalonema* spp., *Setaria* spp., *Elaeophora* spp., *Spirocerca lupi*, and *Habronema* spp, Thorny headed worms (Acanthocephala), e.g. *Acanthocephalus* spp., *Macracanthorhynchus hirudinaceus* and *Oncicola* spp, Planarians (Plathelminthes): Flukes (Trematoda), e.g. *Faciola* spp., Fascioloides *magna, Paragonimus* spp., *Dicrocoelium* spp., *Fasciolopsis buski, Clonorchis sinensis, Schistosoma* spp., *Trichobilharzia* spp., *Alaria a lata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula (I) and compositions containing them are particularly useful for the control of pests from the orders Diptera, *Siphonaptera* and Ixodida.

In one embodiment, the present invention provides use of the compounds of formula (I) and compositions containing them for combating mosquitoes.

In one embodiment, the present invention provides use of the compounds of formula (I) and compositions containing them for combating flies.

In one embodiment, the present invention provides use of the compounds of formula (I) and compositions containing them for combating fleas.

The use of the compounds of the present invention and compositions containing them for combating ticks is still another embodiment of the present invention.

The compounds of the present invention are also especially useful for combating endoparasites (roundworms nematoda, thorny headed worms and planarians).

In one embodiment, the administration of the compounds of the present invention can be carried out both prophylactically and therapeutically.

In another embodiment, administration of the compounds of the present invention is carried out directly or in the form of suitable preparations, orally, topically/dermally or parenterally.

For oral administration to warm-blooded animals, compounds of the present invention may be formulated as animal feeds, animal feed premixes, animal feed concentrates, pills, solutions, pastes, suspensions, drenches, gels, tablets, boluses and capsules. In addition, the compounds of the present invention may be administered to the animals in their drinking water. For oral administration, the dosage form chosen should provide the animal with 0.01 mg/kg to 100 mg/kg of animal body weight per day of the compound of the present invention, preferably with 0.5 mg/kg to 100 mg/kg of animal body weight per day.

Alternatively, the compounds of the present invention may be administered to animals parenterally, for example, by intraruminal, intramuscular, intravenous or subcutaneous injection. The compounds of the present invention may be dispersed or dissolved in a physiologically acceptable carrier for subcutaneous injection. Alternatively, the compounds of the present invention may be formulated into an implant for subcutaneous administration. In addition the compound of the present invention may be transdermally administered to animals. For parenteral administration, the dosage form chosen should provide the animal with 0.01 mg/kg to 100 mg/kg of animal body weight per day of the compound of the present invention.

The compounds of the present invention may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compound of the present invention. In addition, the compounds of the present invention may be formulated as ear tags for animals, particularly quadrupeds such as cattle and sheep.

Suitable preparations are: Solutions such as oral solutions, concentrates for oral administration after dilution, solutions for use on the skin or in body cavities, pouring-on formulations, gels; Emulsions and suspensions for oral or dermal administration; semi-solid preparations; Formulations in which the active compound is processed in an ointment base or in an oil-in-water or water-in-oil emulsion base; Solid preparations such as powders, premixes or concentrates, granules, pellets, tablets, boluses, capsules; aerosols and inhalants, and active compound-containing shaped articles.

The compositions suitable for injection are prepared by dissolving the active ingredient in a suitable solvent and optionally adding further ingredients such as acids, bases, buffer salts, preservatives, and solubilizers.

The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the used concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency result. The thickeners employed are the thickeners given above.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are for example, water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, dimethylformamide, dimethylacetamide, n-alkylpyrrolidones such as methylpyrrolidone, n-butylpyrrolidone or noctylpyrrolidone, N-methylpyrrolidone, 2-pyrrolidone, 2,2-dimethyl-4-oxy-methylene-1,3-dioxolane or glycerol formal.

Suitable colorants are for example, all colorants permitted for use on animals and which can be dissolved or suspended.

Suitable absorption-promoting substances are for example, dimethyl sulfoxide, spreading oils such as isopropyl myristate, dipropylene glycol pelargonate, silicone oils and copolymers thereof with polyethers, fatty acid esters, triglycerides or fatty alcohols.

Suitable antioxidants are for example, sulfites or metabisulfites such as potassium metabisulfite, ascorbic acid, butylhydroxytoluene, butylhydroxyanisole or tocopherol.

Suitable light stabilizers are for example, novantisolic acid. Suitable adhesives are, for example, cellulose derivatives, starch derivatives, polyacrylates or natural polymers such as alginates, gelatin. Emulsions can be administered orally, dermally or as injections. Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable Hydrophobic Phases (Oils) are:

Liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_1$-$C_{12}$ or other specially selected natural fatty acids, partial glyceride mixtures of saturated or unsaturated fatty acids possibly also containing hydroxyl groups, mono and diglycerides of the Cs-do fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof. Suitable hydrophilic phases are: water, alcohols such as propylene glycol, glycerol, sorbitol and mixtures thereof.

Suitable emulsifiers are for example, non-ionic surfactants, e.g. polyethoxylated castor oil, polyethoxylated sorbitan monooleate, sorbitan monostearate, glycerol monostearate, polyoxyethyl stearate, alkylphenol polyglycol ether; ampholytic surfactants such as di-sodium N-lauryl-p-iminodipropionate or lecithin.

Suitable anionic surfactants are for example, sodium lauryl sulfate, fatty alcohol ether sulfates, mono/dialkyl polyglycol ether orthophosphoric acid ester monoethanolamine salt; suitable cation-active surfactants are cetyltrimethylammonium chloride.

Suitable further auxiliaries are for example, substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the present invention. A parasiticidally effective amount of the compositions will also vary according to the prevailing conditions such as desired parasiticidal effect and duration, target species, mode of application, and the like. The compositions which can be used in the present invention generally comprise from about 0.001 to 95% of the compound of the present invention.

Generally, it is favorable to apply the compounds of the present invention in total amounts of 0.5 mg/kg to 100 mg/kg per day, preferably 1 mg/kg to 50 mg/kg per day. Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight. Preparations diluted before use contain the compounds acting against ectoparasites in concentrations of 0.5 to 90 percent by weight, preferably of 1 to 50 percent by weight. Furthermore, the preparations comprise the compounds of the present invention against endoparasites in concentrations of 10 ppm to 2 percent by weight, preferably of 0.05 to 0.9 percent by weight, very particularly preferably of 0.005 to 0.25 percent by weight.

In a one embodiment, the compositions comprising the compounds of the present invention are applied dermally/topically.

In another embodiment, the topical application is conducted in the form of compound-containing shaped articles such as collars, medallions, ear tags, bands for fixing at body parts, and adhesive strips and foils.

Generally, it is favorable to apply solid formulations which release compounds of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of the present invention. A detailed list of plastics and elastomers as well as preparation procedures for the shaped articles is given e.g. in WO 2003086075.

Positive Crop Response:

The compounds of the present invention not only control insect and mite pests effectively but also show a positive crop response such as plant growth enhancement effects like enhanced root growth, enhanced tolerance to drought, high salt, high temperature, chill, frost or light radiation, improved flowering, enhanced nutrient utilization (such as improved nitrogen assimilation), enhanced quality of plant products, higher number of productive tillers, enhanced resistance to fungi, insects, pests and the like, which results in higher yields.

Without further elaboration, it is reasonable to believe that any person skilled in the art who is using the preceding description can utilize the present invention to its fullest extent. The following examples are therefore to be interpreted as merely illustrative and not limiting of the disclosure in any way whatever.

Chemistry Examples

The following examples set forth the manner and process of making compounds of the present invention without being a limitation thereof and include the best mode contemplated by the inventors for carrying out the invention.

Scheme 4 Synthesis of N-alkylated trifluoromethyltriazole benzamide compounds (6) and (7)

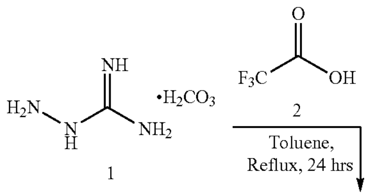

1

2

-continued

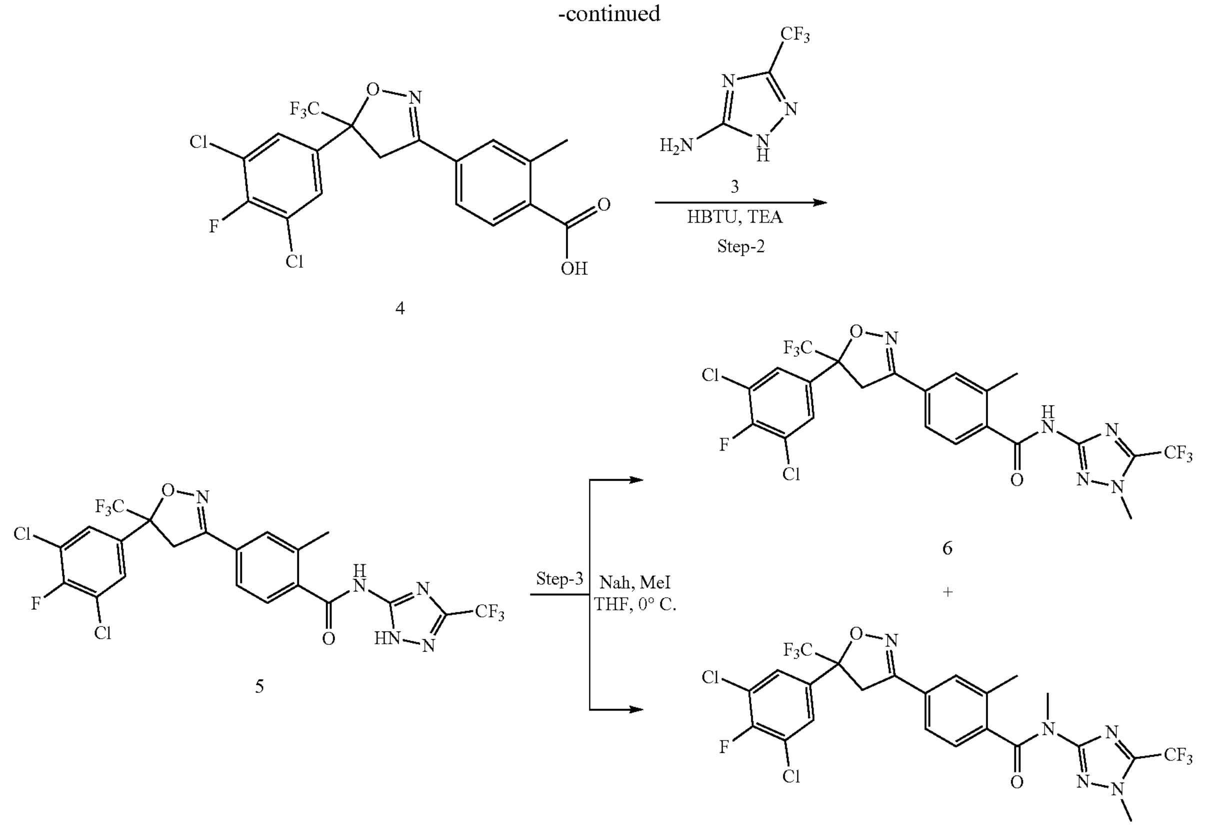

a) Step-1: 3-(trifluoromethyl)-1H-1,2,4-triazol-5-amine (3)

To aminoguanidine hydrogencarbonate (19.70 g, 145 mmol) in a round bottom flask, 2,2,2-trifluoroacetic acid (15 g, 132 mmol) was added dropwise and under stirring. The mixture was stirred for 30 minutes at 25° C., followed by addition of toluene (150 mL). The resulting reaction mixture was heated under reflux (at about 140° C.) and stirring using a Dean-Stark trap for about 24 h. After completion of the reaction, the reaction mixture was cooled to 25° C., the resulting solid was filtered, washed twice with toluene (25 mL) and dried under reduced pressure to obtain 5-(trifluoromethyl)-4H-1,2,4-triazol-3-amine (11.8 g, 78 mmol, 88% yield). $^1$H-NMR (400 MHz, DMSO-$d_6$) δ 12.72 (s, 1H), 6.45 (s, 2H); ESI MS (m/z) 152.9, $(M+H)^+$.

b) Step-2: 4-(5-(3,5-dichloro-4-fluorophenyl)-5-(trifluoromethyl)-4,5-dihydroisoxazol-3-yl)-2-methyl N-(3-(trifluoromethyl)-1H-1,2,4-triazol-5-yl)benzamide (5)

To a stirred solution of 4-(5-(3,5-dichloro-4-fluorophenyl)-5-(trifluoromethyl)-4,5-dihydroisoxazol-3-yl)-2-methylbenzoic acid (5 g, 11.5 mmol) and o-benzotriazol-1-yl-tetramethyluronium hexafluorophosphate (15.22 g, 40.1 mmol) in N,N-dimethylformamide (50 mL), triethyl amine (5.59 mL, 40.1 mmol) was added and the reaction mixture was stirred at 25° C. for 15 minutes. To this reaction mixture, 3-(trifluoromethyl)-1H-1,2,4-triazol-5-amine (6.10 g, 40.1 mmol) was added and the resulting mixture was stirred at 55° C. for further 6 h. After completion of the reaction, the reaction mixture was poured into water (200 mL), followed by addition of HCl (6 N, 25 mL). The precipitate which was obtained was filtered, washed with water and dried under reduced pressure. The obtained crude material was purified by column chromatography to obtain 4-(5-(3,5-dichloro-4-fluorophenyl)-5-(trifluoromethyl)-4,5-dihydroisoxazol-3-yl)-2-methyl-N-(3-(trifluoromethyl)-1H-1,2,4-triazol-5-yl) benzamide (3.2 g, 5.6 mmol, 49% yield). $^1$H-NMR (400 MHz, DMSO-$d_6$) δ 14.46 (s, 1H), 12.36 (s, 1H), 7.78 (dd, J=6.2, 2.1 Hz, 2H), 7.61-7.69 (m, 3H), 4.29-4.40 (m, 2H), 2.46 (s, 3H); ESI MS (m/z) 568.00 $(M-H)^-$.

c) Step-3: 4-(5-(3,5-dichloro-4-fluorophenyl)-5-(trifluoromethyl)-4,5-dihydroisoxazol-3-yl)-2-methyl-N-(1-methyl-5-(trifluoromethyl)-1H-1,2,4-triazol-3-yl)benzamide (6)

To a solution of 4-(5-(3,5-dichloro-4-fluorophenyl)-5-(trifluoromethyl)-4,5-dihydroisoxazol-3-yl)-2-methyl-N-(3-(trifluoromethyl)-1H-1,2,4-triazol-5-yl)benzamide in tetrahydrofuran (50 mL), sodium hydride (0.337 g, 7.7 mmol) was added at 0° C. The resulting solution was stirred for 15 minutes at 25° C., cooled down to 0° C., and iodomethane (1.0 g, 7.7 mmol) was added. The reaction mixture was stirred at 25° C. for 5 h. After completion of the reaction, the reaction mixture was diluted with water (10 mL) and extracted twice with ethyl acetate (50 mL). The combined ethyl acetate extracts were washed with brine solution, dried over anhydrous sodium sulphate and evaporated under reduced pressure to get a crude material. The obtained crude material was purified by column chromatography to obtain 4-(5-(3,5-dichloro-4-fluorophenyl)-5-(trifluoromethyl)-4,5- dihydroisoxazol-3-yl)-2-methyl-N-(1-methyl-5-(trifluoromethyl)-1H-1,2,4-triazol-3-yl)benzamide (0.25 g, 4.3 mmol, 61% yield). $^1$H-NMR (400 MHz, DMSO-$d_6$) δ 11.16 (s, 1H), 7.80 (d, J=6.4 Hz, 2H), 7.63 (d, J=10.3 Hz, 2H), 7.56 (d, J=8.1 Hz, 1H), 4.35 (dd, J=27.3, 18.5 Hz, 2H), 4.01 (m, 3H), 2.41 (s, 3H), ESI MS (m/z) 584.00 (M+H)$^+$.

d) 4-(5-(3,5-dichloro-4-fluorophenyl)-5-(trifluoromethyl)-4,5-dihydroisoxazol-3-yl)-N,2-dimethyl-N-(1-methyl-5-(trifluoromethyl)-1H-1,2,4-triazol-3-yl) benzamide (7)

Compound 7 was obtained as a by-product, prepared by the same procedure as shown in Scheme-4, step-3. Its purification was conducted by column chromatography to obtain 4-(5-(3,5-dichloro-4-fluorophenyl)-5-(trifluoromethyl)-4,5-dihydroisoxazol-3-yl)-N,2-dimethyl-N-(1-methyl-5-(trifluoromethyl)-1H-1,2,4-triazol-3-yl)benzamide (15% yield). $^1$H-NMR (400 MHz, DMSO-$d_6$) δ 7.79 (d, J=6.1 Hz, 2H), 7.64-7.69 (m, 3H), 4.35 (dd, J=30.4, 18.5 Hz, 2H), 3.85 (s, 3H), 3.82 (s, 3H) 2.44 (s, 3H) ESI MS (m/z) 598.00 (M+H)$^+$.

Scheme 5 N-alkylated methyltriazole benzamides (11) and (12)

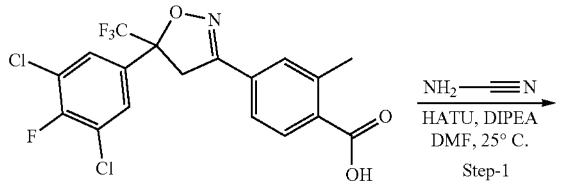

4

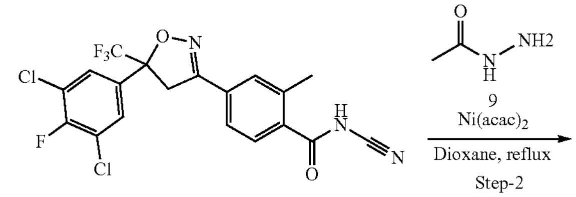

8

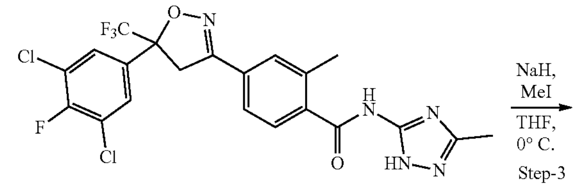

10

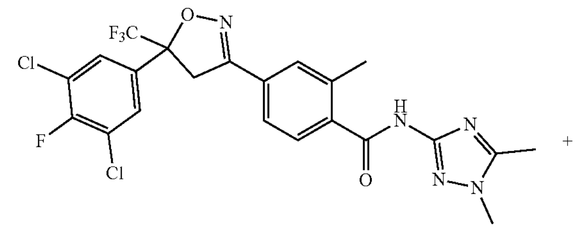

11

-continued

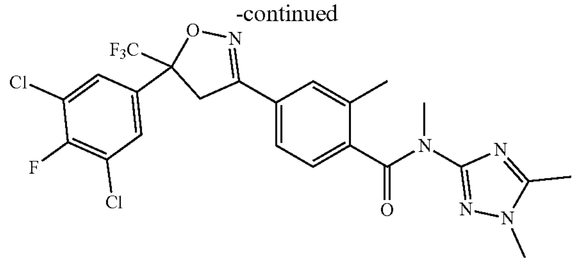

12 a) Step-1: N-cyano-4-(5-(3,5-dichloro-4-fluorophenyl)-5-(trifluoromethyl)-4,5-dihydroisoxazol-3-yl)-2-methylbenzamide (8)

To a solution of 4-(5-(3,5-dichloro-4-fluorophenyl)-5-(trifluoromethyl)-4,5-dihydroisoxazol-3-yl)-2-methylbenzoic acid (20 g, 46 mmol) and HATU (20.9 g, 55 mmol) in N,N-dimethylformamide (200 mL), diisopropylethylamine (16.02 mL, 92 mmol) was added and the resulting mixture was stirred at 25° C. for 20 minutes. To the above reaction mixture, a solution of cyanamide (2.50 g, 59.6 mmol)) in N,N-dimethylformamide (10 mL) was added. The resulting reaction mixture was stirred at 25° C. for 12 h. After completion of the reaction, the reaction mixture was poured into water (1000 mL), followed by addition of hydrochloric acid (HCl) (6 N, 50 mL). The obtained precipitate was filtered off, washed with water and dried under reduced pressure to get a crude solid. The obtained crude solid was purified by column chromatography to obtain N-cyano-4-(5-(3,5-dichloro-4-fluorophenyl)-5-(trifluoromethyl)-4,5-dihydroisoxazol-3-yl)-2-methylbenzamide (10 g, 21.7 mmol, 47% yield). $^1$H-NMR (400 MHz, DMSO-$d_6$) δ 7.79 (d, J=6.1 Hz, 2H), 7.64-7.69 (m, 3H), 4.35 (dd, J=30.4, 18.5 Hz, 2H), 2.44 (s, 3H) ESI MS (m/z) 458.00 (M−H)$^-$.

b) Step-2: 4-(5-(3,5-dichloro-4-fluorophenyl)-5-(trifluoromethyl)-4,5-dihydroisoxazol-3-yl)-2-methyl-N-(3-methyl-1H-1,2,4-triazol-5-yl)benzamide (10)

A mixture of N-cyano-4-(5-(3,5-dichloro-4-fluorophenyl)-5-(trifluoromethyl)-4,5-dihydroisoxazol-3-yl)-2-methylbenzamide (3.0 g, 6.5 mmol), monoacetyl hydrazine (0.53 g, 7.71 mmol) and acetylacetone nickel(II) (0.167 g, 0.65 mmol) in anhydrous dioxane (50 mL) was refluxed while stirring for 24 h under dry nitrogen. The reaction mixture was evaporated to half of the initial volume and triturated by adding methanol (10 mL). The precipitate which was obtained was filtered off and dried under reduced pressure to obtain 4-(5-(3,5-dichloro-4-fluorophenyl)-5-(trifluoromethyl)-4,5-dihydroisoxazol-3-yl)-2-methyl-N-(3-methyl-1H-1,2,4-triazol-5-yl)benzamide (0.8 g, 6.5 mmol, 24% yield). $^1$H-NMR (400 MHz, DMSO-$d_6$) δ 13.24 (d, J=9.5 Hz, 1H), 12.33-11.44 (1H), 7.80 (d, J=6.1 Hz, 2H), 7.62 (d, J=12.0 Hz, 3H), 4.35 (dd, J=27.1, 18.3 Hz, 2H), 2.41 (s, 3H), 2.22-2.32 (m, 3H) ESI MS (m/z) 516.00 (M+H)$^+$.

Compounds 11 and 12 were prepared from intermediate 10 by a similar procedure described in Scheme-4, Step-3.

Scheme 6 Synthesis of N-alkylated thiomethyltriazole benzamide (16) and (17)

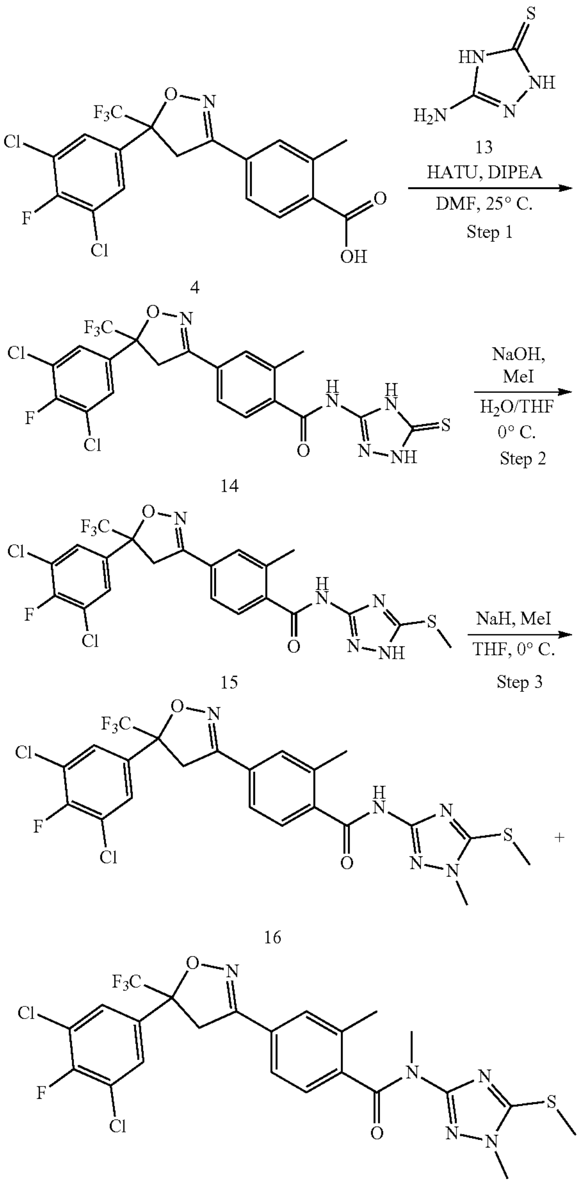

17 a) Step-1: 4-(5-(3,5-dichloro-4-fluorophenyl)-5-(trifluoromethyl)-4,5-dihydroisoxazol-3-yl)-2-methyl-N-(5-thioxo-4,5-dihydro-1H-1,2,4-triazol-3-yl)benzamide (14)

To a stirred solution of 4-(5-(3,5-dichloro-4-fluorophenyl)-5-(trifluoromethyl)-4,5-dihydroisoxazol-3-yl)-2-methylbenzoic acid (2.0 g, 4.6 mmol) and diisopropylethylamine (2.0 mL, 11.4 mmol) in N,N-dimethylformamide (25 mL), HATU (2.3 g, 6.2 mmol) was added, and the resulting reaction mixture was stirred at 25° C. for 30 minutes. To this mixture, 5-amino-2,4-dihydro-3H-1,2,4-triazole-3-thione (0.53 g, 4.6 mmol) was added and the reaction mixture was stirred at 25° C. for additional 2 h, after which it was heated at 50° C. for further 10 h. After completion of the reaction, the reaction mixture was poured into water, the obtained solid was filtered and was washed twice with water (10 mL). The crude solid was triturated by adding ethyl acetate and hexane, the obtained solid was filtered off and dried under reduced pressure to obtain 4-(5-(3,5-dichloro-4-fluorophenyl)-5-(trifluoromethyl)-4,5-dihydroisoxazol-3-yl)-2-methyl-N-(5-thioxo-4,5-dihydro-1H-1,2,4-triazol-3-yl)benzamide (1.2 g, 2.5 mmol, 49% yield). $^1$H-NMR (400 MHz, DMSO-$d_6$) δ 13.26-13.33 (m, 2H), 11.34 (s, 1H), 7.80 (d, J=6.1 Hz, 2H), 7.65 (d, J=7.9 Hz, 2H), 7.59 (d, J=7.9 Hz, 1H), 4.36 (dd, J=28.1, 18.3 Hz, 2H), 2.44 (s, 3H), ESI MS (m/z) 534.00 $(M+H)^+$.

b) Step-2: 4-(5-(3,5-dichloro-4-fluorophenyl)-5-(trifluoromethyl)-4,5-dihydroisoxazol-3-yl)-2-methyl-N-(5-(methylthio)-1H-1,2,4-triazol-3-yl) benzamide (15)

To a stirred solution of 4-(5-(3,5-dichloro-4-fluorophenyl)-5-(trifluoromethyl)-4,5-dihydroisoxazol-3-yl)-2-methyl-N-(5-thioxo-4,5-dihydro-1H-1,2,4-triazol-3-yl)benzamide (0.25 g, 0.5 mmol) in water (15 mL) and tetrahydrofuran (5 mL), an aqueous solution of 1N sodium hydroxide (0.52 mL, 0.5 mmol) was added, and the resulting mixture was stirred for 1 h. To this reaction mixture iodomethane (0.03 mL, 0.5 mmol) was added at 0° C., and the resulting mixture was allowed to stirred at 25° C. for 5 h. The reaction mixture was then evaporated under reduced pressure till dryness, water (40 mL) was added to the residue, and the mixture was extracted thrice with ethyl acetate (10 mL). The combined ethyl acetate layers were washed with brine solution, dried over anhydrous sodium sulfate and evaporated under reduced pressure to get crude material, which was purified by column chromatography to obtain 4-(5-(3,5-dichloro-4-fluorophenyl)-5-(trifluoromethyl)-4,5-dihydroisoxazol-3-yl)-2-methyl-N-(5-(methylthio)-4H-1,2,4-triazol-3-yl)benzamide (0.11 g, 0.5 mmol, 45% yield). $^1$H-NMR (400 MHz, DMSO-$d_6$) δ 13.55 (s, 1H), 11.97 (s, 1H), 7.80 (d, J=6.4 Hz, 2H), 7.64 (d, J=11.7 Hz, 3H), 4.36 (dd, J=28.1, 18.3 Hz, 2H), 2.50 (s, 3H), 2.41 (d, J=14.7 Hz, 3H) ESI MS (m/z) 548.00 $(M+H)^+$.

c) Step-3: 4-(5-(3,5-dichloro-4-fluorophenyl)-5-(trifluoromethyl)-4,5-dihydroisoxazol-3-yl)-2-methyl-N-(1-methyl-5-(methylthio)-1H-1,2,4-triazol-3-yl)benzamide (16)

To a stirred solution of 4-(5-(3,5-dichloro-4-fluorophenyl)-5-(trifluoromethyl)-4,5-dihydroisoxazol-3-yl)-2-methyl-N-(5-(methylthio)-4H-1,2,4-triazol-3-yl)benzamide (0.4 g, 0.7 mmol) in tetrahydrofuran (10 mL), sodium hydride (0.04 g, 0.84 mmol) was added at 0° C. and the resulting reaction mixture was stirred at 0° C. for 5 minutes. Then the reaction mixture was warmed to 25° C. and stirred for 15 minutes. The reaction mixture was cooled to 0° C., iodomethane (0.06 mL, 0.9 mmol) was added and the mixture was stirred at 25° C. for further 12 h. After completion of the reaction, the reaction mixture was evaporated under reduced pressure to dryness. The residue obtained was purified by preparative HPLC to obtain 4-(5-(3,5-dichloro-4-fluorophenyl)-5-(trifluoromethyl)-4,5-dihydroisoxazol-3-yl)-2-methyl-N-(1-methyl-5-(methylthio)-1H-1,2,4-triazol-3-yl) benzamide (0.10 g, 0.2 mmol, 24% yield). $^1$H-NMR (400 MHz, DMSO-$d_6$) δ 10.78 (s, 1H), 7.80 (d, J=6.1 Hz, 2H), 7.61 (d, J=11.0 Hz, 2H), 7.52 (d, J=7.9 Hz, 1H), 4.35

(dd, J=26.9, 18.3 Hz, 2H), 3.68 (s, 3H), 2.60 (s, 3H), 2.40 (s, 3H); ESI MS (m/z) 562.00 $(M+H)^+$.

d) 4-(5-(3,5-dichloro-4-fluorophenyl)-5-(trifluoromethyl)-4,5-dihydroisoxazol-3-yl)-N,2-dimethyl-N-(1-methyl-5-(methylthio)-1H-1,2,4-triazo-3-yl)benzamide. (17)

Compound 17 was obtained as a byproduct, prepared by the same procedure as shown in Scheme-6, Step-3, and purified by preparative HPLC to yield 4-(5-(3,5-dichloro-4-fluorophenyl)-5-(trifluoromethyl)-4,5-dihydroisoxazol-3-yl)-N,2-dimethyl-N-(1-methyl-5-(methylthio)-1H-1,2,4-triazol-3-yl)benzamide. $^1$H-NMR (400 MHz, DMSO-$d_6$) δ7.77 (d, J=6.1 Hz, 2H), 7.51 (s, 1H), 7.42-7.44 (m, 1H), 7.15 (d, J=7.8 Hz, 1H), 4.28 (dd, J=25.7, 18.3 Hz, 2H), 3.49 (s, 3H), 3.34 (s, 3H), 2.32 (s, 3H), 2.27 (s, 3H) ESI MS (m/z) 576.00 $(M+H)^+$.

The following compounds in Table 1 were prepared according to the synthesis described in the examples and the general schemes 1-3.

TABLE 1

| Comp. No. | Compound Name | Analytical data |
|---|---|---|
| 1 | 4-(5-(3,5-dichloro-4-fluorophenyl)-5-(trifluoromethyl)-4,5-dihydroisoxazol-3-yl)-2-methyl-N-(1-methyl-5-(trifluoromethyl)-1H-1,2,4-triazol-3-yl)benzamide | $^1$H-NMR (400 MHz, DMSO-$d_6$) δ 11.16 (s, 1H), 7.80 (d, J = 6.4 Hz, 2H), 7.63 (d, J = 10.3 Hz, 2H), 7.56 (d, J = 8.1 Hz, 1H), 4.35 (dd, J = 27.3, 18.5 Hz, 2H), 4.01-4.03 (m, 3H), 2.41 (s, 3H) ESI MS (m/z) 584.00 $(M)^+$. |
| 2 | 4-(5-(3,5-dichlorophenyl)-5-(trifluoromethyl)-4,5-dihydroisoxazol-3-yl)-2-methyl-N-(1-methyl-5-(trifluoromethyl)-1H-1,2,4-triazol-3-yl)benzamide | $^1$H-NMR (400 MHz, DMSO-$d_6$) δ 11.16 (s, 1H), 7.81 (t, J = 1.8 Hz, 1H), 7.62-7.65 (m, 4H), 7.56 (d, J = 7.8 Hz, 1H), 4.40 (d, J = 18.3 Hz, 1H), 4.31 (d, J = 18.6 Hz, 1H), 4.01 (d, J = 1.0 Hz, 3H), 2.39 (d, J = 12.2 Hz, 3H) ESI MS (m/z) 566.00 $(M)^+$. |
| 3 | 4-(5-(3,5-dichloro-4-fluorophenyl)-5-(trifluoromethyl)-4,5-dihydroisoxazol-3-yl)-N-(5-ethyl-1-methyl-1H-1,2,4-triazol-3-yl)-2-methylbenzamide | $^1$H-NMR (400 MHz, DMSO-$d_6$) δ 10.61 (s, 1H), 7.72-7.81 (m, 2H), 7.60 (d, J = 10.3 Hz, 2H), 7.48-7.55 (m, 1H), 4.29-4.40 (m, 2H), 3.72 (s, 3H), 2.71 (q, J = 7.5 Hz, 2H), 2.38 (d, J = 13.9 Hz, 3H), 1.18-1.26 (m, 3H) ESI MS (m/z) 544.00 $(M)^+$. |
| 4 | 4-(5-(3,5-dichloro-4-fluorophenyl)-5-(trifluoromethyl)-4,5-dihydroisoxazol-3-yl)-N-(5-ethyl-1-methyl-1H-1,2,4-triazol-3-yl)-N,2-dimethylbenzamide | $^1$H-NMR (400 MHz, DMSO-$d_6$) δ 7.77-7.81 (m, 2H), 7.48 (s, 1H), 7.40 (d, J = 8.8 Hz, 1H), 7.12 (d, J = 8.1 Hz, 1H), 4.27 (dd, J = 24.9, 18.3 Hz, 2H), 3.53 (s, 3H), 2.54 (t, J = 7.5 Hz, 2H), 2.26 (s, 3H), 0.96-1.05 (m, 3H) ESI MS (m/z) 558.00 $(M)^+$. |
| 5 | 4-(5-(3,5-dichlorophenyl)-5-(trifluoromethyl)-4,5-dihydroisoxazol-3-yl)-N-(5-ethyl-1-methyl-1H-1,2,4-triazol-3-y1)-2-methylbenzamide | $^1$H-NMR (400 MHz, DMSO-$d_6$) δ 10.60 (s, 1H), 7.81 (t, J = 1.8 Hz, 1H), 7.60-7.62 (m, 4H), 7.45-7.51 (m, 1H), 4.28-4.41 (m, 2H), 3.60-3.72 (m, 3H), 2.71 (q, J = 7.5 Hz, 2H), 2.32-2.42 (m, 3H), 1.20 (t, J = 7.6 Hz, 3H) ESI MS (m/z) 526.00 $(M)^+$. |
| 6 | 4-(5-(3,5-dichlorophenyl)-5-(trifluoromethyl)-4,5-dihydroisoxazol-3-yl)-N-(5-ethyl-1-methyl-1H-1,2,4-triazol-3-yl)-N,2-dimethylbenzamide | $^1$H-NMR (400 MHz, DMSO-$d_6$) δ 7.79-7.81 (m, 1H), 7.60 (d, J = 1.7 Hz, 2H), 7.49 (s, 1H), 7.41 (d, J = 8.1 Hz, 1H), 7.12 (d, J = 7.8 Hz, 1H), 4.28-4.34 (m, 1H), 4.23 (d, J = 18.6 Hz, 1H), 3.56 (d, J = 23.0 Hz, 3H), 2.54 (t, J = 7.6 Hz, 2H), 2.24 (d, J = 19.1 Hz, 3H), 0.98 (t, J = 7.5 Hz, 3H) ESI MS (m/z) 540.00 $(M)^+$. |
| 7 | 4-(5-(3,5-dichlorophenyl)-5-(trifluoromethyl)-4,5-dihydroisoxazol-3-yl)-N-(1,5-diethyl-1H-1,2,4-triazol-3-yl)-N-ethyl-2-methylbenzamide | $^1$H-NMR (400 MHz, DMSO-$d_6$) δ 7.79 (s, 1H), 7.54-7.63 (m, 2H), 7.47 (s, 1H), 7.35-7.40 (m, 1H), 7.07 (d, J = 8.1 Hz, 1H), 4.24 (dd, J = 24.7, 18.3 Hz, 2H), 3.81-3.90 (m, 4H), 2.56 (q, J = 7.5 Hz, 2H), 2.29 (d, J = 18.6 Hz, 3H), 1.16-1.28 (m, 3H), 0.83-1.03 (m, 6H) ESI MS (m/z) 568.00 $(M)^+$. |
| 8 | 4-(5-(3,5-dichlorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)benzamide | $^1$H-NMR (400 MHz, DMSO-$d_6$) δ 10.79 (s, 1H), 7.81 (t, J = 1.8 Hz, 1H), 7.60-7.63 (m, 4H), 7.52 (d, J = 8.1 Hz, 1H), 5.18 (q, J = 9.0 Hz, 2H), 4.34 (dd, J = 34.1, 18.5 Hz, 2H), 2.43 (s, 3H), 2.39 (s, 3H) ESI MS (m/z) 580.00 $(M)^+$. |
| 9 | 4-(5-(3,5-dichloro-4-fluorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)-N-(2,2,2-trifluoroethyl)benzamide | $^1$H-NMR (400 MHz, DMSO-$d_6$) δ 7.78 (d, J = 6.4 Hz, 2H), 7.50 (s, 1H), 7.38 (dd, J = 7.9, 1.1 Hz, 1H), 7.08 (d, J = 8.1 Hz, 1H), 4.98 (q, J = 8.8 Hz, 2H), 4.71 (q, J = 9.1 Hz, 2H), 4.22 (t, J = 19.0 Hz, 2H), 2.31 (s, 3H), 2.28 (s, 3H)ESI MS (m/z) 680.00 (M)+. |
| 10 | 4-(5-(3,5-dichloro-4-fluorophenyl)-5-(trifluoromethyl)-4,5-dihydroisoxazol-3-yl)-2-methyl-N-(1-methyl-5-(methylthio)-1H-1,2,4-triazol-3-yl)benzamide | $^1$H-NMR (400 MHz, DMSO-$d_6$) δ 10.78 (s, 1H), 7.80 (d, J = 6.1 Hz, 2H), 7.61 (d, J = 11.0 Hz, 2H), 7.52 (d, J = 7.9 Hz, 1H), 4.35 (dd, J = 26.9, 18.3 Hz, 2H), 3.68 (s, 3H), 2.60 (s, 3H), 2.40 (s, 3H) ESI MS (m/z) 562.00 $(M)^+$. |
| 11 | 4-(5-(3,5-dichloro-4-fluorophenyl)-5-(trifluoromethyl)-4,5-dihydroisoxazol-3-yl)-N,2-dimethyl-N-(1-methyl-5-(methylthio)-1H-1,2,4-triazol-3-yl)benzamide | $^1$H-NMR (400 MHz, DMSO-$d_6$) δ 7.77 (d, J = 6.1 Hz, 2H), 7.51 (s, 1H), 7.42-7.44 (m, 1H), 7.15 (d, J = 7.8 Hz, 1H), 4.28 (dd, J = 25.7, 18.3 Hz, 2H), 3.49 (s, 3H), 3.34 (s, 3H), 3.31 (s, 3H), 2.32 (s, 3H), 2.27 (s, 3H) ESI MS (m/z) 576.00 $(M)^+$. |
| 12 | 4-(5-(3,5-dichloro-4-fluorophenyl)-5-(trifluoromethyl)-4,5-dihydroisoxazol-3-yl)-N-(1,5-dimethyl-1H-1,2,4-triazol-3-yl)-2-methylbenzamide | $^1$H-NMR (400 MHz, DMSO-$d_6$) δδ10.54 (d, J = 4.6 Hz, 1H), 7.77-7.79 (m, 2H), 7.57-7.60 (m, 2H), 7.47 (d, J = 7.6 Hz, 1H), 4.32 (dd, J = 26.5, 18.2 Hz, 2H), 3.69 (s, 3H), 2.37 (s, 3H), 2.33 (s, 3H) ESI MS (m/z) 530.00 $(M)^+$. |

TABLE 1-continued

| Comp. No. | Compound Name | Analytical data |
|---|---|---|
| 13 | 4-(5-(3,5-dichloro-4-fluorophenyl)-5-(trifluoromethyl)-4,5-dihydroisoxazol-3-yl)-N-(1,5-dimethyl-1H-1,2,4-triazol-3-yl)-N,2-dimethylbenzamide | $^1$H-NMR (400 MHz, DMSO-$d_6$) δ 7.78 (t, J = 6.0 Hz, 2H), 7.49 (s, 1H), 7.41 (d, J = 7.8 Hz, 1H), 7.13 (d, J = 8.1 Hz, 1H), 4.28 (dd, J = 29.2, 18.5 Hz, 2H), 3.51 (s, 3H), 3.29 (s, 3H), 2.27 (s, 3H), 2.20 (s, 3H) ESI MS (m/z) 544.00 $(M + H)^+$. |
| 14 | 4-(5-(3,5-dichlorophenyl)-5-(trifluoromethyl)-4,5-dihydroisoxazol-3-yl)-N-(1,5-dimethyl-1H-1,2,4-triazol-3-yl)-2-methylbenzamide | $^1$H-NMR (400 MHz, DMSO-$d_6$) δ 10.54 (d, J = 4.2 Hz, 1H), 7.79 (q, J = 1.8 Hz, 1H), 7.58-7.62 (m, 4H), 7.47 (d, J = 7.3 Hz, 1H), 4.32 (dd, J = 34.8, 18.5 Hz, 2H), 3.69 (s, 3H), 2.37 (s, 3H), 2.32 (s, 3H) ESI MS (m/z) 512.00 $(M)^+$. |
| 15 | 4-(5-(3,5-dichlorophenyl)-5-(trifluoromethyl)-4,5-dihydroisoxazol-3-yl)-N-(1,5-dimethyl-1H-1,2,4-triazol-3-yl)-N,2-dimethylbenzamide | $^1$H-NMR (400 MHz, DMSO-$d_6$) δ 7.77-7.78 (m, 1H), 7.57 (t, J = 1.8 Hz, 2H), 7.48 (d, J = 3.9 Hz, 1H), 7.38-7.41 (m, 1H), 7.09-7.12 (m, 1H), 4.26 (q, J = 18.6 Hz, 2H), 3.49 (s, 3H), 3.27 (s, 3H), 2.26 (s, 3H), 2.18 (s, 3H) ESI MS (m/z) 526.00 $(M)^+$. |
| 16 | 4-(5-(3,5-dichloro-4-fluorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)benzamide | $^1$H-NMR (400 MHz, DMSO-$d_6$) δ 10.77 (d, J = 2.7 Hz, 1H), 7.77-7.79 (m, 2H), 7.57-7.61 (m, 2H), 7.49 (t, J = 7.7 Hz, 1H), 5.16 (q, J = 9.0 Hz, 2H), 4.32 (dd, J = 26.2, 18.3 Hz, 2H), 2.41 (s, 3H), 2.37 (s, 3H) ESI MS (m/z) 598.00 $(M)^+$. |
| 17 | 4-(5-(3,5-dichloro-4-fluorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)-N-(2,2,2-trifluoroethyl)benzamide | $^1$H-NMR (400 MHz, DMSO-$d_6$) δ 7.78 (d, J = 6.4 Hz, 2H), 7.50 (s, 1H), 7.38 (dd, J = 7.9, 1.1 Hz, 1H), 7.08 (d, J = 8.1 Hz, 1H), 4.98 (q, J = 8.8 Hz, 2H), 4.71 (q, J = 9.1 Hz, 2H), 4.22 (t, J = 19.0 Hz, 2H), 2.31 (s, 3H), 2.28 (s, 3H)ESI MS (m/z) 680.00 (M)+. |
| 18 | N-(1-allyl-5-methyl-1H-1,2,4-triazol-3-yl)-4-(5-(3,5-dichloro-4-fluorophenyl)-5-(trifluoromethyl)-4,5-dihydroisoxazol-3-yl)-2-methylbenzamide | $^1$H-NMR (400 MHz, DMSO-$d_6$) δ 10.66 (d, J = 2.7 Hz, 1H), 7.78 (dd, J = 6.2, 1.8 Hz, 2H), 7.57-7.61 (m, 2H), 7.48-7.51 (m, 1H), 5.00-5.02 (m, 2H), 4.32 (dd, J = 26.8, 18.5 Hz, 2H), 3.48 (t, J = 2.6 Hz, 1H), 2.36-2.38 (m, 6H) ESI MS (m/z) 556.00 $(M)^+$. |
| 19 | 4-(5-(3,5-dichloro-4-fluorophenyl)-5-(trifluoromethyl)-4,5-dihydroisoxazol-3-yl)-2-methyl-N-(5-methyl-1-(prop-2-yn-1-yl)-1H-1,2,4-triazol-3-yl)benzamide | $^1$H-NMR (400 MHz, DMSO-$d_6$) δ 10.66 (d, J = 3.2 Hz, 1H), 7.78 (dd, J = 6.1, 1.7 Hz, 2H), 7.57-7.61 (m, 2H), 7.48-7.51 (m, 1H), 5.00-5.02 (m, 2H), 4.32 (dd, J = 26.8, 18.5 Hz, 2H), 3.48 (t, J = 2.6 Hz, 1H), 2.36-2.38 (m, 6H) ESI MS (m/z) 554.00 $(M)^+$. |
| 20 | 4-(5-(3,5-dichloro-4-fluorophenyl)-5-(trifluoromethyl)-4,5-dihydroisoxazol-3-yl)-2-methyl-N-(1-(2,2,2-trifluoroethyl)-5-(trifluoromethyl)-1H-1,2,4-triazol-3-yl)benzamide | $^1$H-NMR (400 MHz, DMSO-$d_6$) δ 11.41 (s, 1H), 7.80 (d, J = 6.4 Hz, 2H), 7.59-7.65 (m, 3H), 5.45 (q, J = 8.6 Hz, 2H), 4.35 (dd, J = 26.9, 18.3 Hz, 2H), 2.41 (s, 3H) ESI MS (m/z) 653.00 $(M + H)^+$. |
| 21 | 4-(5-(3,5-dichloro-4-fluorophenyl)-5-(trifluoromethyl)-4,5-dihydroisoxazol-3-yl)-N-(1-ethyl-5-methyl-1H-1,2,4-triazol-3-yl)-2-methylbenzamide | $^1$H-NMR (400 MHz, DMSO-$d_6$) δ 10.57 (s, 1H), 7.80 (d, J = 6.4 Hz, 2H), 7.60 (d, J = 10.3 Hz, 2H), 7.50 (d, J = 6.8 Hz, 1H), 4.34 (dd, J = 27.0, 18.5 Hz, 2H), 4.02-4.11 (m, 2H), 2.38 (d, J = 13.7 Hz, 6H), 1.28-1.37 (m, 3H) ESI MS (m/z) 544.00 $(M)^+$. |
| 22 | N-(cyclopropylmethyl)-N-(1-(cyclopropylmethyl)-5-methyl-1H-1,2,4-triazol-3-yl)-4-(5-(3,5-dichlorophenyl)-5-(trifluoromethyl)-4,5-dihydroisoxazol-3-yl)-2-methylbenzamide | $^1$H-NMR (400 MHz, DMSO-$d_6$) δ 7.79 (t, J = 1.8 Hz, 1H), 7.62-7.59 (m, 2H), 7.48 (s, 1H), 7.40 (d, J = 8.1 Hz, 1H), 7.08 (d, J = 8.1 Hz, 1H), 4.23 (dd, J = 25.7, 18.3 Hz, 2H), 3.74-3.69 (m, 4H), 2.30 (s, 3H), 2.24 (s, 3H), 1.14-1.08 (m, 1H), 0.75-0.72 (m, 1H), 0.44-0.40 (m, 2H), 0.23 (q, J = 4.8 Hz, 2H), 0.09 (dd, J = 12.3, 5.7 Hz, 2H), −0.05 (q, J = 4.9 Hz, 2H); ESI MS (m/z)608.3(M) 2H+ |
| 23 | 4-(5-(3,5-dichlorophenyl)-5-(trifluoromethyl)-4,5-dihydroisoxazol-3-yl)-N-ethyl-N-(1-ethyl-5-methyl-1H-1,2,4-triazol-3-yl)-2-methylbenzamide | $^1$H-NMR (400 MHz, DMSO-$d_6$) δ 7.79 (t, J = 2.0 Hz, 1H), 7.59 (d, J = 1.7 Hz, 2H), 7.48 (s, 1H), 7.40 (d, J = 7.8 Hz, 1H), 7.08 (d, J = 7.8 Hz, 1H), 4.25 (dd, J = 28.6, 18.3 Hz, 2H), 3.84-3.79 (m, 4H), 2.27 (s, 3H), 2.23 (s, 3H), 1.17 (t, J = 7.1 Hz, 3H), 0.91 (t, J = 7.2 Hz, 3H); ESI MS (m/z) 554.1 (M)+ |
| 24 | N-allyl-N-(1-allyl-5-methyl-1H-1,2,4-triazol-3-yl)-4-(5-(3,5-dichlorophenyl)-5-(trifluoromethyl)-4,5-dihydroisoxazol-3-yl)-2-methylbenzamide | $^1$H-NMR (400 MHz, DMSO-$d_6$) δ 7.80 (t, J = 1.8 Hz, 1H), 7.60 (d, J = 1.7 Hz, 2H), 7.49 (s, 1H), 7.40 (d, J = 8.1 Hz, 1H), 7.10 (d, J = 7.8 Hz, 1H), 5.87 (dq, J = 22.6, 5.3 Hz, 1H), 5.61-5.53 (m, 1H), 5.24 (dd, J = 17.1, 1.5 Hz, 1H), 5.13 (dd, J = 10.4, 1.6 Hz, 1H), 4.74 (d, J = 10.5 Hz, 1H), 4.49 (d, J = 4.6 Hz, 2H), 4.42 (d, J = 4.9 Hz, 2H), 4.31-4.15 (m, 3H), 2.29 (s, 3H), 2.18 (s, 3H),; ESI MS (m/z) 578.4 (M)+ |
| 26 | 4-(5-(3,5-dichloro-4-fluorophenyl)-5-(trifluoromethyl)-4,5-dihydroisoxazol-3-yl)-N-(5-isopropyl-1-methyl-1H-1,2,4-triazol-3-yl)-2-methylbenzamide | $^1$H-NMR (400 MHz, DMSO-$d_6$) δ 10.64 (s, 1H), 7.80 (d, J = 6.1 Hz, 2H), 7.59 (d, J = 11.7 Hz, 2H), 7.51 (d, J = 7.3 Hz, 1H), 4.34 (dd, J = 26.4, 18.3 Hz, 2H), 3.75 (s, 3H), 3.21-3.14 (m, 1H), 2.39 (s, 3H), 1.21 (dd, J = 24.3, 17.5 Hz, 6H) ESI MS (m/z) 558.00 $(M + H)^+$. |

TABLE 1-continued

| Comp. No. | Compound Name | Analytical data |
|---|---|---|
| 27 | 4-(5-(3,5-dichloro-4-fluorophenyl)-5-(trifluoromethyl)-4,5-dihydroisoxazol-3-yl)-N-(5-isopropyl-1-methyl-1H-1,2,4-triazol-3-yl)-N,2-dimethylbenzamide | $^1$H-NMR (400 MHz, DMSO-$d_6$) δ 7.78 (d, J = 6.1 Hz, 2H), 7.47 (s, 1H), 7.39 (d, J = 7.6 Hz, 1H), 7.10 (d, J = 7.8 Hz, 1H), 4.25 (s, 2H), 3.56 (s, 3H), 3.32 (s, 3H), 3.01-2.91 (m, 1H), 2.25 (s, 3H), 0.95 (d, J = 6.6 Hz, 6H) ESI MS (m/z) 572.00 $(M + H)^+$. |
| 28 | 4-(5-(3,5-dichloro-4-fluorophenyl)-5-(trifluoromethyl)-4,5-dihydroisoxazol-3-yl)-N-(1-ethyl-5-(trifluoromethyl)-1H-1,2,4-triazol-3-yl)-2-methylbenzamide | $^1$H-NMR (400 MHz, DMSO-$d_6$) δ 11.19 (s, 1H), 7.80 (d, J = 6.1 Hz, 2H), 7.64-7.61 (m, 2H), 7.57 (d, J = 7.9 Hz, 1H), 4.41-4.30 (m, 4H), 2.41 (s, 3H), 1.41 (t, J = 7.2 Hz, 3H), 1.25-1.21 (m, 1H), ; ESI MS (m/z) 597.9 (M)+ |
| 29 | 4-(5-(3,5-dichlorophenyl)-5-(trifluoromethyl)-4,5-dihydroisoxazol-3-yl)-N-(1-ethyl-5-methyl-1H-1,2,4-triazol-3-yl)-2-methylbenzamide | $^1$H-NMR (400 MHz, DMSO-$d_6$) δ 10.57 (s, 1H), 7.81 (t, J = 2.0 Hz, 1H), 7.62-7.60 (m, 4H), 7.50 (d, J = 7.3 Hz, 1H), 4.41-4.34 (m, 1H), 4.30 (d, J = 18.3 Hz, 1H), 4.05 (q, J = 7.1 Hz, 2H), 2.38 (d, J = 12.8 Hz, 6H), 1.32-1.25 (m, 3H)ESI MS (m/z) 525.9 (M)+ |
| 30 | 4-(5-(3,5-dichloro-4-fluorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methylbenzamide | $^1$H-NMR (400 MHz, DMSO-$d_6$) δ 10.87 (s, 1H), 7.80 (d, J = 6.4 Hz, 2H), 7.61-7.52 (m, 3H), 5.25-5.18 (m, 2H), 4.34 (dd, J = 25.7, 18.3 Hz, 2H), 3.28 (d, J = 7.1 Hz, 1H), 2.90 (s, 1H), 2.39 (s, 3H), 1.21 (d, J = 6.8 Hz, 6H); ESI MS (m/z) 626.0 (M)+ |
| 31 | 4-(5-(3,5-dichloro-4-fluorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methyl-N-(2,2,2-trifluoroethyl)benzamide | $^1$H-NMR (400 MHz, DMSO-$d_6$) δ 7.79 (d, J = 6.4 Hz, 2H), 7.48 (s, 1H), 7.37 (dd, J = 7.9, 1.1 Hz, 1H), 7.07 (d, J = 7.8 Hz, 1H), 5.05 (q, J = 8.8 Hz, 2H), 4.71 (q, J = 9.1 Hz, 2H), 4.20 (dd, J = 26.9, 18.3 Hz, 2H), 3.14-3.07 (m, 1H), 2.26 (s, 3H), 0.99 (dd, J = 6.8, 2.9 Hz, 6H) ESI MS (m/z) 707.00 $(M)^+$. |
| 32 | N-(1-allyl-5-(trifluoromethyl)-1H-1,2,4-triazol-3-yl)-4-(5-(3,5-dichloro-4-fluorophenyl)-5-(trifluoromethyl)-4,5-dihydroisoxazol-3-yl)-2-methylbenzamide | $^1$H-NMR (400 MHz, DMSO-$d_6$) δ 11.22 (s, 1H), 7.81-7.77 (m, 2H), 7.64-7.56 (m, 3H), 6.01 (dq, J = 22.4, 5.3 Hz, 1H), 5.28 (d, J = 10.3 Hz, 1H), 5.14 (d, J = 17.4 Hz, 1H), 4.97 (d, J = 5.4 Hz, 2H), 2.41 (s, 3H), 1.23 (d, J = 11.7 Hz, 1H), 0.85-0.78 (m, 0H)ESI MS (m/z) 610.0 (M)+ |
| 33 | N-(1-allyl-5-(trifluoromethyl)-1H-1,2,4-triazol-3-yl)-4-(5-(3,5-dichlorophenyl)-5-(trifluoromethyl)-4,5-dihydroisoxazol-3-yl)-2-methylbenzamide | $^1$H-NMR (400 MHz, DMSO-$d_6$) δ 11.21 (s, 1H), , 7.65 (d, J = 4.2 Hz, 1H), 7.61 (dd, J = 9.2, 1.8 Hz, 3H), 7.58-7.54 (m, 1H), 6.01 (dq, J = 22.4, 5.3 Hz, 1H), 5.28 (d, J = 10.3 Hz, 1H), 5.14 (d, J = 16.9 Hz, 1H), 4.97 (d, J = 5.4 Hz, 2H), 4.42-4.37 (m, 1H), 4.33-4.25 (m, 1H), ESI MS (m/z) 593.0 (M)+ |
| 34 | 4-(5-(3,5-dichloro-4-fluorophenyl)-5-(trifluoromethyl)-4,5-dihydroisoxazol-3-yl)-N-(1-(2,2-difluoroethyl)-5-(trifluoromethyl)-1H-1,2,4-triazol-3-yl)-2-methylbenzamide | $^1$H-NMR (400 MHz, DMSO-$d_6$) δ 11.32 (s, 1H), 7.80 (d, J = 6.1 Hz, 2H), 7.65-7.58 (m, 3H), 6.48 (tt, J = 53.8, 2.8 Hz, 1H), 4.88 (td, J = 15.1, 2.4 Hz, 2H), 4.35 (dd, J = 26.9, 18.3 Hz, 2H), 2.42 (t, J = 14.7 Hz, 3H), ESI MS (m/z) 634 (M)+ |
| 36 | 4-(5-(3,5-dichloro-4-fluorophenyl)-5-(trifluoromethyl)-4,5-dihydroisoxazol-3-y1)-N-(2,2-difluoroethyl)-N-(1-(2,2-difluoroethyl)-5-(trifluoromethyl)-1H-1,2,4-triazol-3-yl)-2-methylbenzamide | $^1$H-NMR (400 MHz, DMSO-$d_6$) δ 7.78 (d, J = 6.1 Hz, 2H), 7.53 (s, 1H), 7.43 (d, J = 8.1 Hz, 1H), 7.16 (d, J = 8.1 Hz, 1H), 6.52-6.22 (m, 1H), 6.04 (t, J = 53.9 Hz, 1H), 4.73-4.66 (m, 2H), 4.35 (td, J = 14.7, 3.6 Hz, 2H), 4.24 (s, 2H), 2.28 (s, 3H),; ESI MS (m/z) 698.05 (M)+ |
| 37 | 4-(5-(3,5-dichlorophenyl)-5-(trifluoromethyl)-4,5-dihydroisoxazol-3-yl)-N-(1-(2,2-difluoroethyl)-5-(trifluoromethyl)-1H-1,2,4-triazol-3-y1)-2-methylbenzamide | $^1$H-NMR (400 MHz, DMSO-$d_6$) δ 11.32 (s, 1H), 7.81 (t, J = 1.8 Hz, 1H), 7.66-7.58 (m, 5H), 6.62-6.34 (m, 1H), 4.88 (td, J = 15.2, 2.4 Hz, 2H), 4.35 (dd, J = 35.0, 18.3 Hz, 2H), 2.42 (s, 3H),; ESI MS (m/z) 616.0 (M)+ |
| 38 | 4-(5-(3,5-dichlorophenyl)-5-(trifluoromethyl)-4,5-dihydroisoxazol-3-yl)-N-(1,5-diethyl-1H-1,2,4-triazol-3-yl)-2-methylbenzamide | $^1$H-NMR (400 MHz, DMSO-$d_6$) δ 10.61 (s, 1H), 7.81 (t, J = 1.8 Hz, 1H), 7.62-7.50 (m, 5H), 4.34 (dd, J = 34.0, 18.3 Hz, 2H), 4.08-3.99 (m, 2H), 2.72 (q, J = 7.4 Hz, 2H), 2.34 (d, J = 48.7 Hz, 3H), 1.30-1.15 (m, 6H); ESI MS (m/z) 540.04 (M)+ |
| 40 | 4-(5-(3,5-dichloro-4-fluorophenyl)-5-(trifluoromethyl)-4,5-dihydroisoxazol-3-yl)-N,2-dimethyl-N-(1-methyl-5-(trifluoromethyl)-1H-1,2,4-triazol-3-yl)benzamide | $^1$H-NMR (400 MHz, DMSO-$d_6$) δ 7.78 (d, J = 6.1 Hz, 2H), 7.54 (s, 1H), 7.46 (d, J = 8.1 Hz, 1H), 7.19 (d, J = 8.1 Hz, 1H), 4.29 (dd, J = 25.1, 18.5 Hz, 2H), 3.83 (d, J = 1.0 Hz, 3H), 3.36 (s, 3H), 2.27 (s, 3H); ESI MS (m/z) 598.0 (M)+ |
| 41 | N-(1-(cyanomethyl)-5-(trifluoromethyl)-1H-1,2,4-triazol-3-yl)-4-(5-(3,5-dichloro-4-fluorophenyl)-5-(trifluoromethyl)-4,5-dihydroisoxazol-3-yl)-2-methylbenzamide | $^1$H-NMR (400 MHz, DMSO-$d_6$) δ 11.44 (s, 1H), 7.85-7.78 (m, 2H), 7.70-7.58 (m, 3H), 5.80 (s, 2H), 4.36 (dd, J = 26.9, 18.3 Hz, 2H), 2.44 (d, J = 18.0 Hz, 3H), ; ESI MS (m/z) 607.25 (M) − 2 |

TABLE 1-continued

| Comp. No. | Compound Name | Analytical data |
|---|---|---|
| 42 | 4-(5-(3,5-dichloro-4-fluorophenyl)-5-(trifluoromethyl)-4,5-dihydroisoxazol-3-yl)-2-methyl-N-(1-methyl-5-phenyl-1H-1,2,4-triazol-3-yl)benzamide | $^1$H-NMR (400 MHz, DMSO-$d_6$)$^1$H-NMR (400 MHz, DMSO-$d_6$) δ 10.85 (s, 1H), 7.81 (d, J = 6.1 Hz, 1H), 7.76 (t, J = 3.4 Hz, 2H), 7.62 (d, J = 9.8 Hz, 2H), 7.56-7.48 (m, 5H), 4.45-4.30 (m, 2H), 3.93 (s, 3H), 2.43 (s, 3H); ESI MS (m/z) 592.3 (M)+ |
| 43 | 4-(5-(3,5-dichloro-4-fluorophenyl)-5-(trifluoromethyl)-4,5-dihydroisoxazol-3-yl)-N,2-dimethyl-N-(1-methyl-5-phenyl-1H-1,2,4-triazol-3-yl)benzamide | $^1$H-NMR (400 MHz, DMSO-$d_6$) δ 7.80 (q, J = 6.5 Hz, 2H), 7.57-7.40 (m, 7H), 7.22 (d, J = 7.9 Hz, 1H), 4.39-4.23 (m, 2H), 3.78 (d, J = 17.1 Hz, 3H), 3.40 (s, 3H), 2.30 (s, 3H); ESI MS (m/z) 606.3 (M)+ |
| 44 | 4-(5-(3,5-dichloro-4-fluorophenyl)-5-(trifluoromethyl)-4,5-dihydroisoxazol-3-yl)-N-ethyl-N-(1-ethyl-5-(trifluoromethyl)-1H-1,2,4-triazol-3-yl)-2-methylbenzamide | $^1$H-NMR (400 MHz, DMSO-$d_6$) δ 7.77 (d, J = 6.1 Hz, 2H), 7.52 (s, 1H), 7.43 (d, J = 8.1 Hz, 1H), 7.13 (d, J = 7.8 Hz, 1H), 4.26 (t, J = 19.0 Hz, 2H), 4.10 (q, J = 7.2 Hz, 2H), 3.88 (q, J = 6.9 Hz, 2H), 2.27 (s, 3H), 1.21 (t, J = 7.1 Hz, 3H), 1.04-0.97 (m, 3H); ESI MS (m/z) 626.0 (M)+ |
| 45 | 4-(5-(3,5-dichloro-4-fluorophenyl)-5-(trifluoromethyl)-4,5-dihydroisoxazol-3-yl)-2-methyl-N-(1-(prop-2-yn-1-yl)-5-(trifluoromethyl)-1H-1,2,4-triazol-3-yl)benzamide | $^1$H-NMR (400 MHz, DMSO-$d_6$) δ 11.28 (s, 1H), 7.80 (d, J = 6.1 Hz, 2H), 7.65-7.58 (m, 3H), 5.29 (d, J = 2.2 Hz, 2H), 4.36 (dd, J = 27.0, 18.5 Hz, 2H), 3.66 (t, J = 2.6 Hz, 1H), 2.42 (s, 3H) |
| 46 | 4-(5-(3,5-dichloro-4-fluorophenyl)-5-(trifluoromethyl)-4,5-dihydroisoxazol-3-yl)-N-(5-(1,1-difluoroethyl)-1-methyl-1H-1,2,4-triazol-3-yl)-N,2-dimethylbenzamide | $^1$H-NMR (400 MHz, DMSO-$d_6$) δ 7.78 (d, J = 6.1 Hz, 2H), 7.53 (s, 1H), 7.44 (d, J = 7.8 Hz, 1H), 7.16 (d, J = 8.1 Hz, 1H), 4.28 (dd, J = 24.1, 18.5 Hz, 2H), 3.77 (s, 3H), 3.36 (s, 3H), 2.26 (s, 3H), 1.85 (t, J = 19.6 Hz, 3H) ESI MS (m/z) 594.00 $(M + H)^+$. |
| 47 | 4-(5-(3,5-dichloro-4-fluorophenyl)-5-(trifluoromethyl)-4,5-dihydroisoxazol-3-yl)-N-(5-(1,1-difluoroethyl)-1-methyl-1H-1,2,4-triazol-3-yl)-2-methylbenzamide | $^1$H-NMR (400 MHz, DMSO-$d_6$) δ 10.97 (s, 1H), 7.80 (d, J = 6.1 Hz, 2H), 7.67-7.54 (m, 3H), 4.35 (dd, J = 26.9, 18.3 Hz, 2H), 3.96 (s, 3H), 2.40 (s, 3H), 2.11 (t, J = 19.6 Hz, 3H) ESI MS (m/z) 580.00 $(M + H)^+$. |
| 48 | 4-(5-(3,5-dichlorophenyl)-5-(trifluoromethyl)-4,5-dihydroisoxazol-3-yl)-N-(5-(1,1-difluoroethyl)-1-methyl-1H-1,2,4-triazol-3-yl)-2-methylbenzamide | $^1$H-NMR (400 MHz, DMSO-$d_6$) δ 10.97 (s, 1H), 7.81 (t, J = 2.0 Hz, 1H), 7.66-7.62 (m, 4H), 7.54 (d, J = 7.8 Hz, 1H), 4.39 (d, J = 18.3 Hz, 1H), 4.31 (d, J = 18.6 Hz, 1H), 3.96 (s, 3H), 2.40 (s, 3H), 2.11 (t, J = 19.6 Hz, 3H) ESI MS (m/z) 561.00 $(M)^+$. |
| 49 | 4-(5-(3,5-dichlorophenyl)-5-(trifluoromethyl)-4,5-dihydroisoxazol-3-yl)-N-(5-(1,1-difluoroethyl)-1-methyl-1H-1,2,4-triazol-3-yl)-N,2-dimethylbenzamide | $^1$H-NMR (400 MHz, DMSO-$d_6$) δ 7.80 (t, J = 2.0 Hz, 1H), 7.60 (d, J = 1.7 Hz, 2H), 7.54 (s, 1H), 7.45 (d, J = 8.1 Hz, 1H), 7.16 (d, J = 8.1 Hz, 1H), 4.28 (dd, J = 31.7, 18.5 Hz, 2H), 3.77 (s, 3H), 3.36 (s, 3H), 2.26 (s, 3H), 1.85 (t, J = 19.4 Hz, 3H) ESI MS (m/z) 576.00 $(M + H)^+$. |
| 50 | N-(1-(cyanomethyl)-5-(trifluoromethyl)-1H-1,2,4-triazol-3-yl)-4-(5-(3,5-dichlorophenyl)-5-(trifluoromethyl)-4,5-dihydroisoxazol-3-yl)-2-methylbenzamide | $^1$H-NMR (400 MHz, DMSO-$d_6$) δ 11.18 (s, 1H), 7.81 (t, J = 1.8 Hz, 1H), 7.65-7.56 (m, 5H), 4.42-4.28 (m, 4H), 2.44 (d, J = 19.1 Hz, 3H), 1.41 (t, J = 7.2 Hz, 3H), |
| 51 | 4-(5-(3,5-dichlorophenyl)-5-(trifluoromethyl)-4,5-dihydroisoxazol-3-yl)-2-methyl-N-(1-(2,2,2-trifluoroethyl)-5-(trifluoromethyl)-1H-1,2,4-triazol-3-yl)benzamide | $^1$H-NMR (400 MHz, DMSO-$d_6$) δ 7.72 (t, J = 1.8 Hz, 1H), 7.67 (d, J = 2.1 Hz, 2H), 7.52 (s, 1H), 7.25 (s, 1H), 6.87 (s, 1H), 3.90 (s, 3H), |
| 52 | 4-(5-(3,5-dichlorophenyl)-5-(trifluoromethyl)-4,5-dihydroisoxazol-3-yl)-N-(1-(2-methoxyethyl)-5-(trifluoromethyl)-1H-1,2,4-triazol-3-yl)-2-methylbenzamide | $^1$H-NMR (400 MHz, DMSO-d6) 8 11.20 (s, 1H), 7.81 (t, J = 2.0 Hz, 1H), 7.65-7.62 (m, 4H), 7.57 (d, J = 7.9 Hz, 1H), 4.45 (t, J = 4.9 Hz, 2H), 4.40 (d, J = 18.3 Hz, 1H), 4.31 (d, J = 18.3 Hz, 1H), 3.71 (d, J = 4.3 Hz, 2H), 3.21 (d, J = 4.9 Hz, 3H), 2.41 (s, 3H) |
| 53 | 4-(5-(3,5-dichlorophenyl)-5-(trifluoromethyl)-4,5-dihydroisoxazol-3-yl)-N-(1-ethyl-5-(trifluoromethyl)-1H-1,2,4-triazol-3-yl)-2-methylbenzamide | $^1$H-NMR (400 MHz, DMSO-$d_6$) δ 11.19 (s, 1H), 7.81 (t, J = 2.0 Hz, 1H), 7.65-7.62 (m, 4H), 7.57 (d, J = 7.9 Hz, 1H), 4.42-4.29 (m, 4H), 2.41 (s, 3H), 1.41 (t, J = 7.2 Hz, 3H), |
| 54 | 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-(trifluoromethyl)-1H-1,2,4-triazol-3-y1)-2-methylbenzamide | $^1$H-NMR (400 MHz, DMSO-$d_6$) δ 7.80 (t, J = 1.8 Hz, 1H), 7.60 (d, J = 1.5 Hz, 2H), 7.54 (s, 1H), 7.45-7.43 (m, 1H), 7.15 (d, J = 7.9 Hz, 1H), 6.37 (tt, J = 55.3, 3.8 Hz, 1H), 6.17-5.89 (m, 1H), 4.69 (td, J = 15.1, 2.3 Hz, 2H), 4.35 (td, J = 14.8, 3.7 Hz, 2H), 4.24 (dd, J = 20.5, 18.6 Hz, 2H), 2.29 (d, J = 15.0 Hz, 3H), |
| 55 | 4-(5-(3,5-dichlorophenyl)-5-(trifluoromethyl)-4,5-dihydroisoxazol-3-yl)-N-(5-(1,1-difluoroethyl)-1-(2,2,2-trifluoroethyl)-1H-1,2,4-triazol-3-yl)-2-methylbenzamide | $^1$H-NMR (400 MHz, DMSO-$d_6$) δ 11.22 (s, 1H), 7.81 (t, J = 1.8 Hz, 1H), 7.70-7.56 (m, 5H), 5.30 (q, J = 8.6 Hz, 2H), 4.39 (d, J = 18.3 Hz, 1H), 4.31 (d, J = 18.3 Hz, 1H), 2.41 (s, 3H), 2.18-1.98 (m, 3H) ESI MS (m/z) 630.00 $(M + H)^+$. |

TABLE 1-continued

| Comp. No. | Compound Name | Analytical data |
|---|---|---|
| 56 | 4-(5-(3,5-dichloro-4-fluorophenyl)-5-(trifluoromethyl)-4,5-dihydroisoxazol-3-yl)-N-(5-(1,1-difluoroethyl)-1-(2,2-difluoroethyl)-1H-1,2,4-triazol-3-yl)-2-methylbenzamide | $^1$H-NMR (400 MHz, DMSO-$d_6$) δ 11.14 (s, 1H), 7.80 (d, J = 6.1 Hz, 2H), 7.64-7.56 (m, 3H), 6.59-6.30 (m, 1H), 4.79 (td, J = 14.4, 3.3 Hz, 2H), 4.35 (dd, J = 26.7, 18.3 Hz, 2H), 2.41 (s, 3H), 2.17-2.02 (m, 3H) ESI MS (m/z) 630.00 (M + H)$^+$. |
| 57 | 4-(5-(3,5-dichlorophenyl)-5-(trifluoromethyl)-4,5-dihydroisoxazol-3-yl)-N-(5-(1,1-difluoroethyl)-1-(2,2-difluoroethyl)-1H-1,2,4-triazol-3-yl)-2-methylbenzamide | $^1$H-NMR (400 MHz, DMSO-$d_6$) δ 11.14 (s, 1H), 7.81 (t, J = 1.8 Hz, 1H), 7.69-7.55 (m, 5H), 6.58-6.30 (m, 1H), 4.83-4.74 (m, 2H), 4.44-4.28 (m, 2H), 2.41 (s, 3H), 2.22-1.97 (m, 3H) ESI MS (m/z) 612.00 (M + H)$^+$. |
| 58 | 4-(5-(3,5-dichloro-4-fluorophenyl)-5-(trifluoromethyl)-4,5-dihydroisoxazol-3-yl)-N-(5-(1,1-difluoroethyl)-1-(2,2,2-trifluoroethyl)-1H-1,2,4-triazol-3-yl)-2-methylbenzamide | $^1$H-NMR (400 MHz, DMSO-$d_6$) δ 11.22 (s, 1H), 7.80 (d, J = 6.4 Hz, 2H), 7.64-7.57 (m, 3H), 5.30 (q, J = 8.6 Hz, 2H), 4.35 (dd, J = 26.2, 18.3 Hz, 2H), 2.41 (s, 3H), 2.14 (t, J = 19.6 Hz, 3H) ESI MS (m/z) 648.00 (M + H)$^+$. |
| 59 | 4-(5-(3,5-dichlorophenyl)-5-(trifluoromethyl)-4,5-dihydroisoxazol-3-yl)-N-(2,2-difluoroethyl)-N-(5-(1,1-difluoroethyl)-1-(2,2-difluoroethyl)-1H-1,2,4-triazol-3-yl)-2-methylbenzamide | $^1$H-NMR (400 MHz, DMSO-$d_6$) δ 7.82 (t, J = 1.8 Hz, 1H), 7.62 (d, J = 1.7 Hz, 2H), 7.56 (s, 1H), 7.47-7.45 (m, 1H), 7.16 (d, J = 8.1 Hz, 1H), 6.40 (tt, J = 55.5, 4.0 Hz, 1H), 6.00 (tt, J = 54.5, 3.4 Hz, 1H), 4.61 (td, J = 14.3, 3.5 Hz, 2H), 4.40-4.21 (m, 4H), 2.28 (s, 3H), 1.90 (t, J = 19.4 Hz, 3H) ESI MS (m/z) 676.00 (M + H)$^+$. |
| 61 | 4-(5-(3,5-dichlorophenyl)-5-(trifluoromethyl)-4,5-dihydroisoxazol-3-yl)-N-(5-(1,1-difluoroethyl)-1-(prop-2-yn-1-yl)-1H-1,2,4-triazol-3-yl)-2-methylbenzamide | $^1$H-NMR (400 MHz, DMSO-$d_6$) δ 11.10 (s, 1H), 7.81 (t, J = 2.0 Hz, 1H), 7.65-7.62 (m, 4H), 7.56 (d, J = 7.8 Hz, 1H), 5.18 (d, J = 2.4 Hz, 2H), 4.35 (dd, J = 35.2, 18.3 Hz, 2H), 3.56 (t, J = 2.4 Hz, 1H), 2.41 (s, 3H), 2.12 (t, J = 19.4 Hz, 3H) ESI MS (m/z) 586.00 (M + H)$^+$. |
| 62 | 4-(5-(3,5-dichlorophenyl)-5-(trifluoromethyl)-4,5-dihydroisoxazol-3-y1)-N-(5-(1,1-difluoroethyl)-1-ethyl-1H-1,2,4-triazol-3-yl)-2-methylbenzamide | $^1$H-NMR (400 MHz, DMSO-$d_6$) δ 10.98 (s, 1H), 7.81 (t, J = 1.8 Hz, 1H), 7.64-7.61 (m, 4H), 7.55 (d, J = 7.8 Hz, 1H), 4.41-4.27 (m, 4H), 2.41 (s, 3H), 2.12 (t, J = 19.6 Hz, 3H), 1.38 (t, J = 7.1 Hz, 3H) ESI MS (m/z) 576.00 (M + H)$^+$. |
| 63 | 4-(5-(3,5-dichloro-4-fluorophenyl)-5-(trifluoromethyl)-4,5-dihydroisoxazol-3-yl)-N-(1,5-diethyl-1H-1,2,4-triazol-3-yl)-2-methylbenzamide | $^1$H-NMR (400 MHz, DMSO-$d_6$) δ 10.62 (s, 1H), 7.80 (d, J = 6.1 Hz, 2H), 7.60 (d, J = 11.2 Hz, 2H), 7.51 (d, J = 7.3 Hz, 1H), 4.34 (dd, J = 25.9, 18.3 Hz, 2H), 4.06 (q, J = 7.1 Hz, 2H), 2.72 (q, J = 7.5 Hz, 2H), 2.40 (s, 3H), 1.32-1.26 (m, 3H), 1.22-1.16 (m, 3H) |
| 64 | 4-(5-(3,5-dichloro-4-fluorophenyl)-5-(trifluoromethyl)-4,5-dihydroisoxazol-3-yl)-N-(1,5-diethyl-1H-1,2,4-triazol-3-yl)-N-ethyl-2-methylbenzamide | $^1$H-NMR (400 MHz, DMSO-$d_6$) δ 7.77 (d, J = 6.4 Hz, 2H), 7.46 (s, 1H), 7.38 (d, J = 8.1 Hz, 1H), 7.08 (d, J = 7.8 Hz, 1H), 4.24 (s, 2H), 3.86-3.79 (m, 4H), 2.56 (q, J = 7.5 Hz, 2H), 2.27 (s, 3H), 1.22-1.16 (m, 3H), 1.01 (t, J = 7.5 Hz, 3H), 0.92 (t, J = 7.1 Hz, 3H) |
| 65 | N-(1-(cyclopropylmethyl)-5-(trifluoromethyl)-1H-1,2,4-triazol-3-yl)-4-(5-(3,5-dichloro-4-fluorophenyl)-5-(trifluoromethyl)-4,5-dihydroisoxazol-3-yl)-2-methylbenzamide | H-NMR (400 MHz, DMSO-$D_6$) δ 11.18 (s, 1H), 7.80 (d, J = 6.1 Hz, 2H), 7.64-7.57 (m, 3H), 4.35 (dd, J = 26.4, 18.3 Hz, 2H), 4.18 (d, J = 7.3 Hz, 2H), 2.44 (d, J = 18.3 Hz, 3H), 1.27-1.22 (m, 1H), 0.56 (d, J = 6.8 Hz, 2H), 0.41 (d, J = 4.4 Hz, 2H); ESI MS (m/z) 625.45(M) + H |
| 66 | 4-(5-(3,5-dichloro-4-fluorophenyl)-5-(trifluoromethyl)-4,5-dihydroisoxazol-3-yl)-2-methyl-N-(1-(2,2,3,3,3-pentafluoropropyl)-5-(trifluoromethyl)-1H-1,2,4-triazol-3-yl)benzamide | $^1$H-NMR (400 MHz, DMSO-$d_6$) δ 11.42 (s, 1H), 7.80 (d, J = 6.4 Hz, 2H), 7.65-7.59 (m, 3H), 5.49 (t, J = 15.0 Hz, 2H), 4.35 (dd, J = 26.0, 18.5 Hz, 2H), 2.41 (s, 3H) ESI MS (m/z) 700.00 (M − H)$^-$. |
| 67 | 4-(5-(3,5-dichlorophenyl)-5-(trifluoromethyl)-4,5-dihydroisoxazol-3-yl)-N-(5-(fluoromethyl)-1-methyl-1H-1,2,4-triazol-3-yl)-2-methylbenzamide | $^1$H-NMR (400 MHz, DMSO-$d_6$) δ 10.80 (s, 1H), 7.81 (t, J = 1.8 Hz, 1H), 7.64-7.62 (m, 4H), 7.53 (d, J = 7.8 Hz, 1H), 5.57 (d, J = 47.4 Hz, 2H), 4.35 (dd, J = 34.8, 18.5 Hz, 2H), 3.88 (s, 3H), 2.40 (s, 3H) ESI MS (m/z) 529.00 (M + H)$^+$. |
| 68 | 4-(5-(3,5-dichloro-4-fluorophenyl)-5-(trifluoromethyl)-4,5-dihydroisoxazol-3-yl)-N-(5-(1,1-difluoroethyl)-1-(prop-2-yn-1-yl)-1H-1,2,4-triazol-3-yl)-2-methylbenzamide | $^1$H-NMR (400 MHz, DMSO-$d_6$) δ 11.10 (s, 1H), 7.80 (d, J = 6.1 Hz, 2H), 7.64-7.56 (m, 3H), 5.18 (d, J = 2.4 Hz, 2H), 4.35 (dd, J = 27.1, 18.3 Hz, 2H), 3.56 (t, J = 2.6 Hz, 1H), 2.41 (s, 3H), 2.12 (t, J = 19.6 Hz, 3H) ESI MS (m/z) 604.00 (M + H)$^+$. |
| 69 | 4-(5-(3,5-dichlorophenyl)-5-(trifluoromethyl)-4,5-dihydroisoxazol-3-yl)-N-(5-isopropyl-1-methyl-1H-1,2,4-triazol-3-yl)-2-methylbenzamide | $^1$H-NMR (400 MHz, DMSO-$d_6$) δ 10.64 (s, 1H), 7.81 (t, J = 1.8 Hz, 1H), 7.62-7.59 (m, 4H), 7.50 (d, J = 7.6 Hz, 1H), 4.34 (dd, J = 34.6, 18.5 Hz, 2H), 3.75 (s, 3H), 3.21-3.14 (m, 1H), 2.39 (s, 3H), 1.23 (dd, J = 16.9, 6.8 Hz, 6H) ESI MS (m/z) 538.00 (M − H)–. |

TABLE 1-continued

| Comp. No. | Compound Name | Analytical data |
|---|---|---|
| 70 | 4-(5-(3,5-dichloro-4-fluorophenyl)-5-(trifluoromethyl)-4,5-dihydroisoxazol-3-yl)-N-(5-(1,1-difluoroethyl)-1-ethyl-1H-1,2,4-triazol-3-yl)-2-methylbenzamide | $^1$H-NMR (400 MHz, DMSO-$d_6$) δ 10.98 (s, 1H), 7.80 (d, J = 6.4 Hz, 2H), 7.63-7.60 (m, 2H), 7.55 (d, J = 7.6 Hz, 1H), 4.41-4.27 (m, 4H), 2.41 (s, 3H), 2.12 (t, J = 19.7 Hz, 3H), 1.38 (t, J = 7.2 Hz, 3H) ESI MS (m/z) 594.00 $(M + H)^+$. |
| 71 | 4-(5-(3,5-dichlorophenyl)-5-(trifluoromethyl)-4,5-dihydroisoxazol-3-yl)-N-(5-isopropyl-1-methyl-1H-1,2,4-triazol-3-yl)-N,2-dimethylbenzamide | $^1$H-NMR (400 MHz, DMSO-$d_6$) δ 7.80 (t, J = 1.8 Hz, 1H), 7.60 (d, J = 1.5 Hz, 2H), 7.48 (s, 1H), 7.40 (d, J = 7.9 Hz, 1H), 7.10 (d, J = 7.9 Hz, 1H), 4.25 (dd, J = 26.3, 18.3 Hz, 2H), 3.56 (s, 3H), 3.32 (s, 3H), 3.01-2.91 (m, 1H), 2.25 (s, 3H), 0.95 (d, J = 6.7 Hz, 6H) ESI MS (m/z) 554.00 $(M + H)^+$. |
| 72 | 4-(5-(3,5-dichlorophenyl)-5-(trifluoromethyl)-4,5-dihydroisoxazol-3-y1)-N-(1-(2,2-difluoroethyl)-5-isopropyl-1H-1,2,4-triazol-3-yl)-2-methylbenzamide | $^1$H-NMR (400 MHz, DMSO-$d_6$) δ 10.81 (s, 1H), 7.81 (t, J = 1.8 Hz, 1H), 7.62-7.51 (m, 5H), 6.51-6.23 (m, 1H), 4.66 (td, J = 14.9, 3.0 Hz, 2H), 4.34 (dd, J = 34.0, 18.3 Hz, 2H), 3.27-3.20 (m, 1H), 2.40 (s, 3H), 1.22-1.08 (m, 6H) ESI MS (m/z) 588.00 $(M - H)^-$. |
| 73 | 4-(5-(3,5-dichlorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methylbenzamide | $^1$H-NMR (400 MHz, DMSO-$d_6$) δ 10.87 (s, 1H), 7.81 (t, J = 1.8 Hz, 1H), 7.62-7.59 (m, 4H), 7.53 (d, J = 7.8 Hz, 1H), 5.22 (q, J = 9.0 Hz, 2H), 4.34 (dd, J = 33.9, 18.5 Hz, 2H), 3.27 (t, J = 6.7 Hz, 1H), 2.39 (s, 3H), 1.21 (d, J = 6.6 Hz, 6H) ESI MS (m/z) 608.00 $(M + H)^+$. |
| 74 | 4-(5-(3,5-dichloro-4-fluorophenyl)-5-(trifluoromethyl)-4,5-dihydroisoxazol-3-yl)-N-(5-(fluoromethyl)-1-methyl-1H-1,2,4-triazol-3-y1)-2-methylbenzamide | $^1$H-NMR (400 MHz, DMSO-$d_6$) δ 10.81 (s, 1H), 7.80 (d, J = 3.7 Hz, 2H), 7.63-7.54 (m, 3H), 5.58 (d, J = 47.4 Hz, 2H), 4.35 (dd, J = 24.9, 18.3 Hz, 2H), 3.88 (s, 3H), 2.41 (s, 3H) |
| 75 | 4-(5-(3,5-dichlorophenyl)-5-(trifluoromethyl)-4,5-dihydroisoxazol-3-yl)-N-(5-isobutyl-1-methyl-1H-1,2,4-triazol-3-yl)-N,2-dimethylbenzamide | $^1$H-NMR (400 MHz, DMSO-$d_6$) δ 7.77 (t, J = 2.0 Hz, 1H), 7.58 (d, J = 1.7 Hz, 2H), 7.45 (s, 1H), 7.36 (d, J = 8.1 Hz, 1H), 7.08 (d, J = 8.1 Hz, 1H), 4.20 (dd, J = 23.4, 18.5 Hz, 2H), 3.54 (s, 3H), 3.29 (s, 3H), 2.35 (d, J = 7.1 Hz, 2H), 2.24 (s, 3H), 1.65-1.59 (m, 1H), 0.53 (d, J = 5.9 Hz, 6H) ESI MS (m/z) 568.00 $(M + H)^+$. |
| 76 | 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-isopropyl-1H-1,2,4-triazol-3-yl)-2-methylbenzamide | $^1$H-NMR (400 MHz, DMSO-$d_6$) δ 7.80 (t, J = 2.0 Hz, 1H), 7.60 (d, J = 1.7 Hz, 2H), 7.49 (s, 1H), 7.42-7.39 (m, 1H), 7.10 (d, J = 7.8 Hz, 1H), 6.36 (tt, J = 55.8, 4.1 Hz, 1H), 5.92 (tt, J = 54.8, 3.5 Hz, 1H), 4.48 (td, J = 14.7, 3.6 Hz, 2H), 4.34-4.22 (m, 4H), 3.06-2.99 (m, 1H), 2.25 (s, 3H), 0.96 (dd, J = 6.8, 2.2 Hz, 6H) ESI MS (m/z) 655.00 $(M + 2H)^+$. |
| 77 | 4-(5-(3,5-dichlorophenyl)-5-(trifluoromethyl)-4,5-dihydroisoxazol-3-yl)-N-(5-isobutyl-1-methyl-1H-1,2,4-triazol-3-yl)-2-methylbenzamide | $^1$H-NMR (400 MHz, DMSO-$d_6$) δ 10.32 (s, 1H), 7.73-7.72 (m, 1H), 7.62-7.58 (m, 4H), 7.48 (d, J = 7.6 Hz, 1H), 4.32 (d, J = 18.3 Hz, 1H), 4.24 (d, J = 18.3 Hz, 1H), 3.72 (s, 3H), 2.58-2.53 (m, 2H), 2.41 (s, 3H), 2.06-1.99 (m, 1H), 0.95-0.91 (m, 6H) ESI MS (m/z) 554.00 $(M + H)^+$. |
| 78 | 4-(5-(3,5-dichlorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methyl-N-(2,2,2-trifluoroethyl)benzamide | $^1$H-NMR (400 MHz, DMSO-$d_6$) δ 7.80 (t, J = 1.8 Hz, 1H), 7.63-7.60 (m, 2H), 7.49 (s, 1H), 7.39-7.37 (m, 1H), 7.07 (d, J = 7.8 Hz, 1H), 5.05 (q, J = 8.8 Hz, 2H), 4.71 (q, J = 9.1 Hz, 2H), 4.24-4.15 (m, 2H), 3.14-3.07 (m, 1H), 2.26 (s, 3H), 0.99 (q, J = 3.3 Hz, 6H) ESI MS (m/z) 690.00 $(M + H)^+$. |
| 79 | 4-(5-(3,5-dichlorophenyl)-5-(trifluoromethyl)-4,5-dihydroisoxazol-3-yl)-2-methyl-N-(1-methyl-5-(3,3,3-trifluoropropyl)-1H-1,2,4-triazol-3-yl)benzamide | $^1$H-NMR (400 MHz, DMSO-$d_6$) δ 10.67 (s, 1H), 7.81 (t, J = 2.0 Hz, 1H), 7.62-7.60 (m, 4H), 7.50 (d, J = 7.6 Hz, 1H), 4.34 (dd, J = 34.2, 18.3 Hz, 2H), 3.76 (s, 3H), 3.00 (t, J = 7.8 Hz, 2H), 2.70 (q, J = 9.2 Hz, 2H), 2.37 (d, J = 13.0 Hz, 3H) ESI MS (m/z) 594.00 $(M + H)^+$. |
| 80 | 4-(5-(3,5-dichlorophenyl)-5-(trifluoromethyl)-4,5-dihydroisoxazol-3-yl)-N-(1-ethyl-5-isopropyl-1H-1,2,4-triazol-3-yl)-2-methylbenzamide | $^1$H-NMR (400 MHz, DMSO-$d_6$) δ 10.65 (s, 1H), 7.81 (t, J = 2.0 Hz, 1H), 7.62-7.59 (m, 4H), 7.51 (d, J = 6.8 Hz, 1H), 4.34 (dd, J = 34.1, 18.5 Hz, 2H), 4.09 (d, J = 6.8 Hz, 2H), 3.21-3.15 (m, 1H), 2.42-2.36 (m, 3H), 1.32 (s, 3H), 1.22-1.16 (m, 6H) ESI MS (m/z) 554.00 $(M + H)^+$. |
| 81 | 4-(5-(3,5-dichlorophenyl)-5-(trifluoromethyl)-4,5-dihydroisoxazol-3-yl)-2-methyl-N-(1-(2,2,2-trifluoroethyl)-5-(3,3,3-trifluoropropyl)-1H-1,2,4-triazol-3-yl)benzamide | $^1$H-NMR (400 MHz, DMSO-$d_6$) δ 10.91 (s, 1H), 7.81 (t, J = 1.8 Hz, 1H), 7.62-7.60 (m, 4H), 7.53 (d, J = 7.6 Hz, 1H), 5.26 (q, J = 8.8 Hz, 2H), 4.34 (dd, J = 33.6, 18.5 Hz, 2H), 3.07 (t, J = 7.7 Hz, 2H), 2.74 (dd, J = 17.2, 9.2 Hz, 2H), 2.39 (s, 3H) ESI MS (m/z) 662.00 $(M + H)^+$. |
| 82 | 4-(5-(3,5-dichlorophenyl)-5-(trifluoromethyl)-4,5-dihydroisoxazol-3-yl)-N,2-dimethyl-N-(1-methyl-5-(3,3,3-trifluoropropyl)-1H-1,2,4-triazol-3-yl)benzamide | $^1$H-NMR (400 MHz, DMSO-$d_6$) δ 7.81-7.79 (m, 1H), 7.60 (d, J = 1.7 Hz, 2H), 7.49 (s, 1H), 7.42 (d, J = 8.1 Hz, 1H), 7.12 (d, J = 8.1 Hz, 1H), 4.23 (dd, J = 26.7, 18.3 Hz, 2H), 3.58 (s, 3H), 3.32 (s, 3H), 2.81 (t, J = 7.6 Hz, 2H), 2.42-2.30 (m, 2H), 2.24 (s, 3H) ESI MS (m/z) 608.00 $(M + H)^+$. |
| 83 | 4-(5-(3,5-dichlorophenyl)-5-(trifluoromethyl)-4,5-dihydroisoxazol-3-yl)-2-methyl-N-(2,2,2-trifluoroethyl)-N-(1-(2,2,2- | $^1$H-NMR (400 MHz, DMSO-$d_6$) δ 7.89 (d, J = 8.1 Hz, 0H), 7.80 (q, J = 1.9 Hz, 1H), 7.67 (d, J = 8.8 Hz, 0H), 7.60 (d, J = 1.7 Hz, 2H), 7.51 (s, 1H), 7.40 (dd, J = 7.9, 1.1 Hz, 1H), 7.08 (d, J = 7.8 Hz, 1H), 5.09 (q, J = 8.8 Hz, |

TABLE 1-continued

| Comp. No. | Compound Name | Analytical data |
|---|---|---|
| | trifluoroethyl)-5-(3,3,3-trifluoropropyl)-1H-1,2,4-triazol-3-yl)benzamide | 2H), 4.73 (q, J = 9.1 Hz, 2H), 4.17 (d, J = 18.3 Hz, 2H), 3.84 (s, 0H), 2.93 (t, J = 7.3 Hz, 2H), 2.54-2.51 (m, 0H), 2.47-2.39 (m, 2H), 2.29 (d, J = 22.7 Hz, 3H) ESI MS (m/z) 743.00 $(M)^+$. |
| 84 | 4-(5-(3,5-dichlorophenyl)-5-(trifluoromethyl)-4,5-dihydroisoxazol-3-yl)-2-methyl-N-(1-methyl-5-(2,2,2-trifluoroethyl)-1H-1,2,4-triazol-3-yl)benzamide | $^1$H-NMR (400 MHz, DMSO-$d_6$) δ 10.82 (s, 1H), 7.81 (t, J = 1.7 Hz, 1H), 7.62-7.60 (m, 4H), 7.52 (d, J = 7.6 Hz, 1H), 4.35 (dd, J = 34.6, 18.5 Hz, 2H), 4.10 (q, J = 10.8 Hz, 2H), 3.84 (s, 3H), 2.39 (s, 3H) ESI MS (m/z) 580.00 $(M + H)^+$. |
| 85 | 4-(5-(3,5-dichlorophenyl)-5-(trifluoromethyl)-4,5-dihydroisoxazol-3-yl)-N-(1-(2,2-difluoroethyl)-5-(3,3,3-trifluoropropyl)-1H-1,2,4-triazol-3-yl)-2-methylbenzamide | $^1$H-NMR (400 MHz, DMSO-$d_6$) δ 10.84 (s, 1H), 7.81 (t, J = 1.8 Hz, 1H), 7.62-7.60 (m, 4H), 7.52 (d, J = 7.8 Hz, 1H), 6.38 (t, J = 54.5 Hz, 1H), 4.73-4.66 (m, 2H), 4.34 (dd, J = 34.0, 18.3 Hz, 2H), 3.06-3.02 (m, 2H), 2.72 (t, J = 9.4 Hz, 2H), 2.39 (s, 3H) ESI MS (m/z) 645.00 $(M + 2H)^+$. |
| 86 | 4-(5-(3,5-dichlorophenyl)-5-(trifluoromethyl)-4,5-dihydroisoxazol-3-yl)-N-(1-ethyl-5-(3,3,3-trifluoropropyl)-1H-1,2,4-triazol-3-yl)-2-methylbenzamide | $^1$H-NMR (400 MHz, DMSO-$d_6$) δ 10.68 (s, 1H), 7.81 (t, J = 1.8 Hz, 1H), 7.66-7.59 (m, 4H), 7.51 (s, 1H), 4.40-4.27 (m, 2H), 4.10 (q, J = 6.8 Hz, 2H), 3.00 (t, J = 7.7 Hz, 2H), 2.78-2.72 (m, 2H), 2.41 (d, J = 15.2 Hz, 3H), 1.33-1.22 (m, 3H) ESI MS (m/z) 609.00 $(M + 2H)^+$. |
| 87 | 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-(3,3,3-trifluoropropyl)-1H-1,2,4-triazol-3-yl)-2-methylbenzamide | $^1$H-NMR (400 MHz, DMSO-$d_6$) δ 7.80 (t, J = 1.8 Hz, 1H), 7.62-7.60 (m, 2H), 7.50 (s, 1H), 7.43 (d, J = 7.8 Hz, 1H), 7.11 (d, J = 8.1 Hz, 1H), 6.36 (tt, J = 55.7, 4.1 Hz, 1H), 6.13-5.84 (m, 1H), 4.53 (td, J = 15.0, 3.3 Hz, 2H), 4.30 (td, J = 14.5, 3.9 Hz, 2H), 4.19 (d, J = 19.3 Hz, 2H), 2.87 (t, J = 7.6 Hz, 2H), 2.44-2.32 (m, 2H), 2.24 (s, 3H) ESI MS (m/z) 709.00 $(M + 2H)^+$. |
| 88 | 4-(5-(3,5-dichlorophenyl)-5-(trifluoromethyl)-4,5-dihydroisoxazol-3-yl)-2-methyl-N-(1-(prop-2-yn-1-yl)-5-(3,3,3-trifluoropropyl)-1H-1,2,4-triazol-3-yl)benzamide | $^1$H-NMR (400 MHz, DMSO-$d_6$) δ 10.81 (s, 1H), 7.81 (t, J = 2.0 Hz, 1H), 7.63-7.60 (m, 4H), 7.52 (d, J = 7.3 Hz, 1H), 5.10 (s, 2H), 4.39 (d, J = 18.3 Hz, 1H), 4.30 (d, J = 18.1 Hz, 1H), 3.55 (t, J = 2.4 Hz, 1H), 3.08-3.04 (m, 2H), 2.75 (d, J = 9.8 Hz, 2H), 2.39 (s, 3H) ESI MS (m/z) 618.00 $(M + H)^+$. |
| 89 | 4-(5-(3,5-dichlorophenyl)-5-(trifluoromethyl)-4,5-dihydroisoxazol-3-yl)-2-methyl-N-(prop-2-yn-1-yl)-N-(1-(prop-2-yn-1-yl)-5-(3,3,3-trifluoropropyl)-1H-1,2,4-triazol-3-yl)benzamide | $^1$H-NMR (400 MHz, DMSO-$d_6$) δ 7.80 (t, J = 1.8 Hz, 1H), 7.62-7.60 (m, 2H), 7.49 (s, 1H), 7.43 (d, J = 8.1 Hz, 1H), 7.13 (d, J = 7.8 Hz, 1H), 4.94 (d, J = 2.4 Hz, 2H), 4.62 (d, J = 2.2 Hz, 2H), 4.23 (dd, J = 25.4, 18.3 Hz, 2H), 3.37 (t, J = 2.4 Hz, 1H), 3.21 (t, J = 2.4 Hz, 1H), 2.88 (t, J = 7.6 Hz, 2H), 2.41-2.30 (m, 2H), 2.24 (s, 3H) ESI MS (m/z) 656.00 $(M + H)^+$. |
| 91 | 4-(5-(3,5-dichlorophenyl)-5-(trifluoromethyl)-4,5-dihydroisoxazol-3-yl)-N-(5-isopropyl-1-(prop-2-yn-1-yl)-1H-1,2,4-triazol-3-yl)-2-methylbenzamide | $^1$H-NMR (400 MHz, DMSO-$d_6$) δ 10.78 (s, 1H), 7.82-7.79 (m, 1H), 7.62-7.59 (m, 4H), 7.53 (t, J = 7.5 Hz, 1H), 5.06 (s, 2H), 4.41-4.28 (m, 3H), 3.51 (s, 1H), 3.25 (q, J = 6.7 Hz, 1H), 2.99 (s, OH), 2.40 (s, 3H), 1.24-1.20 (m, 6H) ESI MS (m/z) 562.00 $(M - H)^-$. |
| 92 | 4-(5-(3,5-dichlorophenyl)-5-(trifluoromethyl)-4,5-dihydroisoxazol-3-yl)-N-(5-isopropyl-1-(prop-2-yn-1-yl)-1H-1,2,4-triazol-3-yl)-2-methyl-N-(prop-2-yn-1-yl)benzamide | 1H-NMR (400 MHz, CHLOROFORM-D) δ 7.48 (d, J = 1.5 Hz, 2H), 7.42 (t, J = 1.8 Hz, 1H), 7.38 (s, 1H), 7.30 (d, J = 7.8 Hz, 1H), 7.19 (d, J = 8.1 Hz, 1H), 4.75 (d, J = 2.4 Hz, 2H), 4.65 (d, J = 2.4 Hz, 2H), 4.01 (d, J = 17.4 Hz, 1H), 3.64 (d, J = 17.4 Hz, 1H), 2.98-2.91 (m, 1H), 2.38 (s, 3H), 2.26 (dt, J = 9.3, 2.4 Hz, 2H), 1.17 (dd, J = 6.8, 1.2 Hz, 6H) ESI MS (m/z) 602.00 $(M + H)^+$. |
| 93 | N-(1-allyl-5-(3,3,3-trifluoropropyl)-1H-1,2,4-triazol-3-yl)-4-(5-(3,5-dichlorophenyl)-5-(trifluoromethyl)-4,5-dihydroisoxazol-3-yl)-2-methylbenzamide | 1H-NMR (400 MHz, CHLOROFORM-D) δ 7.60-7.51 (m, 5H), 7.44-7.43 (m, 1H), 5.95 (dq, J = 22.3, 5.3 Hz, 1H), 5.32 (d, J = 10.3 Hz, 1H), 5.17 (d, J = 17.1 Hz, 1H), 4.74 (d, J = 5.1 Hz, 2H), 4.10 (dd, J = 17.2, 9.4 Hz, 1H), 3.76-3.68 (m, 1H), 2.92-2.83 (m, 2H), 2.64-2.49 (m, 5H) ESI MS (m/z) 620.00 $(M + H)^+$. |
| 94 | 4-(5-(3,5-dichlorophenyl)-5-(trifluoromethyl)-4,5-dihydroisoxazol-3-yl)-N-(5-(methoxymethyl)-1-methyl-1H-1,2,4-triazol-3-yl)-2-methylbenzamide | 1H-NMR (400 MHz, CHLOROFORM-D) δ 8.71 (s, 1H), 7.61-7.54 (m, 3H), 7.51 (d, J = 1.5 Hz, 2H), 7.43 (t, J = 1.8 Hz, 1H), 4.52 (s, 2H), 4.09 (d, J = 17.1 Hz, 1H), 3.93 (s, 3H), 3.71 (d, J = 17.4 Hz, 1H), 3.43 (d, J = 28.1 Hz, 3H), 2.57 (s, 3H) ESI MS (m/z) 543.00 $(M + 2H)^+$. |
| 95 | 4-(5-(3,5-dichlorophenyl)-5-(trifluoromethyl)-4,5-dihydroisoxazol-3-y1)-N-(5-(methoxymethyl)-1-methyl-1H-1,2,4-triazol-3-yl)-N,2-dimethylbenzamide | 1H-NMR (400 MHz, CHLOROFORM-D) δ 7.49 (d, J = 1.5 Hz, 2H), 7.42 (t, J = 1.8 Hz, 1H), 7.40 (s, 1H), 7.32 (d, J = 7.8 Hz, 1H), 7.19 (d, J = 7.8 Hz, 1H), 4.41 (s, 2H), 4.03 (d, J = 17.4 Hz, 1H), 3.68-3.62 (m, 4H), 3.48 (d, J = 18.6 Hz, 3H), 3.22 (s, 3H), 2.38 (s, 3H) ESI MS (m/z) 557.00 $(M + 2H)^+$. |
| 96 | 4-(5-(3,5-dichlorophenyl)-5-(trifluoromethyl)-4,5-dihydroisoxazol-3-yl)-N-(5-(methoxymethyl)-1-(2,2,2-trifluoroethyl)-1H-1,2,4-triazol-3-yl)-2-methylbenzamide | 1H-NMR (400 MHz, CHLOROFORM-D) δ 8.31 (s, 1H), 7.58-7.53 (m, 3H), 7.51 (d, J = 1.5 Hz, 2H), 7.43 (t, J = 1.8 Hz, 1H), 4.91 (q, J = 8.2 Hz, 2H), 4.60 (s, 2H), 4.09 (d, J = 17.1 Hz, 1H), 3.70 (d, J = 17.4 Hz, 1H), 3.41 (s, 3H), 2.56 (s, 3H) ESI MS (m/z) 610.00 $(M + H)^+$. |

TABLE 1-continued

| Comp. No. | Compound Name | Analytical data |
|---|---|---|
| 97 | 4-(5-(3,5-dichlorophenyl)-5-(trifluoromethyl)-4,5-dihydroisoxazol-3-yl)-N-(1-ethyl-5-(methoxymethyl)-1H-1,2,4-triazol-3-yl)-2-methylbenzamide | 1H-NMR (400 MHz, CHLOROFORM-D) δ 8.42 (s, 1H), 7.61-7.51 (m, 6H), 7.45-7.43 (m, 1H), 4.48 (s, 2H), 4.24-4.14 (m, 2H), 4.10 (q, J = 8.6 Hz, 1H), 3.70 (d, J = 17.1 Hz, 1H), 3.37 (s, 3H), 2.56 (s, 3H), 1.46 (t, J = 7.2 Hz, 3H) ESI MS (m/z) 556.00 $(M + H)^+$. |
| 98 | 4-(5-(3,5-dichlorophenyl)-5-(trifluoromethyl)-4,5-dihydroisoxazol-3-yl)-N-(5-(methoxymethyl)-1-(2,2,2-trifluoroethyl)-1H-1,2,4-triazol-3-yl)-2-methyl-N-(2,2,2-trifluoroethyl)benzamide | 1H-NMR (400 MHz, CHLOROFORM-D) δ 7.49 (d, J = 1.7 Hz, 2H), 7.43-7.41 (m, 2H), 7.31-7.29 (m, 1H), 7.08 (d, J = 8.1 Hz, 1H), 4.65 (dt, J = 24.3, 8.3 Hz, 4H), 4.49 (s, 2H), 4.00 (d, J = 17.1 Hz, 1H), 3.63 (d, J = 17.1 Hz, 1H), 3.27 (s, 3H), 2.39 (s, 3H) ESI MS (m/z) 692.00 $(M + H)^+$. |
| 99 | 4-(5-(3,5-dichlorophenyl)-5-(trifluoromethyl)-4,5-dihydroisoxazol-3-yl)-N-ethyl-N-(1-ethyl-5-(methoxymethyl)-1H-1,2,4-triazol-3-yl)-2-methylbenzamide | 1H-NMR (400 MHz, CHLOROFORM-D) δ 7.48 (d, J = 1.5 Hz, 2H), 7.42 (t, J = 1.8 Hz, 1H), 7.37 (s, 1H), 7.29 (d, J = 8.1 Hz, 1H), 7.17 (d, J = 7.8 Hz, 1H), 4.40 (s, 2H), 4.02-3.93 (m, 5H), 3.62 (d, J = 17.1 Hz, 1H), 3.18 (s, 3H), 2.39 (s, 3H), 1.28 (q, J = 6.9 Hz, 3H), 1.13 (t, J = 7.1 Hz, 3H) ESI MS (m/z) 585.00 $(M + 2H)^+$. |
| 100 | 4-(5-(3,5-dichlorophenyl)-5-(trifluoromethyl)-4,5-dihydroisoxazol-3-yl)-N-(1-(2,2-difluoroethyl)-5-(methoxymethyl)-1H-1,2,4-triazol-3-yl)-2-methylbenzamide | $^1$H-NMR (400 MHz, DMSO-$d_6$) δ 10.88 (s, 1H), 7.81 (t, J = 1.8 Hz, 1H), 7.64-7.61 (m, 4H), 7.53 (d, J = 7.8 Hz, 1H), 6.37 (s, 1H), 4.69 (td, J = 14.7, 3.5 Hz, 2H), 4.58 (s, 2H), 4.35 (dd, J = 34.5, 18.3 Hz, 2H), 3.31 (s, 3H), 2.40 (s, 3H) ESI MS (m/z) 590.00 $(M - H)^-$. |
| 101 | 4-(5-(3,5-dichlorophenyl)-5-(trifluoromethyl)-4,5-dihydroisoxazol-3-yl)-N-(5-(methoxymethyl)-1-(prop-2-yn-1-yl)-1H-1,2,4-triazol-3-yl)-2-methylbenzamide | $^1$H-NMR (400 MHz, DMSO-$d_6$) δ 10.83 (s, 1H), 7.81 (t, J = 1.8 Hz, 1H), 7.62 (dd, J = 6.6, 4.9 Hz, 4H), 7.53 (d, J = 7.6 Hz, 1H), 5.07 (d, J = 2.2 Hz, 2H), 4.58 (s, 2H), 4.35 (dd, J = 34.7, 18.3 Hz, 2H), 3.50 (t, J = 2.4 Hz, 1H), 3.23 (s, 3H), 2.40 (s, 3H) ESI MS (m/z) 564.00 $(M - H)^-$. |
| 102 | 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-(methoxymethyl)-1H-1,2,4-triazol-3-yl)-2-methylbenzamide | $^1$H-NMR (400 MHz, DMSO-$d_6$) δ 7.80 (t, J = 2.0 Hz, 1H), 7.60 (d, J = 1.5 Hz, 2H), 7.50 (s, 1H), 7.42-7.40 (m, 1H), 7.12 (d, J = 7.9 Hz, 1H), 6.35 (tt, J = 55.5, 3.9 Hz, 1H), 5.92 (tt, J = 54.9, 3.6 Hz, 1H), 4.49 (td, J = 14.5, 3.7 Hz, 2H), 4.42 (s, 2H), 4.34-4.17 (m, 4H), 3.03 (s, 3H), 2.29 (d, J = 16.5 Hz, 3H) ESI MS (m/z) 656.00 $(M + H)^+$. |
| 103 | 4-(5-(3,5-dichlorophenyl)-5-(trifluoromethyl)-4,5-dihydroisoxazol-3-yl)-N-(5-(methoxymethyl)-1-(prop-2-yn-1-yl)-1H-1,2,4-triazol-3-yl)-2-methyl-N-(prop-2-yn-1-yl)benzamide | $^1$H-NMR (400 MHz, DMSO-$d_6$) δ 7.80 (t, J = 2.0 Hz, 1H), 7.59 (d, J = 1.7 Hz, 2H), 7.49 (s, 1H), 7.43-7.41 (m, 1H), 7.15 (d, J = 8.1 Hz, 1H), 4.89 (d, J = 2.4 Hz, 2H), 4.63 (d, J = 2.4 Hz, 2H), 4.43 (s, 2H), 4.25 (dd, J = 31.7, 18.5 Hz, 2H), 3.27 (t, J = 2.6 Hz, 1H), 3.21 (t, J = 2.4 Hz, 1H), 3.01 (d, J = 11.0 Hz, 3H), 2.26 (d, J = 10.8 Hz, 3H) ESI MS (m/z) 604.00 $(M + H)^+$. |
| 104 | N-(1-allyl-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide | $^1$H-NMR (400 MHz, DMSO-$d_6$) δ 10.75 (s, 1H), 7.81 (t, J = 1.8 Hz, 1H), 7.62-7.60 (m, 4H), 7.52 (d, J = 6.6 Hz, 1H), 5.96-5.91 (m, 1H), 5.22-5.12 (m, 2H), 4.77 (d, J = 5.1 Hz, 2H), 4.53 (s, 2H), 4.34 (dd, J = 34.4, 18.5 Hz, 2H), 3.28 (s, 3H), 2.40 (s, 3H) ESI MS (m/z) 568.00 $(M + H)^+$. |
| 105 | N-(1-(cyanomethyl)-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide | $^1$H-NMR (400 MHz, DMSO-$d_6$) δ 10.98 (s, 1H), 7.81 (t, J = 2.0 Hz, 1H), 7.64-7.61 (m, 4H), 7.54 (d, J = 8.1 Hz, 1H), 5.53 (s, 2H), 4.62 (s, 2H), 4.39 (d, J = 18.3 Hz, 1H), 4.30 (d, J = 18.3 Hz, 1H), 3.31 (s, 3H), 2.40 (s, 3H) ESI MS (m/z) 567.00 $(M + H)^+$. |
| 106 | N-(cyanomethyl)-N-(1-(cyanomethyl)-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide | $^1$H-NMR (400 MHz, DMSO-$d_6$) δ 7.80 (t, J = 1.8 Hz, 1H), 7.59 (d, J = 1.7 Hz, 2H), 7.53 (s, 1H), 7.46 (d, J = 7.8 Hz, 1H), 7.20 (d, J = 8.1 Hz, 1H), 5.37 (s, 2H), 4.96 (s, 2H), 4.48 (s, 2H), 4.22 (dd, J = 29.0, 18.5 Hz, 2H), 3.07 (s, 3H), 2.27 (s, 3H) ESI MS (m/z) 606.00 $(M + H)^+$. |
| 107 | N-allyl-N-(1-allyl-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide | $^1$H-NMR (400 MHz, DMSO-$d_6$) δ 7.80 (t, J = 1.8 Hz, 1H), 7.60 (d, J = 1.5 Hz, 2H), 7.48 (s, 1H), 7.39 (d, J = 7.9 Hz, 1H), 7.11 (d, J = 7.9 Hz, 1H), 5.88 (dq, J = 22.5, 5.2 Hz, 1H), 5.57 (dq, J = 22.3, 5.2 Hz, 1H), 5.24 (dd, J = 17.1, 1.5 Hz, 1H), 5.13 (dd, J = 10.4, 1.5 Hz, 1H), 4.81 (d, J = 10.7 Hz, 1H), 4.56 (d, J = 4.9 Hz, 2H), 4.45 (d, J = 5.2 Hz, 2H), 4.39 (d, J = 23.5 Hz, 3H), 4.24 (dd, J = 25.1, 18.3 Hz, 2H), 3.00 (s, 3H), 2.29 (s, 3H) ESI MS (m/z) 608.00 $(M + H)^+$. |

TABLE 1-continued

| Comp. No. | Compound Name | Analytical data |
|---|---|---|
| 108 | 4-(5-(3,5-dichloro-4-fluorophenyl)-5-(trifluoromethyl)-4,5-dihydroisoxazol-3-yl)-2-methyl-N-(1-(2,2,2-trifluoroethyl)-5-(3,3,3-trifluoropropyl)-1H-1,2,4-triazol-3-yl)benzamide | $^1$H-NMR (400 MHz, DMSO-$d_6$) δ 10.93 (s, 1H), 7.80 (d, J = 6.1 Hz, 2H), 7.62-7.59 (m, 2H), 7.53 (d, J = 7.6 Hz, 1H), 5.26 (q, J = 8.8 Hz, 2H), 4.34 (dd, J = 25.3, 18.5 Hz, 2H), 3.07 (t, J = 7.7 Hz, 2H), 2.77-2.65 (m, 2H), 2.41 (d, J = 18.8 Hz, 3H) ESI MS (m/z) 681.00 $(M + 2H)^+$. |
| 109 | 4-(5-(3,5-dichloro-4-fluorophenyl)-5-(trifluoromethyl)-4,5-dihydroisoxazol-3-yl)-2-methyl-N-(1-methyl-5-(3,3,3-trifluoropropyl)-1H-1,2,4-triazol-3-yl)benzamide | $^1$H-NMR (400 MHz, DMSO-$d_6$) δ 10.68 (s, 1H), 7.80 (d, J = 6.1 Hz, 2H), 7.61-7.49 (m, 3H), 4.34 (dd, J = 26.2, 18.3 Hz, 2H), 3.72 (d, J = 31.8 Hz, 3H), 3.01-2.98 (m, 2H), 2.80-2.69 (m, 2H), 2.37 (d, J = 13.2 Hz, 3H) ESI MS (m/z) 610.00 $(M - H)^-$. |
| 110 | 4-(5-(3,5-dichloro-4-fluorophenyl)-5-(trifluoromethyl)-4,5-dihydroisoxazol-3-yl)-N,2-dimethyl-N-(1-methyl-5-(3,3,3-trifluoropropyl)-1H-1,2,4-triazol-3-yl)benzamide | $^1$H-NMR (400 MHz, DMSO-$d_6$) δ 7.78 (d, J = 6.1 Hz, 2H), 7.48 (s, 1H), 7.41 (d, J = 8.1 Hz, 1H), 7.12 (d, J = 8.1 Hz, 1H), 4.24 (t, J = 19.1 Hz, 2H), 3.58 (s, 3H), 3.32 (s, 3H), 2.80 (t, J = 7.6 Hz, 2H), 2.41-2.29 (m, 2H), 2.24 (s, 3H) ESI MS (m/z) 628.00 $(M + 2H)^+$. |
| 111 | 4-(5-(3,5-dichloro-4-fluorophenyl)-5-(trifluoromethyl)-4,5-dihydroisoxazol-3-yl)-2-methyl-N-(2,2,2-trifluoroethyl)-N-(1-(2,2,2-trifluoroethyl)-5-(3,3,3-trifluoropropyl)-1H-1,2,4-triazol-3-yl)benzamide | $^1$H-NMR (400 MHz, DMSO-$d_6$) δ 7.79 (d, J = 6.4 Hz, 2H), 7.50 (s, 1H), 7.39 (d, J = 7.8 Hz, 1H), 7.08 (d, J = 8.1 Hz, 1H), 5.09 (q, J = 8.7 Hz, 2H), 4.73 (q, J = 9.0 Hz, 2H), 4.19 (dd, J = 24.3, 18.5 Hz, 2H), 2.93 (t, J = 7.5 Hz, 2H), 2.46-2.39 (m, 2H), 2.32-2.26 (m, 3H) ESI MS (m/z) 762.00 $(M + H)^+$. |
| 112 | N-(1-(cyanomethyl)-5-(3,3,3-trifluoropropyl)-1H-1,2,4-triazol-3-yl)-4-(5-(3,5-dichlorophenyl)-5-(trifluoromethyl)-4,5-dihydroisoxazol-3-yl)-2-methylbenzamide | $^1$H-NMR (400 MHz, DMSO-$d_6$) δ 10.95 (s, 1H), 7.81 (t, J = 1.8 Hz, 1H), 7.63-7.60 (m, 4H), 7.53 (d, J = 8.1 Hz, 1H), 5.54 (s, 2H), 4.34 (dd, J = 34.5, 18.3 Hz, 2H), 3.08 (t, J = 7.7 Hz, 2H), 2.79-2.71 (m, 2H), 2.40 (s, 3H) ESI MS (m/z) 619.00 $(M + H)^+$. |
| 113 | N-(cyanomethyl)-N-(1-(cyanomethyl)-5-(3,3,3-trifluoropropyl)-1H-1,2,4-triazol-3-yl)-4-(5-(3,5-dichlorophenyl)-5-(trifluoromethyl)-4,5-dihydroisoxazol-3-yl)-2-methylbenzamide | $^1$H-NMR (400 MHz, DMSO-$d_6$) δ 7.80 (t, J = 2.0 Hz, 1H), 7.60 (d, J = 1.7 Hz, 2H), 7.53 (s, 1H), 7.47 (d, J = 8.1 Hz, 1H), 7.20 (d, J = 8.1 Hz, 1H), 5.39 (s, 2H), 4.95 (s, 2H), 4.21 (dd, J = 23.8, 18.5 Hz, 2H), 2.93 (t, J = 7.6 Hz, 2H), 2.44-2.34 (m, 2H), 2.25 (s, 3H) ESI MS (m/z) 656.00 $(M + H)^+$. |
| 114 | 4-(5-(3,5-dichloro-4-fluorophenyl)-5-(trifluoromethyl)-4,5-dihydroisoxazol-3-yl)-N-(1-(2,2-difluoroethyl)-5-(3,3,3-trifluoropropyl)-1H-1,2,4-triazol-3-yl)-2-methylbenzamide | $^1$H-NMR (400 MHz, DMSO-$d_6$) δ 10.84 (s, 1H), 7.80 (d, J = 6.1 Hz, 2H), 7.60 (d, J = 11.7 Hz, 2H), 7.52 (d, J = 7.6 Hz, 1H), 6.38 (t, J = 54.5 Hz, 1H), 4.73-4.66 (m, 2H), 4.34 (dd, J = 25.8, 18.5 Hz, 2H), 3.04 (t, J = 7.8 Hz, 2H), 2.72 (t, J = 9.5 Hz, 2H), 2.39 (s, 3H) ESI MS (m/z) 664.00 $(M + 2H)^+$. |
| 115 | 4-(5-(3,5-dichloro-4-fluorophenyl)-5-(trifluoromethyl)-4,5-dihydroisoxazol-3-yl)-2-methyl-N-(prop-2-yn-1-yl)-N-(1-(prop-2-yn-1-yl)-5-(3,3,3-trifluoropropyl)-1H-1,2,4-triazol-3-yl)benzamide | $^1$H-NMR (400 MHz, DMSO-$d_6$) δ 7.81-7.77 (m, 2H), 7.48 (s, 1H), 7.44-7.41 (m, 1H), 7.14 (d, J = 8.1 Hz, 1H), 4.95 (d, J = 2.4 Hz, 2H), 4.63 (d, J = 2.2 Hz, 2H), 4.23 (s, 2H), 3.37 (t, J = 2.6 Hz, 1H), 3.20 (t, J = 2.3 Hz, 1H), 2.88 (t, J = 7.6 Hz, 2H), 2.42-2.30 (m, 2H), 2.24 (s, 3H) ESI MS (m/z) 676.00 $(M + 2H)^+$. |

* Compound names generated using Chemdraw Professional 19.1

The compounds of the present invention include stereoisomers, particularly optical isomers. The few representative compounds were purified by chiral chromatography and analytical details were mentioned in the Table 2.

Method Conditions

Instrument: Shimadzu UHPLC Nexera X2

Column: Chiralpak IG, 250*4.6 mm

Oven temperature: 25° C.

Flow rate: 1.0 mL

Mobile phase: Ethanol:Hexane: 25:75

TABLE 2

| Compound Name | Ret. Time (Min) |
|---|---|
| (R)/(S)4-(5-(3,5-dichloro-4-fluorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)-N-(2,2,2-trifluoroethyl)benzamide | 4.328 and 4.738 |

TABLE 2-continued

| Compound Name | Ret. Time (Min) |
|---|---|
| (R)/(S)4-(5-(3,5-dichloro-4-fluorophenyl)-5-(trifluoromethyl)-4,5-dihydroisoxazol-3-yl)-N-(1-ethyl-5-(trifluoromethyl)-1H-1,2,4-triazol-3-yl)-2-methylbenzamide | 5.972 and 8.110 |
| (R)/(S)4-(5-(3,5-dichloro-4-fluorophenyl)-5-(trifluoromethyl)-4,5-dihydroisoxazol-3-yl)-N-ethyl-N-(1-ethyl-5-(trifluoromethyl)-1H-1,2,4-triazol-3-yl)-2-methylbenzamide | 4.301 and 4.717 |

* Compound names generated using Chemdraw Professional 19.1

As described herein, the compounds of formula (I) show insecticidal activities which are exerted with respect to numerous insects which attacks on important agricultural crops. The compounds of the present invention were assessed for their activity as described in the following tests:

BIOLOGY EXAMPLES

Example A: *Helicoverpa armigera*

The diet incorporation method was used, in which the required quantity of the test compound was weighed and dissolved in a tube containing solvent solution. The tube was put on a vortex at 2000 rpm for 90 min for proper mixing. Semi-synthetic diet was incorporated into this solution when the temperature was approximately 50° C. in the bioassay containers. Compound and diet were stirred thoroughly for proper mixing and allowed to cool for 30 min. The solidified diet was cut into equal pieces, and then each piece was transferred into one cell of a bio-assay tray. A single starved third instar larva was released into each of the cells of the bioassay trays and the tray was covered with the lid. The bio-assay trays were then kept under laboratory conditions at a temperature of 25° C. and a relative humidity of 70%. Observations on dead, moribund and alive larvae were recorded 96 h after the release of the larvae. Percent mortality was calculated by combining dead and moribund larvae and comparing the result to the one of the untreated control. The compounds, 1 2 3 4 5 6 7
8 10 11 12 13 14 15 16 18 19 20 21
22 23 24 25 26 27 28 29 32 34 37 38
39 40 41 42 44 45 46 47 48 49 50 51
52 53 55 56 57 58 61 62 63 64 65 66
67 68 69 70 71 74 79 80 84 85 86 88
90 91 92 97 99 101 104 105 108 109 112 and 113
recorded ≥70 per cent mortality @ 300 PPM.

Example B: *Spodoptera litura*

The diet incorporation method was used, in which the required quantity of the test compound was weighed and dissolved in a tube containing solvent solution. The tube was put on a vortex at 2000 rpm for 90 min for proper mixing. Semi-synthetic diet was incorporated into this solution when the temperature was approximately 50° C. in the bioassay containers. Compound and diet were stirred thoroughly for proper mixing and allowed to cool for 30 min. The solidified diet was cut into equal pieces, and then each piece was transferred into one cell of a bio-assay tray. A single starved third instar larva was released into each of the cells of the bioassay trays and the tray was covered with the lid. The bio-assay trays were then kept under laboratory conditions at a temperature of 25° C. and a relative humidity of 70%. Observations on dead, moribund and alive larvae were recorded 96 h after the release of larvae. Percent mortality was calculated by combining dead and moribund larvae and comparing the result to the one of the untreated control. The compounds 1 2 3 5 8 10
11 12 13 14 15 16 18 19 20 26 30 34
36 37 38 39 40 42 43 45 46 47 48 49
51 52 53 55 56 57 58 61 62 63 65 66
67 68 69 70 72 73 74 75 77 79 82 84
88 90 91 92 97 101 105 108 109 and 112 recorded ≥70
per cent mortality @ 300 PPM.

Example C: *Plutella xylostella*

The leaf dip method was used for testing, wherein the required quantity of the compound was weighed and dissolved in a tube containing solvent solution. The tube was put on a vortex at 2000 rpm for 90 min for proper mixing, then, diluted with a 0.01% Triton-X solution to the desired test concentration. Cabbage leaves were dipped in the compound solution for 10 seconds, shade dried for 20 min and then transferred into the cells of bioassay trays. A single second instar larva was released into each cell and the tray was covered with a lid. The bio-assay trays were then kept under laboratory conditions at a temperature of 25° C. and a relative humidity of 70%. Observations on dead, moribund and alive larvae were recorded 72 h after the release. Percent mortality was calculated by combining dead and moribund larvae and comparing the result to the one of the untreated control. The compounds, 1 2 3 4
5 6 7 8 9 10 11 12 13 14 15 16
17 18 19 20 21 22 23 24 25 26 27 28
29 30 31 32 33 34 35 36 37 38 39 40
41 42 43 44 45 46 47 48 49 50 51 52
53 54 55 56 57 58 59 60 61 62 63 64
65 66 67 68 69 70 71 72 73 74 75 76
77 78 79 80 81 82 83 84 85 86 87 88
89 90 91 92 93 94 95 96 97 98 99 100
101 102 103 104 105 106 107 108 109 110 111 112
113 114 and 115 recorded ≥70 per cent mortality @ 300 PPM.

Example D: *Bemisia tabaci*

The leaf dip method was used for testing, wherein the required quantity of the compound was weighed and dissolved in a tube containing solvent solution. The tube was put on a vortex at 2000 rpm for 90 min for proper mixing, then, diluted with a 0.01% Triton-X solution to the desired test concentration. Brinjal leaves were dipped in the compound solution for 10 seconds; shade dried for 20 min and then placed, with the abaxial side of the leaf up, on 4 ml of a solidified 1% agar-agar solution in respective perforated container caps. Known numbers of freshly emerged whitefly adults were collected, using a modified aspirator, and released into a perforated container in which the cap containing the treated leaf was placed. The containers were kept in a plant growth chamber at a temperature of 25° C. and relative humidity of 70%. Observations on dead, moribund and alive adults were recorded 72 h after the release. Percent mortality was calculated by combining dead and moribund adults and comparing the result to the one of the untreated control. The compound 1
2 3 6 7 8 10 11 12 16 18 19 20
21 23 26 27 28 29 32 34 38 40 41 46
47 48 49 50 56 57 61 62 63 64 67 68
69 70 74 75 77 79 80 84 86 88 91 92
93 94 95 97 101 103 104 and 105 recorded ≥70 per cent mortality @ 300 PPM.

Example E: *Myzus persicae*

The leaf dip method was used for testing, wherein the required quantity of the compound was weighed and dissolved in a tube containing solvent solution. The tube was put on a vortex at 2000 rpm for 90 min for proper mixing, then, diluted with 0.01% Triton-X solution to the desired test concentration. *Capsicum* leaves were dipped in the compound solution for 10 seconds, shade dried for 20 min and then placed, with the abaxial side of the leaf up, in single cells of a bio-assay tray containing 4 ml of a solidified 1% agar-agar solution. Known numbers of third instar nymphs, collected in petri plates, were released into the cell with the treated leaf and the cell was covered with a perforated lid for better aeration. The trays were kept in a plant growth chamber at a temperature of 25° C. and a relative humidity of 70%. Observations on dead, moribund and alive nymphs were recorded 72 h after the release. Percent mortality was calculated by combining dead and moribund nymphs and comparing the result with the one of the untreated control. The compounds, 1 2 3 4 5 6 7 8 10 11 12
16 19 21 26 28 29 32 33 38 40 41 46
47 48 53 61 62 63 64 67 68 69 70 71
74 75 79 80 84 86 88 91 94 99 and 101
recorded ≥70 per cent mortality @ 300 PPM.

Example F: *Nilaparvata lugens*

The seedling dip method was used for testing, wherein the required quantity of the compound was weighed and dissolved in a tube containing solvent solution. The tube was put on a vortex at 2000 rpm for 90 min for proper mixing, then, diluted with a 0.01% Triton-X solution to the desired test concentration. Paddy seedlings were dipped in the compound solution for 10 seconds, shade dried for 20 min and then the seedlings were placed in glass test tubes with the roots kept in water. 15 third instar nymphs were released into each test tube and the tubes were kept in a plant growth chamber at a temperature of 25° C. and relative humidity of 75%. Observations on dead, moribund and alive nymphs were recorded 72 h after the release. Percent mortality was calculated by combining dead and moribund nymphs and comparing the result to the one of the untreated control. The compounds, 1 2 5 6
10 11 21 67 68 69 71 74 75 79 80 84
91 92 93 and 103 recorded ≥70 per cent mortality @ 300 PPM.

Example G: *Tetranychus urticae*

The leaf dip method was used for testing, wherein the required quantity of the compound was weighed and dissolved in a tube containing solvent solution. The tube was put on a vortex at 2000 rpm for 90 min for proper mixing, then, diluted with 0.01% Triton-X solution to the desired test concentration. French bean leaves were dipped in the compound solution for 10 seconds, shade dried for 20 min and then placed, with the abaxial side of the leaf up, in single cells of a bio-assay tray containing 4 mL of a solidified 1% agar-agar solution. Known numbers of third instar nymphs were released into the cell with the treated leaf and the cell was covered with a perforated lid for better aeration. The trays were kept in a plant growth chamber at a temperature of 25° C. and a relative humidity of 70%. Observations on dead, moribund and alive nymphs were recorded 72 h after the release. Percent mortality was calculated by combining dead and moribund nymphs and comparing the result with the one of the untreated control. The compounds 1 2 26 38 40 46 47 48 and 49 recorded ≥70 percent mortality @ 300 PPM.

Example H: *Amrasca biguttulla biguttulla*

The leaf dip method was used for testing, wherein the required quantity of the compound was weighed and dissolved in a tube containing solvent solution. The tube was put on a vortex at 2000 rpm for 90 min for proper mixing, then, diluted with 0.01% Triton-X solution to the desired test concentration. Brinjal leaves were dipped in the compound solution for 10 seconds, shade dried for 20 min and then placed, with the abaxial side of the leaf up, in single cells of a bio-assay tray containing 4 mL of a solidified 1% agar-agar solution. Known numbers of second instar nymphs were released into the cell with the treated leaf and the cell was covered with a perforated lid for better aeration. The trays were kept in a plant growth chamber at a temperature of 25° C. and a relative humidity of 70%. Observations on dead, moribund and alive nymphs were recorded 72 h after the release. Percent mortality was calculated by combining dead and moribund nymphs and comparing the result with the one of the untreated control. The compounds 1, 2 and 40 recorded ≥70 percent mortality @ 300 PPM.

Example I: *Scirtothrips dorsalis*

The leaf dip method was used for testing, wherein the required quantity of the compound was weighed and dissolved in a tube containing solvent solution. The tube was put on a vortex at 2000 rpm for 90 min for proper mixing, then, diluted with 0.01% Triton-X solution to the desired test concentration. *Capsicum* leaves were dipped in the compound solution for 10 seconds, shade dried for 20 min and then placed, with the abaxial side of the leaf up, in single cells of a bio-assay tray containing 4 mL of a solidified 1% agar-agar solution. Known numbers of second instar nymphs were released into the cell with the treated leaf and the cell was covered with a perforated lid for better aeration. The trays were kept in a plant growth chamber at a temperature of 25° C. and a relative humidity of 70%. Observations on dead, moribund and alive nymphs were recorded 72 h after the release. Percent mortality was calculated by combining dead and moribund nymphs and comparing the result with the one of the untreated control. The compounds 1, 2 and 40 recorded ≥70 percent mortality @ 300 PPM.

Having described the invention with reference to certain preferred embodiments, other embodiments will become apparent to one skilled in the art from consideration of the specification. It will be apparent to those skilled in the art that many modifications, both to materials and methods, may be practiced without departing from the scope of the invention.

The invention claimed is:

1. A compound of formula (I),

Formula (I)

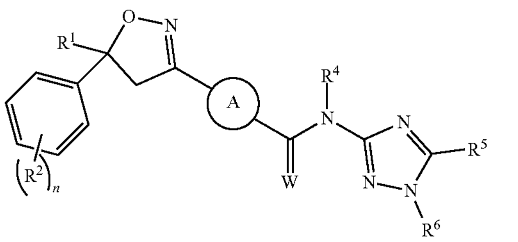

wherein, $R^1$ is selected from the group consisting of $C_1$-$C_6$-alkyl, $C_1$-$C_6$-haloalkyl, $C_3$-$C_6$-cycloalkyl and $C_3$-$C_6$-halocycloalkyl;

wherein $R^2$ is selected from the group consisting of hydrogen, halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl and $C_3$-$C_8$-cycloalkyl;

ring A is selected from the group consisting of $C_6$-$C_{10}$-aryl and $C_5$-$C_{10}$-heterocyclyl group, which may optionally be substituted with one or more groups of $R^3$;

$R^3$ is selected from the group consisting of hydrogen, halogen, cyano, nitro, $C_1$-$C_4$-alkyl, $C_2$-$C_4$-alkenyl, $C_2$-$C_6$-alkynyl, $C_1$-$C_4$-haloalkyl, $C_2$-$C_4$-haloalkenyl, $C_2$-$C_6$-haloalkynyl, $C_3$-$C_4$-cycloalkyl, $C_3$-$C_5$-heterocyclyl, —$OC_3$-$C_4$-heterocyclyl, SCN, $SF_5$, NR'R", OR', $S(O)_m$R', and CR'═NR"; or two $R^3$ together with the atom to which they are attached or together with the further atoms selected from the group consisting of C, N, O, S and optionally including 1 to 3 ring members selected from the group consisting of C(═O), C(═S), $S(O)_m$ and $Si(R')_2$ may form a five to six membered ring, which for its part may be substituted by one or more groups selected from the group consisting of X, CN, R', OR', SR', $N(R')_2$, $Si(R')_3$, COOR', and $CON(R')_2$;

W represents O or S;

$R^4$ is selected from the group consisting of hydrogen, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_3$-$C_8$-cycloalkyl, $C_3$-$C_8$-cycloalkyl-$C_1$-$C_8$-alkyl, $OR^{4a}$, —$C_1$-$C_6$-alkyl-$OR^{4a}$, —OC(═O)—R", —$C_1$-$C_6$-alkyl-C(═O)$C_3$-$C_6$-cycloalkyl, —$C_1$-$C_6$-alkyl-OC(═O)—R", —$C_1$-$C_6$-alkyl-N(R')C(═O)OR', —C(═O)—R" and $Si(R')_3$;

$R^{4a}$ is selected from the group consisting of hydrogen, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_3$-$C_8$-cycloalkyl, $C_3$-$C_8$-cycloalkyl-$C_1$-$C_8$-alkyl, —$C_1$-$C_6$-alkyl-$OR^{4b}$, $C_1$-$C_6$-alkyl-C(═O)$C_3$-$C_6$-cycloalkyl, —$C_1$-$C_6$-alkyl-OC(═O)—R", —$C_1$-$C_6$-alkyl-N(R')C(═O)OR', —C(═O)—R" and $Si(R')_3$;

$R^{4b}$ is selected from the group consisting of hydrogen, $C_1$-$C_8$-alkyl, $C_3$-$C_8$-cycloalkyl, $C_3$-$C_8$-cycloalkyl-$C_1$-$C_8$-alkyl, and C(═O)—R";

$R^5$ is selected from the group consisting of halogen, cyano, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, cyano-$C_1$-$C_8$-alkyl, $OR^{4a}$, $C_1$-$C_6$-alkyl-$OR^{4a}$, $C_3$-$C_8$-cycloalkyl, $C_3$-$C_8$-cycloalkyl-$C_1$-$C_8$-alkyl, $C_3$-$C_8$-halocycloalkyl, cyano-$C_3$-$C_8$-cycloalkyl, $Si(R')_3$, C(═O)—R", $S(O)_m$R', $C_1$-$C_6$-alkyl-$S(O)_m$R" and phenyl;

$R^6$ is selected from the group consisting of $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, $OR^{4a}$, $C_1$-$C_6$-alkyl-$OR^{4a}$, $C_3$-$C_8$-cycloalkyl, $C_3$-$C_8$-cycloalkyl-$C_1$-$C_8$-alkyl, $Si(R')_3$, C(═O)—R", $S(O)_m$R', and phenyl;

each group of $R^2$, $R^3$, $R^4$, $R^5$ and $R^6$ may optionally be substituted by one or more groups selected from the group consisting of halogen, CN, R", OR", SR", NR'R", $Si(R')_3$, C(═O)OR', and C(═O)NR'R";

R' is selected from the group consisting of hydrogen, $C_1$-$C_6$-alkyl, $C_2$-$C_6$-alkenyl or $C_3$-$C_8$-cycloalkyl; wherein alkyl, alkenyl and cycloalkyl groups may optionally be substituted by one or more halogen or cyano;

R" is selected from the group consisting of hydrogen, $C_1$-$C_6$-alkyl, $C_2$-$C_6$-alkenyl, $C_1$-$C_6$-haloalkyl, $C_3$-$C_8$-cycloalkyl, $N(R')_2$, OR', C(═O)R', C(═O)OR', phenyl and $C_3$-$C_6$-heterocyclyl; each group of R" may optionally be substituted by one or more groups selected from the group consisting of halogen, R', CN, OR', SR', $N(R')_2$, $Si(R')_3$, C(═O)OR' and C(═O)$N(R')_2$;

n represents integers of 0-4; and m represents integers of 0-2;

and salts, stereo-isomers, metal complexes, polymorphs, or N-oxides thereof.

2. A compound of formula (I) according to claim 1, wherein the said compound of formula (I) is represented by a compound of formula (Ia);

Formula (Ia)

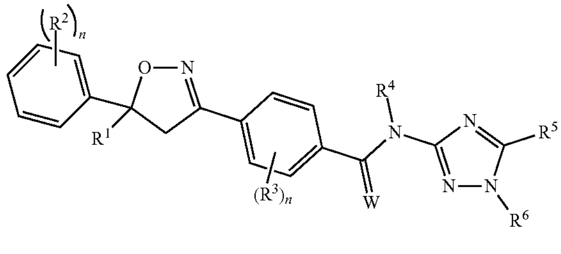

wherein, $R^1$ is selected from the group consisting of $C_1$-$C_6$-alkyl, $C_1$-$C_6$-haloalkyl, $C_3$-$C_6$-cycloalkyl and $C_3$-$C_6$-halocycloalkyl;

wherein $R^2$ is selected from the group consisting of hydrogen, halogen, cyano, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl and $C_3$-$C_8$-cycloalkyl;

$R^3$ is selected from the group consisting of hydrogen, halogen, cyano, nitro, $C_1$-$C_4$-alkyl, $C_2$-$C_4$-alkenyl, $C_2$-$C_6$-alkynyl, $C_1$-$C_4$-haloalkyl, $C_2$-$C_4$-haloalkenyl, $C_2$-$C_6$-haloalkynyl, $C_3$-$C_4$-cycloalkyl, $C_3$-$C_5$-heterocyclyl, —$OC_3$-$C_4$-heterocyclyl, SCN, $SF_5$, NR'R", OR', $S(O)_m$R', and CR'═NR";

two $R^3$ together with the atom to which they are attached or together with the further atoms selected from the group consisting of C, N, O, S and optionally including 1 to 3 ring members selected from the group consisting of C(═O), C(═S), $S(O)_m$ and $Si(R')_2$ may form a five to six membered ring, which for its part may be substituted by one or more groups selected from the group consisting of X, CN, R', OR', SR', $N(R')_2$, $Si(R')_3$, COOR', and $CON(R')_2$;

W represents O or S;

$R^4$ is selected from the group consisting of hydrogen, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_3$-$C_8$-cycloalkyl, $C_3$-$C_8$-cycloalkyl-$C_1$-$C_8$-alkyl, $OR^{4a}$, —$C_1$-$C_6$-alkyl-$OR^{4a}$, —OC(═O)—R", —$C_1$-$C_6$-alkyl-C(═O)$C_3$-$C_6$-cycloalkyl, —$C_1$-$C_6$-alkyl-OC(═O)—R", —$C_1$-$C_6$-alkyl-N(R')C(═O)OR', —C(═O)—R" and $Si(R')_3$;

$R^{4a}$ is selected from the group consisting of hydrogen, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_3$-$C_8$-cycloalkyl, $C_3$-$C_8$-cycloalkyl-$C_1$-$C_8$-alkyl, —$C_1$-$C_6$-alkyl-$OR^{4b}$, $C_1$-$C_6$-alkyl-C(═O)$C_3$-$C_6$-cycloalkyl, —$C_1$-$C_6$-alkyl-OC(═O)—R", —$C_1$-$C_6$-alkyl-N(R')C(═O)OR', —C(═O)—R" and $Si(R')_3$;

$R^{4b}$ is selected from the group consisting of hydrogen, $C_1$-$C_8$-alkyl, $C_3$-$C_8$-cycloalkyl, $C_3$-$C_8$-cycloalkyl-$C_1$-$C_8$-alkyl, and C(═O)—R";

$R^5$ is selected from the group consisting of halogen, cyano, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, cyano-$C_1$-$C_8$-alkyl, $OR^{4a}$, $C_1$-$C_6$-alkyl-$OR^{4a}$, $C_3$-$C_8$-cycloalkyl, $C_3$-$C_8$-cycloalkyl-$C_1$-$C_8$-alkyl, $C_3$-$C_8$-halocycloalkyl, cyano-$C_3$-$C_8$-cycloalkyl, $Si(R')_3$, C(═O)—R", $S(O)_m$R', $C_1$-$C_6$-alkyl-$S(O)_m$R" and phenyl;

$R^6$ is selected from the group consisting of $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, $OR^{4a}$, $C_1$-$C_6$-alkyl-$OR^{4a}$, $C_3$-$C_8$-cycloalkyl, $C_3$-$C_8$-cycloalkyl-$C_1$-$C_8$-alkyl, $Si(R')_3$, C(═O)—R", $S(O)_m$R', and phenyl;

each group of $R^2$, $R^3$, $R^4$, $R^5$ and $R^6$ may optionally be substituted by one or more groups selected from the group consisting of halogen, CN, R", OR", SR", NR'R", $Si(R')_3$, C(═O)OR', and C(═O)NR'R";

R' is selected from the group consisting of hydrogen, $C_1$-$C_6$-alkyl, $C_2$-$C_6$-alkenyl or $C_3$-$C_8$-cycloalkyl; wherein alkyl, alkenyl and cycloalkyl groups may optionally be substituted by one or more halogen or cyano;

R" is selected from the group consisting of hydrogen, $C_1$-$C_6$-alkyl, $C_2$-$C_6$-alkenyl, $C_1$-$C_8$-haloalkyl, $C_3$-$C_8$-cycloalkyl, $N(R')_2$, OR', C(═O)R', C(═O)OR', phenyl and $C_3$-$C_6$-heterocyclyl; each group of R" may optionally be substituted by one or more groups selected from the group consisting of halogen, R', CN, OR', SR', $N(R')_2$, $Si(R')_3$, C(═O)OR' and C(═O)$N(R')_2$;

n represents integers of 0-4; and m represents integers of 0-2;

and salts, stereo-isomers, metal complexes, polymorphs, or N-oxides thereof.

3. A compound of formula (I) according to claim 1, wherein the said compound of formula (I) is represented by a compound of formula (Ia-1);

Formula (Ia-1)

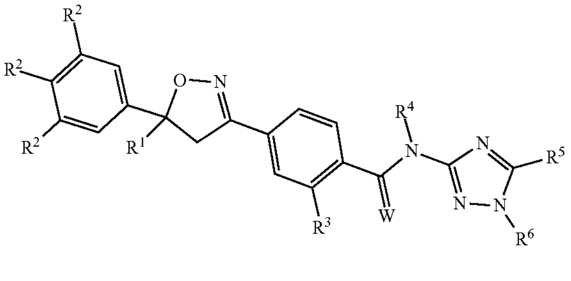

wherein $R^2$ is independently selected from hydrogen or halogen;

W is O;

$R^3$ is selected from the group consisting of hydrogen, halogen, cyano, OR', $C_1$-$C_4$-alkyl, $C_3$-$C_4$-cycloalkyl;

$R^4$, $R^5$, $R^6$, are as defined in claim 1; or salts, stereo-isomers, metal complexes, polymorphs, or N-oxides thereof.

4. A compound of formula (I) according to claim 1, wherein the said compound of formula (I) is selected from 4-(5-(3,5-dichloro-4-fluorophenyl)-5-(trifluoromethyl)-4,5-dihydroisoxazol-3-yl)-2-methyl-N-(1-methyl-5-(trifluoromethyl)-1H-1,2,4-triazol-3-yl)benzamide; 4-(5-(3,5-dichlorophenyl)-5-(trifluoromethyl)-4,5-dihydroisoxazol-3-yl)-2-methyl-N-(1-methyl-5-(trifluoromethyl)-1H-1,2,4-triazol-3-yl)benzamide; 4-(5-(3,5-dichloro-4-fluorophenyl)-5-(trifluoromethyl)-4,5-dihydroisoxazol-3-yl)-N-(5-ethyl-1-methyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-ethyl-1-methyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(5-ethyl-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-ethyl-1-methyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(1,5-diethyl-1H-1,2,4-triazol-3-yl)-N-ethyl-2-methylbenzamide; 4-(5-(3,5-dichlorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)benzamide; 4-(5-(3,5-dichloro-4-fluorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)-N-(2,2,2-trifluoroethyl)benzamide; 4-(5-(3,5-dichloro-4-fluorophenyl)-5-(trifluoromethyl)-4,5-dihydroisoxazol-3-yl)-2-methyl-N-(1-methyl-5-(methylthio)-1H-1,2,4-triazol-3-yl)benzamide; 4-(5-(3,5-dichloro-4-fluorophenyl)-5-(trifluoromethyl)-4,5-dihydroisoxazol-3-yl)-N,2-dimethyl-N-(1-methyl-5-(methylthio)-1H-1,2,4-triazol-3-yl)benzamide; 4-(5-(3,5-dichloro-4-fluorophenyl)-5-(trifluoromethyl)-4,5-dihydroisoxazol-3-yl)-N-(1,5-dimethyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(1,5-dimethyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(1,5-dimethyl-1H-1,2,4-triazol-3-yl)-2-methylbenzamide; 4-(5-(3,5-dichlorophenyl)-5-(trifluoromethyl)-4,5- dihydroisoxazol-3-yl)-N-(1,5-dimethyl-1H-1,2,4-triazol-3-yl)-N,2-dimethylbenzamide; 4-(5-(3,5-dichloro-4-fluorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)benzamide; 4-(5-(3,5-dichloro-4-fluorophenyl)-5-(trifluoromethyl)-4,5-dihydroisoxazol-3-yl)-2-methyl-N-(5-methyl-1-(2,2,2-trifluoroethyl)-1H-1,2,4-triazol-3-yl)-N-(2,2,2-trifluoroethyl)benzamide; N-(1-allyl-5-methyl-1H-1,2,4-triazol-3-yl)-4-(5-(3,5-dichloro-4-fluorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-2-methyl-N-(5-methyl-1-(prop-2-yn-1-yl)-1H-1,2,4-triazol-3-yl)benzamide; 4-(5-(3,5-dichloro-4-fluorophenyl)-5-(trifluoromethyl)-4,5-dihydroisoxazol-3-yl)-2-methyl-N-(1-(2,2,2-trifluoroethyl)-5-(trifluoromethyl)-1H-1,2,4-triazol-3-yl)benzamide; 4-(5-(3,5-dichloro-4-fluorophenyl)-5-(trifluoromethyl)-4,5-dihydroisoxazol-3-yl)-N-(1-ethyl-5-methyl-1H-1,2,4-triazol-3-yl)-2-methylbenzamide; N-(cyclopropylmethyl)-N-(1-(cyclopropylmethyl)-5-methyl-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichlorophenyl)-5-(trifluoromethyl)-4,5-dihydroisoxazol-3-yl)-N-ethyl-N-(1-ethyl-5-methyl-1H-1,2,4-triazol-3-yl)-2-methylbenzamide; N-allyl-N-(1-allyl-5-methyl-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-N-(5-isopropyl-1-methyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-isopropyl-1-methyl-1H-1,2,4-triazol-3-yl)-N,2-dimethylbenzamide; 4-(5-(3,5-dichloro-4-fluorophenyl)-5-(trifluoromethyl)-4,5-dihydroisoxazol-3-yl)-N-(1-ethyl-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-ethyl-5-methyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methyl-N-(2,2,2-trifluoroethyl)benzamide; N-(1-allyl-5-(trifluoromethyl)-1H-1,2,4-triazol-3-yl)-4-(5-(3,5-dichloro-4-fluorophenyl)-5-(trifluoromethyl)-4,5-dihydroisoxazol-3-yl)-2-methylbenzamide; N-(1-allyl-5-(trifluoromethyl)-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-N-(1-(2,2-difluoroethyl)-5-(trifluoromethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(2,2-difluoroethyl)-N-(1-(2,2-difluoroethyl)-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-(2,2-difluoroethyl)-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1,5-diethyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N,2-dimethyl-N-(1-methyl-5-(trifluoromethyl)-1H-1,2,4-triazol-3-yl)benzamide; N-(1-(cyanomethyl)-5-(trifluoromethyl)-1H-1,2,4-triazol-3-yl)-4-(5-(3,5-dichloro-4-fluorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-2-methyl-N-(1-methyl-5-phenyl-1H-1,2,4-triazol-3-yl)benzamide; 4-(5-(3,5-dichloro-4-fluorophenyl)-5-(trifluoromethyl)-4,5-dihydroisoxazol-3-yl)-N,2-dimethyl-N-(1-methyl-5-phenyl-1H-1,2,4-triazol-3-yl)benzamide; 4-(5-(3,5-dichloro-4-fluorophenyl)-5-(trifluoromethyl)-4,5-dihydroisoxazol-3-yl)-N-ethyl-N-(1-ethyl-5-(trifluoromethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-2-methyl-N-(1-(prop-2-yn-1-yl)-5-(trifluoromethyl)-1H-1,2,4-triazol-3-yl)benzamide; 4-(5-(3,5-dichloro-4-fluorophenyl)-5-(trifluoromethyl)-4,5-dihydroisoxazol-3-yl)-N-(5-(1,1-difluoroethyl)-1-methyl-1H-1,2,4-triazol-3-yl)-N,2-dimethylbenzamide; 4-(5-(3,5-dichloro-4-fluorophenyl)-5-(trifluoromethyl)-4,5-dihydroisoxazol-3-yl)-N-(5-(1,1-difluoroethyl)-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-methyl-1H-1,2,4-triazol-3-yl)-N,2-dimethylbenzamide; N-(1-(cyanomethyl)-5-(trifluoromethyl)-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichlorophenyl)-5-(trifluoromethyl)-4,5-dihydroisoxazol-3-yl)-2-methyl-N-(1-(2,2,2-trifluoroethyl)-5-(trifluoromethyl)-1H-1,2,4-triazol-3-yl)benzamide; 4-(5-(3,5-dichlorophenyl)-5-(trifluoromethyl)-4,5-dihydroisoxazol-3-yl)-N-(1-(2-methoxyethyl)-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-ethyl-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-(trifluoromethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-(2,2,2-trifluoroethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-(1,1-difluoroethyl)-1-(2,2-difluoroethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-(2,2-difluoroethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-(1,1-difluoroethyl)-1-(2,2,2-trifluoroethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(2,2-difluoroethyl)-N-(5-(1,1-difluoroethyl)-1-(2,2-difluoroethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-(prop-2-yn-1-yl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(1,1-difluoroethyl)-1-ethyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(1,5-diethyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(1,5-diethyl-1H-1,2,4-triazol-3-yl)-N-ethyl-2-methylbenzamide; N-(1-

(cyclopropylmethyl)-5-(trifluoromethyl)-1H-1,2,4-triazol-3-yl)-4-(5-(3,5-dichloro-4-fluorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-2-methyl-N-(1-(2,2,3,3,3-pentafluoropropyl)-5-(trifluoromethyl)-1H-1,2,4-triazol-3-yl)benzamide; 4-(5-(3,5-dichlorophenyl)-5-(trifluoromethyl)-4,5-dihydroisoxazol-3-yl)-N-(5-(fluoromethyl)-1-methyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-(1,1-difluoroethyl)-1-(prop-2-yn-1-yl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isopropyl-1-methyl-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-(1,1-difluoroethyl)-1-ethyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isopropyl-1-methyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(1-(2,2-difluoroethyl)-5-isopropyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-N-(5-(fluoromethyl)-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isobutyl-1-methyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-isopropyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isobutyl-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isopropyl-1-(2,2,2-trifluoroethyl)-1H-1,2,4-triazol-3-yl)-2-methyl-N-(2,2,2-trifluoroethyl)benzamide; 4-(5-(3,5-dichlorophenyl)-5-(trifluoromethyl)-4,5-dihydroisoxazol-3-yl)-2-methyl-N-(1-methyl-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-N-(1-ethyl-5-isopropyl-1H-1,2,4-triazol-3-yl)-2-methylbenzamide; 4-(5-(3,5-dichlorophenyl)-5-(trifluoromethyl)-4,5-dihydroisoxazol-3-yl)-2-methyl-N-(1-(2,2,2-trifluoroethyl)-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-N,2-dimethyl-N-(1-methyl-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-2-methyl-N-(2,2,2-trifluoroethyl)-N-(1-(2,2,2-trifluoroethyl)-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-2-methyl-N-(1-methyl-5-(2,2,2-trifluoroethyl)-1H-1,2,4-triazol-3-yl)benzamide; 4-(5-(3,5-dichlorophenyl)-5-(trifluoromethyl)-4,5-dihydroisoxazol-3-yl)-N-(1-(2,2-difluoroethyl)-5-(3,3,3-trifluoropropyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-ethyl-5-(3,3,3-trifluoropropyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-(3,3,3-trifluoropropyl)-1H-1,2,4-triazol-3-yl)-2-methylbenzamide; 4-(5-(3,5-dichlorophenyl)-5-(trifluoromethyl)-4,5-dihydroisoxazol-3-yl)-2-methyl-N-(1-(prop-2-yn-1-yl)-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-2-methyl-N-(prop-2-yn-1-yl)-N-(1-(prop-2-yn-1-yl)-5-(3,3,3-trifluoropropyl)-1H-1,2,4-triazol-3-yl)benzamide; 4-(5-(3,5-dichlorophenyl)-5-(trifluoromethyl)-4,5-dihydroisoxazol-3-yl)-N-(5-isopropyl-1-(prop-2-yn-1-yl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-isopropyl-1-(prop-2-yn-1-yl)-1H-1,2,4-triazol-3-yl)-2-methyl-N-(prop-2-yn-1-yl)benzamide; N-(1-allyl-5-(3,3,3-trifluoropropyl)-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichlorophenyl)-5-(trifluoromethyl)-4,5-dihydroisoxazol-3-yl)-N-(5-(methoxymethyl)-1-methyl-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(methoxymethyl)-1-methyl-1H-1,2,4-triazol-3-yl)-N,2-dimethylbenzamide; 4-(5-(3,5-dichlorophenyl)-5-(trifluoromethyl)-4,5-dihydroisoxazol-3-yl)-N-(5-(methoxymethyl)-1-(2,2,2-trifluoroethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-ethyl-5-(methoxymethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(methoxymethyl)-1-(2,2,2-trifluoroethyl)-1H-1,2,4-triazol-3-yl)-2-methyl-N-(2,2,2-trifluoroethyl)benzamide; 4-(5-(3,5-dichlorophenyl)-5-(trifluoromethyl)-4,5-dihydroisoxazol-3-yl)-N-ethyl-N-(1-ethyl-5-(methoxymethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(1-(2,2-difluoroethyl)-5-(methoxymethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(methoxymethyl)-1-(prop-2-yn-1-yl)-1H-1,2,4-triazol-3-yl)-2-methylbenzamide; 4-(5-(3,5-dichlorophenyl)-5-(trifluoromethyl)-4,5-dihydroisoxazol-3-yl)-N-(2,2-difluoroethyl)-N-(1-(2,2-difluoroethyl)-5-(methoxymethyl)-1H-1,2,4-triazol-3-yl)-2-methylbenzamide; 4-(5-(3,5-dichlorophenyl)-5-(trifluoromethyl)-4,5-dihydroisoxazol-3-yl)-N-(5-(methoxymethyl)-1-(prop-2-yn-1-yl)-1H-1,2,4-triazol-3-yl)-2-methyl-N-(prop-2-yn-1-yl)benzamide; N-(1-allyl-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide; N-(1-(cyanomethyl)-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide; N-(cyanomethyl)-N-(1-(cyanomethyl)-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide; N-allyl-N-(1-allyl-5-(methoxymethyl)-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-2-methyl-N-(1-(2,2,2-trifluoroethyl)-5-(3,3,3-trifluoropropyl)-1H-1,2,4-triazol-3-yl)benzamide; 4-(5-(3,5-dichloro-4-fluorophenyl)-5-(trifluoromethyl)-4,5-dihydroisoxazol-3-yl)-2-methyl-N-(1-methyl-5-(3,3,3-trifluoropropyl)-1H-1,2,4-triazol-3-yl)benzamide; 4-(5-(3,5-dichloro-4-fluorophenyl)-5-(trifluoromethyl)-4,5- dihydroisoxazol-3-yl)-N,2-dimethyl-N-(1-methyl-5-(3,3,3-trifluoropropyl)-1H-1,2,4-triazol-3-yl)benzamide; 4-(5-(3,5-dichloro-4-fluorophenyl)-5-(trifluoromethyl)-4,5-dihydroisoxazol-3-yl)-2-methyl-N-(2,2,2-trifluoroethyl)-N-(1-(2,2,2-trifluoroethyl)-5-(3,3,3-trifluoropropyl)-1H-1,2,4-triazol-3-yl)benzamide; N-(1-(cyanomethyl)-5-(3,3,3-trifluoropropyl)-1H-1,2,4-triazol-3-yl)-4-(5-(3,5-dichlorophenyl)-5-(trifluoromethyl)-4,5-dihydroisoxazol-3-yl)-2-methylbenzamide; N-(cyanomethyl)-N-(1-(cyanomethyl)-5-(3,3,3-trifluoropropyl)-1H-1,2,4-triazol-3-yl)-4-(5-(3,5-dichlorophenyl)-5-(trifluoromethyl)-4,5-dihydroisoxazol-3-yl)-2-methylbenzamide; 4-(5-(3,5-dichloro-4-fluorophenyl)-5-(trifluoromethyl)-4,5-dihydroisoxazol-3-yl)-N-(1-(2,2-difluoroethyl)-5-(3,3,3-trifluoropropyl)-1H-1,2,4-triazol-3-yl)-2-methylbenzamide; 4-(5-(3,5-dichloro-4-fluorophenyl)-5-(trifluoromethyl)-4,5-dihydroisoxazol-3-yl)-2-methyl-N-(prop-2-yn-1-yl)-N-(1-(prop-2-yn-1-yl)-5-(3,3,3-trifluoropropyl)-1H-1,2,4-triazol-3-yl)benzamide and salts, stereo-isomers, metal complexes, polymorphs or N-oxides thereof.

5. A method for preparing the compound of formula (I) as claimed in claim 1, wherein the said method comprises the steps of:

a) reacting a compound of formula (V) with a compound of formula (VII) in the presence of suitable reagents and solvents to obtain a compound of formula (X) according to the reaction scheme as depicted below:

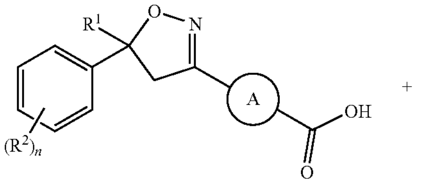

(V)

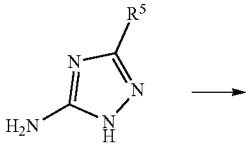

(VII)

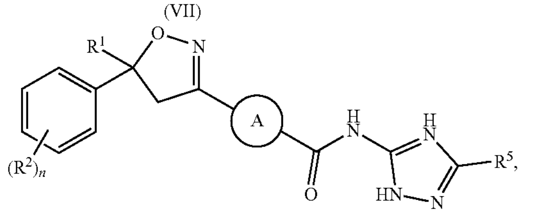

(X)

wherein, $R^1$, $R^2$, $R^5$, A and n are as defined in the claim 1;

b) optionally, a compound of formula (X) is obtained by converting a compound of formula (V) to a compound of formula (VIII) and further converted to a compound of formula (X) in the presence of suitable reagents and solvents, according to the reaction scheme as depicted below:

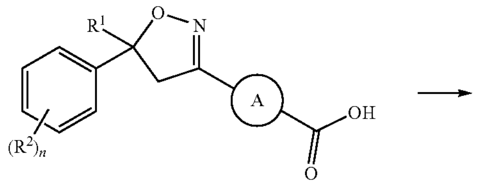

(V)

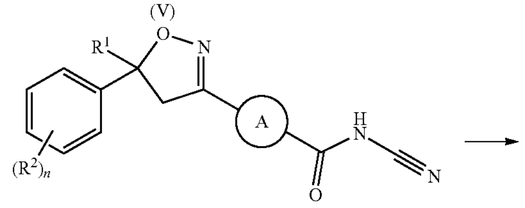

(VIII)

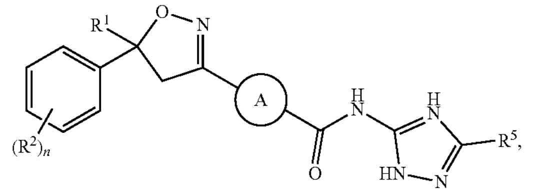

(X)

wherein, $R^1$, $R^2$, $R^5$, A and n are as defined in the claim 1;

c) further, a compound of formula (I) is obtained by converting a compound of formula (X) to a compound of formula (I) in the presence of suitable reagents and solvents according to the reaction scheme as depicted below:

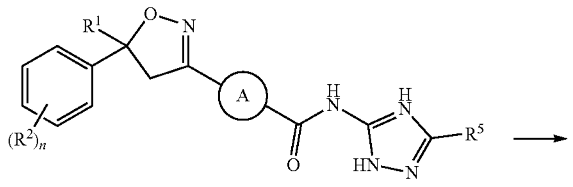

(X)

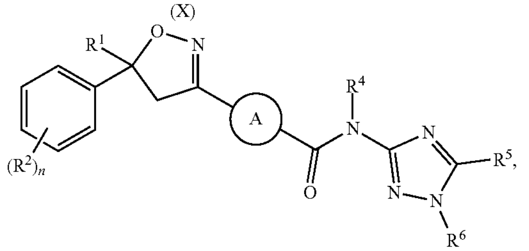

(I)

wherein, $R^1$, $R^2$, $R^4$, $R^5$, $R^6$, A and n are as defined in the claim 1.

6. A composition comprising the compound of formula (I) or agronomically acceptable salts, stereo-isomers, polymorphs or N-oxides thereof according to claim 1 and at least one additional component selected from the group consisting of surfactants and auxiliaries.

7. The composition according to claim 6, wherein the said composition additionally comprises at least one biological active compatible compound selected from fungicides, insecticides, nematicides, acaricides, biopesticides, herbicides, plant growth regulators, antibiotics, fertilizers or nutrients.

8. The composition according to claim 6, wherein the said compound of formula (I) ranges from 0.1% to 99% by weight with respect to the total weight of the composition.

9. A combination comprising a biologically effective amount of the compound of formula (I) according to claim 1 and at least one additional biological active compatible compound selected from fungicides, insecticides, nematicides, acaricides, biopesticides, herbicides, plant growth regulators, antibiotics, fertilizers and nutrients.

10. A method for combating insects and mite pests comprising contacting the insects and mite pests, their habitat, breeding ground, food supply, plant, seed, soil, area, material or environment in which the insect and mite pests are growing or may grow, or the materials, plants, seeds, soils, surfaces or spaces to be protected from pest attack or infestation with a biologically effective amount of compound of formula (I), salts, stereoisomers, polymorphs, metal complexes, N-oxides composition or combination thereof according to claim 1.

11. A method for protecting crops from attack or infestation by insects and mite pests comprises contacting the crop with the compound of formula (I), agronomically acceptable salts, stereo-isomers, polymorphs, metal complexes, N-oxides composition or combination thereof according to claim 1.

12. The method according to claim 10, wherein the said method comprises applying effective dosages of a compound of formula (I) in amounts ranging from 1 gai to 5000 gai per hectare in agricultural or horticultural crops.

13. A method for the protection of seeds, plants and plant parts from soil insects and of the seedlings roots and shoots from soil and foliar insects comprising contacting the seeds before sowing and/or after pre-germination with the compound of formula (I), salts, stereoisomers, polymorphs, metal complexes, N-oxides composition or combination thereof according to claim 1.

14. A method for combating insects and mite pests in agricultural crops, horticultural crops, household and vector control and parasites on animals comprising:

applying the composition of claim 6.

15. The method of claim 14, wherein the said agricultural crops are cereals, corn, sorghum, bajra, rice, soybean, oil seeds and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers, other vegetables and ornamentals.

16. A seed comprising a compound of formula (I) or salts, metal complexes, N-oxides, stereoisomers, polymorphs, composition or combination thereof according to claim 1 coated thereon, wherein the amount of the compound of formula (I) in the said seed is ranging from about 0.0001% to about 1% by weight.

17. The composition according to claim 6, wherein the said compound of formula (I) ranges from 5 to 50% by weight with respect to the total weight of the composition.

* * * * *